United States Patent
Zopf et al.

(10) Patent No.: US 9,050,304 B2
(45) Date of Patent: *Jun. 9, 2015

(54) METHODS OF TREATMENT USING GLYCOPEGYLATED G-CSF

(75) Inventors: David A. Zopf, Wayne, PA (US); Heinz Lubenau, Neustadt (DE)

(73) Assignee: ratiopharm GmbH, Ulm (DE)

( * ) Notice: Subject to any disclaimer, the term of this patent is extended or adjusted under 35 U.S.C. 154(b) by 514 days.

This patent is subject to a terminal disclaimer.

(21) Appl. No.: 12/594,326

(22) PCT Filed: Apr. 1, 2008

(86) PCT No.: PCT/US2008/059045
§ 371 (c)(1),
(2), (4) Date: Jan. 13, 2010

(87) PCT Pub. No.: WO2008/124406
PCT Pub. Date: Oct. 16, 2008

(65) Prior Publication Data
US 2010/0120666 A1  May 13, 2010

Related U.S. Application Data

(60) Provisional application No. 60/986,240, filed on Nov. 7, 2007, provisional application No. 60/911,788, filed on Apr. 13, 2007, provisional application No. 60/909,917, filed on Apr. 3, 2007.

(51) Int. Cl.
| | |
|---|---|
| A61K 38/18 | (2006.01) |
| A61K 38/00 | (2006.01) |
| A61P 7/06 | (2006.01) |
| C07K 14/535 | (2006.01) |
| A61K 38/19 | (2006.01) |
| A61K 9/00 | (2006.01) |
| A61K 47/48 | (2006.01) |

(52) U.S. Cl.
CPC ............. *A61K 38/193* (2013.01); *A61K 9/0019* (2013.01); *A61K 47/48215* (2013.01)

(58) Field of Classification Search
CPC .................................................... A61K 38/193
See application file for complete search history.

(56) References Cited

U.S. PATENT DOCUMENTS

| | | |
|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts |
| 4,412,989 A | 11/1983 | Iwashita et al. |
| 4,414,147 A | 11/1983 | Klibanov et al. |
| 4,438,253 A | 3/1984 | Casey et al. |
| 4,451,566 A | 5/1984 | Spencer |
| 4,496,689 A | 1/1985 | Mitra |
| 4,565,653 A | 1/1986 | Ives et al. |
| 4,675,414 A | 6/1987 | DeFusco et al. |
| 4,704,361 A | 11/1987 | Miccoli et al. |
| 4,767,702 A | 8/1988 | Cohenford |
| 4,806,595 A | 2/1989 | Noishiki et al. |
| 4,826,945 A | 5/1989 | Cohn et al. |
| 4,847,325 A | 7/1989 | Shadle et al. |
| 4,879,236 A | 11/1989 | Smith et al. |
| 4,918,009 A | 4/1990 | Nilsson |
| 4,925,796 A | 5/1990 | Bergh et al. |
| 4,980,502 A | 12/1990 | Felder et al. |
| 5,032,519 A | 7/1991 | Paulson et al. |
| 5,047,335 A | 9/1991 | Paulson et al. |
| 5,104,651 A | 4/1992 | Boone et al. |
| 5,122,614 A | 6/1992 | Zalipsky |
| 5,147,788 A | 9/1992 | Page et al. |
| 5,153,265 A | 10/1992 | Shadle et al. |
| 5,154,924 A | 10/1992 | Friden |
| 5,164,374 A | 11/1992 | Rademacher et al. |
| 5,166,322 A | 11/1992 | Shaw et al. |
| 5,169,933 A | 12/1992 | Anderson et al. |
| 5,180,674 A | 1/1993 | Roth |
| 5,182,107 A | 1/1993 | Friden |
| 5,194,376 A | 3/1993 | Kang |
| 5,202,413 A | 4/1993 | Spinu |
| 5,206,344 A | 4/1993 | Katre et al. |
| 5,219,564 A | 6/1993 | Zalipsky et al. |
| 5,272,066 A | 12/1993 | Bergh et al. |

(Continued)

FOREIGN PATENT DOCUMENTS

| | | |
|---|---|---|
| AU | 1991/083760 A | 3/1992 |
| AU | 1992/017052 | 12/1992 |

(Continued)

OTHER PUBLICATIONS

Broxmeyer et al., J Exp Med. Apr. 18, 2005;201(8):1307-1318.*
DeFrees et al., Glycobiology, 16(9): 833-843 (2006).
Office Action dated Sep. 20, 1994 in U.S. Appl. No. 08/215,727.
Office Action dated May 4, 1995 in U.S. Appl. No. 08/102,385.
Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S. Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.
Office Action dated Aug. 8, 1997 in U.S. Appl. No. 08/745,840.
Office Action dated Oct. 9, 1997 in U.S. Appl. No. 08/478,140.
Office Action dated Dec. 1, 1997 in U.S. Appl. No. 08/446,875.

(Continued)

*Primary Examiner* — Daniel C Gamett
(74) *Attorney, Agent, or Firm* — Leydig, Voit & Mayer, Ltd.

(57) ABSTRACT

The present invention provides a glycopegylated G-CSF that is therapeutically active and which has pharmacokinetic parameters and properties that are improved relative to an identical, or closely analogous, G-CSF peptide that is not glycopegylated. Furthermore, the invention provides methods for mobilizing hematopoiesis in a subject, particularly a subject who has received or will receive radiation or chemotherapy treatment. The methods and compositions of the invention can further be used to prevent, alleviate and treat the myelosuppressive effects such therapies.

37 Claims, 10 Drawing Sheets

(56) References Cited

U.S. PATENT DOCUMENTS

| | | |
|---|---|---|
| 5,278,299 A | 1/1994 | Wong et al. |
| 5,281,698 A | 1/1994 | Nitecki |
| 5,288,637 A | 2/1994 | Roth |
| 5,308,460 A | 5/1994 | Mazid et al. |
| 5,324,663 A | 6/1994 | Lowe |
| 5,324,844 A | 6/1994 | Zalipsky |
| 5,342,940 A | 8/1994 | Ono et al. |
| 5,346,696 A | 9/1994 | Kim et al. |
| 5,352,670 A | 10/1994 | Venot et al. |
| 5,369,017 A | 11/1994 | Wong et al. |
| 5,374,541 A | 12/1994 | Wong et al. |
| 5,374,655 A | 12/1994 | Kashem et al. |
| 5,384,249 A | 1/1995 | Sasaki et al. |
| 5,399,345 A | 3/1995 | Schumacher et al. |
| 5,405,753 A | 4/1995 | Brossmer et al. |
| 5,409,817 A | 4/1995 | Ito et al. |
| 5,410,016 A | 4/1995 | Hubbell et al. |
| 5,432,059 A | 7/1995 | Bean et al. |
| 5,446,090 A | 8/1995 | Harris |
| 5,492,821 A | 2/1996 | Callstrom et al. |
| 5,492,841 A | 2/1996 | Craig |
| 5,527,527 A | 6/1996 | Friden |
| 5,529,914 A | 6/1996 | Hubbell et al. |
| 5,545,553 A | 8/1996 | Gotschlich |
| 5,567,422 A | 10/1996 | Greenwald |
| 5,583,042 A | 12/1996 | Roth |
| 5,595,900 A | 1/1997 | Lowe |
| 5,605,793 A | 2/1997 | Stemmer |
| 5,614,184 A | 3/1997 | Sytkowski et al. |
| 5,621,039 A | 4/1997 | Hallahan et al. |
| 5,629,384 A | 5/1997 | Veronese et al. |
| 5,635,603 A | 6/1997 | Hansen et al. |
| 5,643,575 A | 7/1997 | Martinez et al. |
| 5,646,113 A | 7/1997 | Attie et al. |
| 5,672,662 A | 9/1997 | Harris et al. |
| 5,672,683 A | 9/1997 | Friden et al. |
| 5,705,367 A | 1/1998 | Gotschlich |
| 5,714,166 A | 2/1998 | Tomalia et al. |
| 5,716,812 A | 2/1998 | Withers et al. |
| 5,723,121 A | 3/1998 | Takenaga et al. |
| 5,728,554 A | 3/1998 | Bayer et al. |
| 5,739,208 A | 4/1998 | Harris |
| 5,762,920 A * | 6/1998 | Yung et al. .................. 424/85.1 |
| 5,770,420 A | 6/1998 | Lowe et al. |
| 5,798,233 A | 8/1998 | Gotschlich |
| 5,811,238 A | 9/1998 | Stemmer et al. |
| 5,824,778 A | 10/1998 | Ishikawa et al. |
| 5,824,864 A | 10/1998 | Fox et al. |
| 5,830,721 A | 11/1998 | Stemmer et al. |
| 5,833,988 A | 11/1998 | Friden |
| 5,834,251 A | 11/1998 | Maras et al. |
| 5,837,458 A | 11/1998 | Minshull et al. |
| 5,849,535 A | 12/1998 | Cunningham et al. |
| 5,858,751 A | 1/1999 | Paulson et al. |
| 5,858,752 A | 1/1999 | Seed et al. |
| 5,861,374 A | 1/1999 | Berkner et al. |
| 5,874,075 A | 2/1999 | Collins et al. |
| 5,876,980 A | 3/1999 | DeFrees et al. |
| 5,922,577 A | 7/1999 | DeFrees et al. |
| 5,925,739 A | 7/1999 | Spira et al. |
| 5,932,462 A | 8/1999 | Harris et al. |
| 5,945,314 A | 8/1999 | Prieto et al. |
| 5,945,322 A | 8/1999 | Gotschlich |
| 5,955,347 A | 9/1999 | Lowe |
| 5,962,294 A | 10/1999 | Paulson et al. |
| 5,969,040 A | 10/1999 | Hallahan et al. |
| 5,977,307 A | 11/1999 | Friden et al. |
| 6,010,999 A | 1/2000 | Daley et al. |
| 6,015,555 A | 1/2000 | Friden |
| 6,030,815 A | 2/2000 | DeFrees et al. |
| 6,034,223 A | 3/2000 | Maddon et al. |
| 6,037,452 A | 3/2000 | Minamino et al. |
| 6,048,720 A | 4/2000 | Dalborg et al. |
| 6,057,292 A | 5/2000 | Cunningham et al. |
| 6,075,134 A | 6/2000 | Bertozzi et al. |
| 6,087,325 A | 7/2000 | Meers et al. |
| 6,096,512 A | 8/2000 | Elhammer et al. |
| 6,113,906 A | 9/2000 | Greenwald et al. |
| 6,117,651 A | 9/2000 | Schultz et al. |
| 6,127,153 A | 10/2000 | Johnson et al. |
| 6,156,547 A | 12/2000 | Roth |
| 6,166,183 A | 12/2000 | Ishikawa et al. |
| 6,183,738 B1 | 2/2001 | Clark |
| 6,251,864 B1 | 6/2001 | Dower et al. |
| 6,261,805 B1 | 7/2001 | Wood |
| 6,268,193 B1 | 7/2001 | Lowe |
| 6,319,695 B1 | 11/2001 | Wong et al. |
| 6,340,742 B1 | 1/2002 | Burg et al. |
| 6,342,382 B1 | 1/2002 | Gotschlich |
| 6,348,558 B1 | 2/2002 | Harris et al. |
| 6,361,977 B1 | 3/2002 | Bauer et al. |
| 6,362,254 B2 | 3/2002 | Harris et al. |
| 6,376,604 B2 | 4/2002 | Kozlowski |
| 6,379,933 B1 | 4/2002 | Johnson et al. |
| 6,399,336 B1 | 6/2002 | Paulson et al. |
| 6,399,337 B1 | 6/2002 | Taylor et al. |
| 6,440,703 B1 | 8/2002 | DeFrees |
| 6,458,937 B1 | 10/2002 | Bertozzi et al. |
| 6,465,220 B1 | 10/2002 | Hassan et al. |
| 6,495,365 B1 * | 12/2002 | Saito et al. .................. 435/387 |
| 6,531,121 B2 | 3/2003 | Brines et al. |
| 6,555,346 B1 | 4/2003 | Kretzdorn et al. |
| 6,555,660 B2 | 4/2003 | Nissen et al. |
| 6,586,398 B1 | 7/2003 | Kinstler et al. |
| 6,692,931 B1 | 2/2004 | Reutter et al. |
| 6,693,183 B2 | 2/2004 | Natsuka et al. |
| 6,716,626 B1 | 4/2004 | Itoh et al. |
| 6,743,896 B2 | 6/2004 | Filpula et al. |
| 6,780,624 B2 | 8/2004 | Gotschlich |
| 6,800,740 B1 | 10/2004 | Cunningham et al. |
| 6,949,372 B2 | 9/2005 | Betenbaugh et al. |
| 7,094,530 B1 | 8/2006 | Sasaki et al. |
| 7,125,843 B2 | 10/2006 | DeFrees et al. |
| 7,138,371 B2 | 11/2006 | DeFrees et al. |
| 7,157,277 B2 | 1/2007 | DeFrees et al. |
| 7,173,003 B2 | 2/2007 | DeFrees et al. |
| 7,179,617 B2 | 2/2007 | DeFrees et al. |
| 7,199,223 B2 | 4/2007 | Bossard et al. |
| 7,202,208 B2 | 4/2007 | Papadimitriou |
| 7,214,660 B2 | 5/2007 | DeFrees et al. |
| 7,226,903 B2 | 6/2007 | DeFrees et al. |
| 7,229,962 B2 | 6/2007 | Chung et al. |
| 7,235,638 B2 | 6/2007 | Persson |
| 7,265,084 B2 | 9/2007 | DeFrees et al. |
| 7,265,085 B2 | 9/2007 | DeFrees et al. |
| 7,276,475 B2 | 10/2007 | DeFrees et al. |
| 7,297,511 B2 | 11/2007 | DeFrees et al. |
| 7,304,150 B1 | 12/2007 | Egrie et al. |
| 7,338,933 B2 | 3/2008 | DeFrees et al. |
| 7,368,108 B2 | 5/2008 | DeFrees et al. |
| 7,399,613 B2 | 7/2008 | DeFrees et al. |
| 7,405,198 B2 | 7/2008 | DeFrees et al. |
| 7,416,858 B2 | 8/2008 | DeFrees et al. |
| 7,439,043 B2 | 10/2008 | DeFrees et al. |
| 7,473,680 B2 | 1/2009 | DeFrees et al. |
| 7,524,813 B2 | 4/2009 | Zundel et al. |
| 7,662,933 B2 | 2/2010 | Kinstler et al. |
| 7,691,603 B2 | 4/2010 | DeFrees |
| 7,696,163 B2 | 4/2010 | DeFrees et al. |
| 7,795,210 B2 | 9/2010 | DeFrees et al. |
| 7,803,777 B2 | 9/2010 | DeFrees |
| 7,842,661 B2 | 11/2010 | DeFrees et al. |
| 7,932,364 B2 | 4/2011 | DeFrees et al. |
| 7,956,032 B2 | 6/2011 | DeFrees et al. |
| 8,008,252 B2 | 8/2011 | Defrees et al. |
| 8,053,410 B2 | 11/2011 | Klausen et al. |
| 8,063,015 B2 | 11/2011 | DeFrees et al. |
| 8,076,292 B2 | 12/2011 | DeFrees et al. |
| 8,178,108 B2 | 5/2012 | Buechler et al. |
| 8,207,112 B2 | 6/2012 | Hinderer et al. |
| 8,247,381 B2 | 8/2012 | DeFrees |
| 8,268,967 B2 | 9/2012 | DeFrees |
| 8,361,961 B2 | 1/2013 | DeFrees et al. |
| 8,404,809 B2 | 3/2013 | DeFrees et al. |

(56) References Cited

U.S. PATENT DOCUMENTS

| | | |
|---|---|---|
| 8,633,157 B2 | 1/2014 | Defrees et al. |
| 8,633,300 B2 | 1/2014 | Ostergaard et al. |
| 8,716,239 B2 | 5/2014 | DeFrees et al. |
| 8,716,240 B2 | 5/2014 | DeFrees et al. |
| 8,791,066 B2 | 7/2014 | DeFrees |
| 8,791,070 B2 | 7/2014 | DeFrees et al. |
| 8,841,439 B2 | 9/2014 | Felo et al. |
| 8,853,161 B2 | 10/2014 | DeFrees et al. |
| 8,911,967 B2 | 12/2014 | DeFrees et al. |
| 2001/0041683 A1 | 11/2001 | Schmitz et al. |
| 2001/0043929 A1 | 11/2001 | Zalipsky et al. |
| 2002/0004483 A1 | 1/2002 | Nissen et al. |
| 2002/0016003 A1 | 2/2002 | Saxon et al. |
| 2002/0019342 A1 | 2/2002 | Bayer |
| 2002/0037841 A1 | 3/2002 | Papadimitriou |
| 2002/0068347 A1 | 6/2002 | Taylor et al. |
| 2002/0115833 A1 | 8/2002 | Burg et al. |
| 2002/0127682 A1 | 9/2002 | Gotschlich |
| 2002/0137134 A1 | 9/2002 | Gerngross et al. |
| 2002/0142370 A1 | 10/2002 | Paulson et al. |
| 2002/0142964 A1 | 10/2002 | Nissen et al. |
| 2002/0148791 A1 | 10/2002 | DeFrees |
| 2002/0150981 A1 | 10/2002 | Canfield |
| 2002/0168323 A1 | 11/2002 | Gonda |
| 2002/0182586 A1 | 12/2002 | Morris et al. |
| 2003/0003529 A1 | 1/2003 | Bayer |
| 2003/0027257 A1 | 2/2003 | Iatrou et al. |
| 2003/0040037 A1 | 2/2003 | Bayer |
| 2003/0044908 A1 | 3/2003 | Persson |
| 2003/0083251 A1 | 5/2003 | Westenfelder |
| 2003/0096338 A1 | 5/2003 | Pedersen et al. |
| 2003/0100075 A1 | 5/2003 | Persson et al. |
| 2003/0119090 A1 | 6/2003 | Wong |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0170863 A1 | 9/2003 | Persson et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0020857 A1 | 2/2004 | Belew et al. |
| 2004/0043446 A1 | 3/2004 | DeFrees et al. |
| 2004/0043464 A1 | 3/2004 | Gotschlich |
| 2004/0063911 A1 | 4/2004 | DeFrees et al. |
| 2004/0077836 A1 | 4/2004 | DeFrees et al. |
| 2004/0082026 A1 | 4/2004 | DeFrees et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker et al. |
| 2004/0137557 A1 | 7/2004 | DeFrees et al. |
| 2004/0142856 A1 | 7/2004 | DeFrees et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0032742 A1 | 2/2005 | DeFrees et al. |
| 2005/0064540 A1 | 3/2005 | DeFrees et al. |
| 2005/0085631 A1 | 4/2005 | Boyle et al. |
| 2005/0100982 A1 | 5/2005 | DeFrees et al. |
| 2005/0106658 A1 | 5/2005 | DeFrees et al. |
| 2005/0113565 A1 | 5/2005 | Klausen et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0029573 A1 | 2/2006 | Shen et al. |
| 2006/0030521 A1 | 2/2006 | DeFrees et al. |
| 2006/0035224 A1 | 2/2006 | Johansen |
| 2006/0040856 A1 | 2/2006 | DeFrees et al. |
| 2006/0088906 A1 | 4/2006 | DeFrees et al. |
| 2006/0111279 A1 | 5/2006 | DeFrees et al. |
| 2006/0165728 A1 | 7/2006 | Young et al. |
| 2006/0177892 A1 | 8/2006 | De Frees |
| 2006/0182714 A1 | 8/2006 | Behrens et al. |
| 2006/0183198 A1 | 8/2006 | Buechler et al. |
| 2006/0198819 A1 | 9/2006 | Behrens et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees et al. |
| 2007/0037966 A1 | 2/2007 | Rasmussen et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0254834 A1 | 11/2007 | DeFrees et al. |
| 2007/0254836 A1 | 11/2007 | DeFrees et al. |
| 2008/0015142 A1 | 1/2008 | DeFrees et al. |
| 2008/0039373 A1 | 2/2008 | Klausen et al. |
| 2008/0050772 A1 | 2/2008 | DeFrees et al. |
| 2008/0070275 A1 | 3/2008 | DeFrees et al. |
| 2008/0102083 A1 | 5/2008 | DeFrees et al. |
| 2008/0108557 A1 | 5/2008 | Behrens et al. |
| 2008/0146494 A1 | 6/2008 | DeFrees et al. |
| 2008/0146782 A1 | 6/2008 | DeFrees et al. |
| 2008/0176790 A1 | 7/2008 | DeFrees |
| 2008/0187955 A1 | 8/2008 | DeFrees et al. |
| 2008/0200651 A1 | 8/2008 | Ostergaard et al. |
| 2008/0206808 A1 | 8/2008 | DeFrees et al. |
| 2008/0206810 A1 | 8/2008 | Johnson et al. |
| 2008/0207487 A1 | 8/2008 | DeFrees et al. |
| 2008/0242607 A1 | 10/2008 | DeFrees |
| 2008/0242846 A1 | 10/2008 | DeFrees et al. |
| 2008/0248959 A1 | 10/2008 | DeFrees |
| 2008/0253992 A1 | 10/2008 | DeFrees et al. |
| 2008/0255026 A1 | 10/2008 | DeFrees et al. |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2008/0300175 A1 | 12/2008 | DeFrees et al. |
| 2008/0305518 A1 | 12/2008 | Klausen et al. |
| 2008/0305991 A1 | 12/2008 | DeFrees et al. |
| 2008/0305992 A1 | 12/2008 | DeFrees et al. |
| 2008/0318850 A1 | 12/2008 | DeFrees et al. |
| 2008/0319183 A1 | 12/2008 | DeFrees et al. |
| 2009/0028822 A1 | 1/2009 | DeFrees et al. |
| 2009/0048440 A1 | 2/2009 | Felo et al. |
| 2009/0053167 A1 | 2/2009 | DeFrees |
| 2009/0054623 A1 | 2/2009 | DeFrees |
| 2009/0055942 A1 | 2/2009 | Ostergaard et al. |
| 2009/0076237 A1 | 3/2009 | Turecek et al. |
| 2009/0081188 A1 | 3/2009 | DeFrees et al. |
| 2009/0093399 A1 | 4/2009 | DeFrees et al. |
| 2009/0124544 A1 | 5/2009 | DeFrees |
| 2009/0137763 A1 | 5/2009 | DeFrees et al. |
| 2009/0143292 A1 | 6/2009 | Hinderer et al. |
| 2009/0169509 A1 | 7/2009 | DeFrees et al. |
| 2009/0176967 A1 | 7/2009 | Stennicke |
| 2009/0203579 A1 | 8/2009 | DeFrees et al. |
| 2009/0227504 A1 | 9/2009 | Klausen et al. |
| 2009/0240028 A1 | 9/2009 | Behrens et al. |
| 2009/0247450 A1 | 10/2009 | Mack |
| 2009/0252720 A1 | 10/2009 | Ostergaard et al. |
| 2009/0253166 A1 | 10/2009 | Zundel et al. |
| 2009/0264366 A1 | 10/2009 | Johansen et al. |
| 2009/0292110 A1 | 11/2009 | DeFrees |
| 2009/0305967 A1 | 12/2009 | DeFrees et al. |
| 2010/0009902 A1 | 1/2010 | DeFrees |
| 2010/0015684 A1 | 1/2010 | DeFrees et al. |
| 2010/0028939 A1 | 2/2010 | Behrens et al. |
| 2010/0029555 A1 | 2/2010 | Tonon et al. |
| 2010/0035299 A1 | 2/2010 | DeFrees et al. |
| 2010/0041872 A1 | 2/2010 | DeFrees et al. |

(56) References Cited

U.S. PATENT DOCUMENTS

| | | |
|---|---|---|
| 2010/0048456 A1 | 2/2010 | DeFrees et al. |
| 2010/0056428 A1 | 3/2010 | Behrens |
| 2010/0075375 A1 | 3/2010 | DeFrees et al. |
| 2010/0081791 A1 | 4/2010 | DeFrees et al. |
| 2010/0113743 A1 | 5/2010 | DeFrees et al. |
| 2010/0120666 A1 | 5/2010 | Zopf et al. |
| 2010/0174056 A1 | 7/2010 | Gillies et al. |
| 2010/0174059 A1 | 7/2010 | DeFrees et al. |
| 2010/0210507 A9 | 8/2010 | DeFrees et al. |
| 2010/0261872 A1 | 10/2010 | DeFrees et al. |
| 2010/0286067 A1 | 11/2010 | DeFrees |
| 2010/0322940 A1 | 12/2010 | Bayer |
| 2010/0330645 A1 | 12/2010 | DeFrees et al. |
| 2010/0331489 A1 | 12/2010 | DeFrees |
| 2011/0003744 A1 | 1/2011 | DeFrees et al. |
| 2011/0064719 A1 | 3/2011 | Rasmussen et al. |
| 2011/0177029 A1 | 7/2011 | DeFrees |
| 2011/0223646 A1 | 9/2011 | Schwartz et al. |
| 2011/0318780 A1 | 12/2011 | DeFrees |
| 2012/0016105 A1 | 1/2012 | DeFrees et al. |
| 2012/0083600 A1 | 4/2012 | Felo et al. |
| 2012/0107867 A1 | 5/2012 | DeFrees et al. |
| 2012/0172300 A1 | 7/2012 | DeFrees |
| 2012/0220517 A1 | 8/2012 | DeFrees et al. |
| 2013/0059780 A1 | 3/2013 | DeFrees |
| 2013/0344050 A1 | 12/2013 | DeFrees et al. |
| 2014/0112903 A1 | 4/2014 | DeFrees et al. |
| 2014/0294762 A1 | 10/2014 | DeFrees et al. |

FOREIGN PATENT DOCUMENTS

| | | |
|---|---|---|
| CA | 2131703 A1 | 9/1993 |
| CA | 2110543 A1 | 6/1994 |
| CA | 2324616 A1 | 9/1999 |
| CA | 2167521 | 10/2003 |
| CA | 2500389 A1 | 4/2004 |
| CA | 2511814 A1 | 7/2004 |
| DE | 2437388 | 2/1975 |
| DE | 19709787 | 9/1998 |
| DE | 19852729 A1 | 5/2000 |
| EP | 0119539 A2 | 9/1984 |
| EP | 0200421 A2 | 12/1986 |
| EP | 0370205 A2 | 5/1990 |
| EP | 0459630 A2 | 12/1991 |
| EP | 0474313 A2 | 3/1992 |
| EP | 0475354 A2 | 3/1992 |
| EP | 0577580 A2 | 1/1994 |
| EP | 0585109 A2 | 3/1994 |
| EP | 0605963 A2 | 7/1994 |
| EP | 0775711 A1 | 5/1997 |
| EP | 0863154 A1 | 9/1998 |
| EP | 1260582 A1 | 11/2002 |
| EP | 1270642 A1 | 1/2003 |
| EP | 1428878 A1 | 6/2004 |
| EP | 1481985 A1 | 12/2004 |
| FI | 922515 A | 12/1992 |
| GB | 2256197 A | 12/1992 |
| JP | S59172425 A | 9/1984 |
| JP | H02-076894 A | 3/1990 |
| JP | H03-503759 A | 8/1991 |
| JP | H06-086684 A | 3/1994 |
| JP | H06-160365 A | 6/1994 |
| JP | H06-172375 A | 6/1994 |
| JP | H07-196925 A | 8/1995 |
| JP | H07-223921 A | 8/1995 |
| JP | H08-506023 A | 7/1996 |
| JP | H09-503905 A | 4/1997 |
| JP | H09-208461 A | 8/1997 |
| JP | H10-307356 A | 11/1998 |
| JP | 2000-501607 A | 2/2000 |
| JP | 2001-508783 A | 7/2001 |
| JP | 2001-519784 A | 10/2001 |
| JP | 2003-521930 A | 7/2003 |
| JP | 2005-521635 A | 7/2005 |
| JP | 2005-328782 A | 12/2005 |
| KR | 2002-0010363 A | 2/2002 |
| KR | 10-0396983 B1 | 8/2003 |
| NZ | 532027 A | 9/2008 |
| NZ | 539415 A | 12/2008 |
| NZ | 547554 A | 9/2009 |
| RU | 2005/101348 A | 8/2005 |
| SE | 9501285 | 10/1996 |
| WO | WO 87/00056 A1 | 1/1987 |
| WO | WO 87/05330 A1 | 9/1987 |
| WO | WO 89/06546 A1 | 7/1989 |
| WO | WO 89/10134 A1 | 11/1989 |
| WO | WO 90/07572 A1 | 7/1990 |
| WO | WO 90/08164 A1 | 7/1990 |
| WO | WO 90/08823 A1 | 8/1990 |
| WO | 90/12090 A1 | 10/1990 |
| WO | WO 90/13540 A1 | 11/1990 |
| WO | 91/06635 A1 | 5/1991 |
| WO | 91/09122 A1 | 6/1991 |
| WO | WO 91/14697 A1 | 10/1991 |
| WO | WO 92/01055 A1 | 1/1992 |
| WO | 92/15686 A1 | 9/1992 |
| WO | 92/16555 A1 | 10/1992 |
| WO | 92/16640 A1 | 10/1992 |
| WO | WO 92/18135 A1 | 10/1992 |
| WO | WO 92/22310 A1 | 12/1992 |
| WO | 93/08842 A1 | 5/1993 |
| WO | 93/13198 A1 | 7/1993 |
| WO | WO 93/15189 A1 | 8/1993 |
| WO | 93/18787 A1 | 9/1993 |
| WO | WO 94/04193 A1 | 3/1994 |
| WO | WO 94/05332 A2 | 3/1994 |
| WO | WO 94/09027 A1 | 4/1994 |
| WO | WO 94/15625 A1 | 7/1994 |
| WO | WO 94/17039 A1 | 8/1994 |
| WO | WO 94/18247 A1 | 8/1994 |
| WO | 94/25614 A1 | 11/1994 |
| WO | 94/25615 A1 | 11/1994 |
| WO | 94/26760 A1 | 11/1994 |
| WO | 94/27631 A1 | 12/1994 |
| WO | WO 94/28024 A1 | 12/1994 |
| WO | WO 95/02421 A1 | 1/1995 |
| WO | 95/05465 A1 | 2/1995 |
| WO | WO 95/04278 A1 | 2/1995 |
| WO | 96/10089 A1 | 4/1996 |
| WO | WO 96/11953 A1 | 4/1996 |
| WO | 96/12800 A1 | 5/1996 |
| WO | WO 96/21468 A1 | 7/1996 |
| WO | WO 96/21469 A1 | 7/1996 |
| WO | 96/32492 A1 | 10/1996 |
| WO | WO 96/32491 A1 | 10/1996 |
| WO | WO 96/34015 A1 | 10/1996 |
| WO | WO 96/36357 A1 | 11/1996 |
| WO | WO 96/40731 A1 | 12/1996 |
| WO | WO 96/40881 A1 | 12/1996 |
| WO | WO 97/05330 A1 | 2/1997 |
| WO | 97/21822 A2 | 6/1997 |
| WO | 97/47651 A1 | 12/1997 |
| WO | WO 98/05363 A2 | 2/1998 |
| WO | 98/032466 A1 | 7/1998 |
| WO | WO 98/31826 A1 | 7/1998 |
| WO | WO 98/41562 A1 | 9/1998 |
| WO | WO 98/51784 A1 | 11/1998 |
| WO | WO 98/58964 A1 | 12/1998 |
| WO | WO 99/00150 A2 | 1/1999 |
| WO | 99/13063 A1 | 3/1999 |
| WO | WO 99/14259 A1 | 3/1999 |
| WO | WO 99/22764 A1 | 5/1999 |
| WO | 99/28491 A1 | 6/1999 |
| WO | 99/37779 A1 | 7/1999 |
| WO | WO 99/34833 A1 | 7/1999 |
| WO | WO 99/45964 A1 | 9/1999 |
| WO | WO 99/48515 A1 | 9/1999 |
| WO | WO 99/54342 A1 | 10/1999 |
| WO | WO 99/55376 A1 | 11/1999 |
| WO | WO 00/23114 A2 | 4/2000 |
| WO | 00/29558 A1 | 5/2000 |
| WO | 00/29603 A2 | 5/2000 |
| WO | WO 00/26354 A1 | 5/2000 |

(56) References Cited

FOREIGN PATENT DOCUMENTS

| | | |
|---|---|---|
| WO | 00/44785 A1 | 8/2000 |
| WO | 00/46379 A1 | 8/2000 |
| WO | WO 00/65087 A1 | 11/2000 |
| WO | WO 01/02017 A2 | 1/2001 |
| WO | WO 01/05434 A2 | 1/2001 |
| WO | 01/19955 A2 | 3/2001 |
| WO | WO 01/39788 A2 | 6/2001 |
| WO | WO 01/49830 A2 | 7/2001 |
| WO | WO 01/51510 A2 | 7/2001 |
| WO | WO 01/58493 A1 | 8/2001 |
| WO | WO 01/58935 A2 | 8/2001 |
| WO | WO 01/60411 A1 | 8/2001 |
| WO | WO 01/76640 A2 | 10/2001 |
| WO | 01/83725 A1 | 11/2001 |
| WO | 01/87329 A1 | 11/2001 |
| WO | 01/87925 A2 | 11/2001 |
| WO | WO 01/88117 A2 | 11/2001 |
| WO | WO 02/02597 A2 | 1/2002 |
| WO | WO 02/02764 A2 | 1/2002 |
| WO | WO 02/13843 A2 | 2/2002 |
| WO | WO 02/13873 A2 | 2/2002 |
| WO | 02/29025 A2 | 4/2002 |
| WO | 02/49673 A2 | 6/2002 |
| WO | 02/50099 A2 | 6/2002 |
| WO | WO 02/44196 A1 | 6/2002 |
| WO | WO 02/053580 A2 | 7/2002 |
| WO | WO 02/074806 A2 | 9/2002 |
| WO | 02/077218 A1 | 10/2002 |
| WO | WO 02/092619 A2 | 11/2002 |
| WO | 03/006501 A2 | 1/2003 |
| WO | 03/011879 A1 | 2/2003 |
| WO | WO 03/017949 A2 | 3/2003 |
| WO | 03/029291 A2 | 4/2003 |
| WO | WO 03/031464 A2 | 4/2003 |
| WO | WO 03/045980 A2 | 6/2003 |
| WO | WO 03/046150 A2 | 6/2003 |
| WO | WO 03/093448 A2 | 11/2003 |
| WO | WO 2004/000366 A1 | 12/2003 |
| WO | WO 2004/009838 A2 | 1/2004 |
| WO | WO 2004/010327 A2 | 1/2004 |
| WO | 2004/014417 A2 | 2/2004 |
| WO | WO 2004/022004 A2 | 3/2004 |
| WO | 2004/029090 A1 | 4/2004 |
| WO | 2004/029091 A2 | 4/2004 |
| WO | WO 2004/033651 A2 | 4/2004 |
| WO | 2004/047858 A1 | 6/2004 |
| WO | WO 2004/046222 A1 | 6/2004 |
| WO | WO 2004/067566 A1 | 8/2004 |
| WO | 2004/075923 A2 | 9/2004 |
| WO | WO 2004/083258 A2 | 9/2004 |
| WO | WO 2004/083259 A2 | 9/2004 |
| WO | WO 2004/091499 A2 | 10/2004 |
| WO | 2004/093823 A2 | 11/2004 |
| WO | 2004/101597 A2 | 11/2004 |
| WO | 2004/101740 A2 | 11/2004 |
| WO | WO 2004/096148 A2 | 11/2004 |
| WO | WO 2004/099231 A2 | 11/2004 |
| WO | 2004/106373 A1 | 12/2004 |
| WO | WO 2004/103275 A2 | 12/2004 |
| WO | 2005/001025 A2 | 1/2005 |
| WO | 2005/003171 A2 | 1/2005 |
| WO | 2005/014024 A2 | 2/2005 |
| WO | 2005/014035 A2 | 2/2005 |
| WO | WO 2005/012484 A2 | 2/2005 |
| WO | WO 2005/025606 A1 | 3/2005 |
| WO | WO 2005/051327 A2 | 6/2005 |
| WO | WO 2005/055946 A2 | 6/2005 |
| WO | WO 2005/055950 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005/072371 A2 | 8/2005 |
| WO | 2005/079363 A2 | 9/2005 |
| WO | WO 2005/091944 A2 | 10/2005 |
| WO | WO 2005/121331 A2 | 12/2005 |
| WO | 2006/005058 A2 | 1/2006 |
| WO | WO 2006/010143 A2 | 1/2006 |
| WO | 2006/013202 A2 | 2/2006 |
| WO | 2006/018204 A1 | 2/2006 |
| WO | WO 2006/011839 A1 | 2/2006 |
| WO | WO 2006/014349 A2 | 2/2006 |
| WO | WO 2006/014466 A2 | 2/2006 |
| WO | WO 2006/020372 A2 | 2/2006 |
| WO | WO 2006/031811 A2 | 3/2006 |
| WO | 2006/035057 A1 | 4/2006 |
| WO | 2006/053299 A2 | 5/2006 |
| WO | WO 2006/050247 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | WO 2006/082517 A1 | 8/2006 |
| WO | 2006/103298 A2 | 10/2006 |
| WO | WO 2006/105426 A2 | 10/2006 |
| WO | WO 2006/119987 A2 | 11/2006 |
| WO | WO 2006/121569 A2 | 11/2006 |
| WO | WO 2006/127910 A2 | 11/2006 |
| WO | 2006/134173 A2 | 12/2006 |
| WO | WO 2007/022512 A2 | 2/2007 |
| WO | WO 2007/056191 A2 | 5/2007 |
| WO | 2007/135182 A2 | 11/2007 |
| WO | WO 2008/011633 A2 | 1/2008 |
| WO | WO 2008/057683 A2 | 5/2008 |
| WO | WO 2008/060780 A2 | 5/2008 |
| WO | WO 2008/073620 A2 | 6/2008 |
| WO | WO 2008/124406 A2 | 10/2008 |
| WO | WO 2008/151258 A2 | 12/2008 |
| WO | WO 2008/154639 A2 | 12/2008 |
| WO | WO 2009/089396 A2 | 7/2009 |

OTHER PUBLICATIONS

Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.
Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,897.
Office Action dated Sep. 28, 2005 in U.S. Appl. No. 10/410,913.
Office Action dated Sep. 28, 2005 in U.S. Appl. No. 10/410,930.
Office Action dated Sep. 28, 2005 in U.S. Appl. No. 10/410,962.
Office Action dated Sep. 28, 2005 in U.S. Appl. No. 10/410,980.
Office Action dated Sep. 28, 2005 in U.S. Appl. No. 10/410,997.
Office Action dated Sep. 28, 2005 in U.S. Appl. No. 10/411,012.
Office Action dated Sep. 28, 2005 in U.S. Appl. No. 10/411,037.
Office Action dated Sep. 28, 2005 in U.S. Appl. No. 10/411,043.
Office Action dated Sep. 28, 2005 in U.S. Appl. No. 10/411,044.

(56) References Cited

OTHER PUBLICATIONS

Office Action dated Sep. 28, 2005 in U.S. Appl. No. 10/411,049.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No. 10/410,897.
Office Action dated Nov. 14, 2005 in U.S. Appl. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.
Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/410,913.
Office Action dated Jan. 26, 2006 in U.S. Appl. No. 10/411,012.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/410,980.
Office Action dated Feb. 7, 2006 in U.S. Appl. No. 10/411,043.
Office Action dated Feb. 7, 2006 in U.S. Appl. No. 10/997,405.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/410,897.
Office Action dated Apr. 4, 2006 in U.S. Appl. No. 10/410,997.
Office Action dated Apr. 4, 2006 in U.S. Appl. No. 10/411,026.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.
Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.
Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in U.S. Appl. No. 09/855,320.
Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283.
Office Action dated Aug. 17, 2007 in U.S. Appl. No. 10/492,261.
Office Action dated Aug. 30, 2007 in U.S. Appl. No. 10/497,284.
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.
Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.
Office Action dated Nov. 15, 2007 in U.S. Appl. No. 11/166,404.
Office Action dated Nov. 28, 2007 in U.S. Appl. No. 11/102,497.
Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 11/402,105.
Office Action dated Dec. 28, 2007 in U.S. Appl. No. 10/565,331.
Office Action dated Jan. 3, 2008 in U.S. Appl. No. 10/549,528.
Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.
Office Action dated Mar. 3, 2008 in U.S. Appl. No. 11/166,404.
Office Action dated Mar. 4, 2008 in U.S. Appl. No. 09/855,320.
Office Action dated Mar. 7, 2008 in U.S. Appl. No. 11/580,669.
Office Action dated Mar. 10, 2008 in U.S. Appl. No. 10/497,284.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.
Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. Appl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.
Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.

(56) References Cited

OTHER PUBLICATIONS

Office Action dated Sep. 23, 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/645,839.
Office Action dated Sep. 29, 2009 in U.S. Appl. No. 11/714,874.
Office Action dated Oct. 2, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/549,528.
Office Action dated Oct. 14, 2009 in U.S. Appl. No. 10/565,331.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4, 2009 in U.S. Appl. No. 10/549,445.
Office Action dated Nov. 20, 2009 in U.S. Appl. No. 11/580,669.
Office Action dated Nov. 24, 2009 in U.S. Appl. No. 11/781,888.
Office Action dated Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/584,743.
Office Action dated Feb. 5, 2010 in U.S. Appl. No. 11/657,441.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.
Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.
Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/664,199.
Office Action dated Jul. 15, 2010 in U.S. Appl. No. 11/701,949.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.
Office Action dated Oct. 1, 2010 in U.S. Appl. No. 11/597,258.
Office Action dated Oct. 1, 2010 in U.S. Appl. No. 11/644,014.
Office Action dated Oct. 1, 2010 in U.S. Appl. No. 11/910,958.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.
Office Action dated Oct. 14, 2010 in U.S. Appl. No. 11/781,885.
Office Action dated Oct. 15, 2010 in U.S. Appl. No. 11/664,199.
Office Action dated Oct. 15, 2010 in U.S. Appl. No. 11/781,888.
Office Action dated Nov. 24, 2010 in U.S. Appl. No. 11/866,969.
Office Action dated Nov. 26, 2010 in U.S. Appl. No. 11/981,483.
Office Action dated Dec. 16, 2010 in U.S. Appl. No. 10/579,620.
Office Action dated Dec. 16, 2010 in U.S. Appl. No. 11/701,949.
Office Action dated Dec. 17, 2010 in U.S. Appl. No. 11/658,218.
Office Action dated Dec. 21, 2010 in U.S. Appl. No. 11/632,005.
Office Action dated Dec. 27, 2010 in U.S. Appl. No. 11/144,223.
Office Action dated Jan. 10, 2011 in U.S. Appl. No. 11/659,942.
Office Action dated Jan. 18, 2011 in U.S. Appl. No. 12/444,380.
Office Action dated Jan. 20, 2011 in U.S. Appl. No. 10/586,166.
Office Action dated Jan. 21, 2011 in U.S. Appl. No. 11/843,588.
Office Action dated Feb. 1, 2011 in U.S. Appl. No. 11/867,553.
Office Action dated Feb. 3, 2011 in U.S. Appl. No. 11/794,555.
Office Action dated Feb. 3, 2011 in U.S. Appl. No. 11/914,104.
Office Action dated Feb. 3, 2011 in U.S. Appl. No. 12/443,428.
Office Action dated Feb. 4, 2011 in U.S. Appl. No. 11/794,560.
Office Action dated Feb. 15, 2011 in U.S. Appl. No. 12/496,595.
Office Action dated Feb. 22, 2011 in U.S. Appl. No. 12/820,926.
Office Action dated Feb. 23, 2011 in U.S. Appl. No. 12/092,563.
Office Action dated Mar. 2, 2011 in U.S. Appl. No. 12/201,705.
Office Action dated Mar. 11, 2011 in U.S. Appl. No. 11/982,273.
Office Action dated Mar. 16, 2011 in U.S. Appl. No. 11/665,908.
Office Action dated Mar. 17, 2011 in U.S. Appl. No. 11/597,258.
Office Action dated May 31, 2011 in U.S. Appl. No. 11/144,223.
Office Action dated Jun. 9, 2011 in U.S. Appl. No. 11/597,258.
Office Action dated Jul. 8, 2011 in U.S. Appl. No. 11/632,005.
Office Action dated Jul. 21, 2011 in U.S. Appl. No. 11/665,908.
Office Action dated Aug. 17, 2011 in U.S. Appl. No. 11/632,005.
Office Action dated Aug. 22, 2011 in U.S. Appl. No. 11/659,942.
Office Action dated Sep. 22, 2011 in U.S. Appl. No. 12/820,926.
Office Action dated Oct. 6, 2011 in U.S. Appl. No. 12/663,748.
Office Action dated Nov. 2, 2011 in U.S. Appl. No. 12/201,705.
Office Action dated Nov. 17, 2011 in U.S. Appl. No. 12/443,428.
Office Action dated Dec. 1, 2011 in U.S. Appl. No. 11/794,560.
Office Action dated Dec. 22, 2011 in U.S. Appl. No. 12/858,247.
Office Action dated Jan. 3, 2012 in U.S. Appl. No. 11/632,005.
Abeijon et al., *J. Biol. Chem.*, 261(24): 11374-11377 (1986).
Abuchowski et al., *J. Biol. Chem.*, 252(11): 3578-3581 (1977).
Abuchowski et al., *J. Biol. Chem.*, 252(11): 3582-3586 (1977).
Abuchowski et al., *Cancer Biochem. Biophys.*, 7(2): 175-186 (1984).
Adelhorst et al., *J. Biol. Chem.*, 269(9): 6275-6278 (1994).
Ailor et al., *Glycobiology*, 10(8): 837-847 (2000).
Alam et al., *J. Biotechnol.*, 65(2-3): 183-190 (1998).
Allegre et al., *J. Memb. Sci.*, 269(1-2): 109-117 (2006).
Altmann et al., *Glycoconj. J.*, 16(2): 109-123 (1999).
Amersham Pharmacia Biotech, "Hydrophobic Interaction Chromatography: Principles and Methods," 104 pp. (2000).
Aplin et al., *CRC Crit. Rev. Biochem.*, 10(4): 259-306 (1981).
Barrios et al., *J. Mol. Recognit.*, 17(4):332-338 (2004).
Beauchamp et al., *Anal. Biochem.*, 131(1): 25-33 (1983).
Bedard et al., *Cytotechnology*, 15(1-3):129-138 (1994).
Bennett et al., *J. Biol. Chem.*, 273(46): 30472-30481 (1998).
Bennett et al., *FEBS Lett.*, 460(2): 226-230 (1999).
Berger et al., *Blood*, 71(6): 1641-1647 (1988).
Berg-Fussman et al., *J. Biol. Chem.*, 268(20): 14861-14866 (1993).
Bhadra et al., *Pharmazie*, 57(1): 5-29 (2002).
Bhatia et al., *Anal. Biochem.*, 178(2): 408-413 (1989).
Bickel et al., *Adv. Drug Deliv. Rev.*, 46(1-3): 247-279 (2001).
Bijsterbosch et al., *Eur. J. Biochem.*, 237(2): 344-349 (1996).
Bjoern et al., *J. Biol. Chem.*, 266(17): 11051-11057 (1991).
Boccu et al., *Z. Naturforsch.*, 38c: 94-99 (1983).

(56) References Cited

OTHER PUBLICATIONS

Boime et al., *Recent Prog. Horm. Res.*, 54: 271-289 (1999).
Boissel et al., *J. Biol. Chem.*, 268(21): 15983-15993 (1993).
Bork et al., *Trends Genet.*, 12(10): 425-427 (1996).
Bork, *Genome Res.*, 10(4): 398-400 (2000).
Bouizar et al., *Eur. J. Biochem.*, 155(1): 141-147 (1986).
Boyd et al., *Mol. Immunol.*, 32(17-18): 1311-1318 (1995).
Brenner, *Trends Genet.*, 15(4): 132-133 (1999).
Brockhausen et al., *Acta Anatomica*, 161: 36-78 (1998).
Brockhausen et al., *Glycoconj. J.*, 15: 595-603 (1998).
Broun et al., *Science*, 282(5392): 1315-1317 (1998).
Browning et al., *J. Immunol.*, 143(6): 1859-1867 (1989).
Brumeanu et al., *J. Immunol. Meth.*, 183: 185-197 (1995).
Bückmann et al., *Makromol. Chem.*, 182(5): 1379-1384 (1981).
Burns et al., *Blood*, 99(12): 4400-4405 (2002).
Butnev et al., *Biol. Reprod.*, 58(2): 458-469 (1998).
Byun et al., *ASAIO J.*, 38(3): M649-M653 (1992).
Casares et al., *Nat. Biotechnol.*, 19(2): 142-147 (2001).
Chaffee et al., *J. Clin. Invest.*, 89(5): 1643-1651 (1992).
Charter et al., *Glycobiology*, 10(10): 1049-1056 (2000).
Chern et al., *Eur. J. Biochem.*, 202(2): 225-229 (1991).
Chiba et al., *Biochem. J.*, 308(2): 405-409 (1995).
Chrisey et al., *Nucleic Acids Res.*, 24(15): 3031-3039 (1996).
Clark et al., *J. Biol. Chem.*, 271(36): 21969-21977 (1996).
Cohn et al., *J. Biomed. Mater. Res,*. 22(11): 993-1009 (1988).
Cointe et al., *Glycobiology*, 10(5): 511-519 (2000).
Conradt et al., *J. Biol. Chem.*, 262(30): 14600-14605 (1987).
Cope et al., *Mol. Microbiol.*, 5(5): 1113-1124 (1991).
Copeland, "Enzymes: A Practical Introduction to Structure, Mechanism and Data Analysis" 2nd ed., Wiley-VCH, New York, pp. 146-150 (2000).
Costa et al., *J. Biol. Chem.*, 272(17): 11613-11621 (1997).
Crout et al., *Curr. Opin. Chem. Biol.*, 2(1): 98-111 (1998).
Culajay et al., *Biochem.*, 39: 7153-7158 (2000).
Deacon, *Diabetes*, 54: 2181-2189 (2004).
Delgado et al., *Biotechnol. Appl. Biochem.*, 12(2): 119-128 (1990).
Delgado et al., *Crit. Rev. Ther. Drug Carrier Syst.*, 9(3-4): 249-304 (1992).
De Vries et al, *J. Biol. Chem.*, 270(15): 8712-8722 (1995).
De Vries et al., *Glycobiology*, 7(7): 921-927 (1997).
Dinter et al., *Biotechnol. Lett.*, 22(1): 25-30 (2000).
Doerks et al., *Trends Genet.*, 14(6): 248-250 (1998).
Douglas et al., *J. Am. Chem. Soc.*, 113(13): 5095-5097 (1991).
Dubé et al., *J. Biol. Chem.*, 263(33): 17516-17521 (1988).
Dumas et al., *Bioorg. Med. Chem. Lett.*, 1(8): 425-428 (1991).
Dunn, 1991, "Polymeric Drugs and Drug Delivery Systems" Dunn et al. (eds.), Chapter 2 "Polymeric Matrices", pp. 11-23, ACS Symposium Series vol. 469, American Chemical Society, Washington D.C.
Durieux et al., *Tetrahedron Lett.*, 42(12): 2297-2299 (2001).
Dwek et al., *J. Anat.*, 187(Pt. 2): 279-292 (1995).
Eavarone et al., *J. Biomed. Mater. Res.*, 51(1): 10-14 (2000).
Edge et al., *Anal. Biochem.*, 118(1): 131-137 (1981).
Elhalabi et al., *Curr. Med. Chem.*, 6(2): 93-116 (1999).
Espuelas et al., *Bioorg. Med. Chem. Lett.*, 13(15): 2557-2560 (2003).
Fairhall et al., *Endocrinology*, 131(4): 1963-1969 (1992).
Fan et al., *J. Biol. Chem.*, 272(43): 27058-27064 (1997).
Feldman et al., *Proc. Natl. Acad. Sci. USA*, 102(8): 3016-3021 (2005).
Felix et al., *J. Peptide Res.*, 63: 85-90 (2004).
Fibi et al., *Blood*, 85(5): 1229-1236 (1995).
Fischer et al., *Thromb. Res.*, 89(3): 147-150 (1998).
Flynn et al., *Curr. Opin. Oncol.*, 12(6): 574-581 (2000).
Francis et al., *Intl. J. Hematol.*, 68(1): 1-18 (1998).
Fritz et al., *Proc. Natl. Acad. Sci. USA*, 101(43): 15307-15312 (2004).
Fritz et al., *J. Biol. Chem.*, 281(13): 8613-8619 (2006).
Garnett et al., *Adv. Drug Deliv. Rev.*, 53(2): 171-216 (2002).
Gatot et al., *J. Biol. Chem.*, 273(21): 12870-12880 (1998).
Ge et al., *J. Biol. Chem.*, 272(34): 21357-21363 (1997).
Gervais et al., *Glycobiology*, 13(3): 179-189 (2003).
Gilbert et al., *Cytotechnology*, 22(1-3): 211-216 (1996).
Gillis et al., *Behring Inst. Mitt.*, 83: 1-7 (1988).
Ginns, PEG Glucocerebrosidase, Internet page from www.gaucher.org.uk/peg2.prg, Nov. 1994, printed Jun. 21, 2002.
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).
Gotschlich, *J. Exp. Med.*, 180(6): 2181-2190 (1994).
Grabenhorst et al., *Eur. J. Biochem.*, 215(1): 189-197 (1993).
Grabenhorst et al., *J. Biol. Chem.*, 274(51): 36107-36116 (1999).
Grodberg et al., *Eur. J. Biochem.*, 218(2): 597-601 (1993).
Gross et al., *Eur. J. Biochem,.* 177(3): 583-589 (1988).
Gross et al., *Biochemistry*, 28(18): 7386-7392 (1989).
Gross, *Eur. J. Biochem.*, 203(1-2): 269-275 (1992).
Guo et al., *Appl. Biochem. Biotechnol.*, 68(1-2): 1-20 (1997).
Hagen et al., *J. Biol. Chem.*, 274(10): 6797-6803 (1999).
Hagen et al., *J. Biol. Chem.*, 276(20): 17395-17404 (2001).
Hall, *Methods Mol. Biol.*, 166: 139-154 (2001).
Hällgren et al., *J. Carb. Chem.*, 14(4-5): 453-464 (1995).
Haneda et al., *Carbohydr. Res.*, 292: 61-70 (1996).
Hang et al., *J. Am. Chem. Soc.*, 123(6): 1242-1243 (2001).
Hansen et al., *Biochem J.*, 308: 801-813 (1995).
Haro et al., *Biochem. Biophys. Res. Comm.*, 228(2): 549-556 (1996).
Harris et al., *Nat. Rev. Drug Discov.*, 2(3): 214-221 (2003).
Harris et al., Abstracts of Papers of the American Chemical Society, V 201, APR, p. 64-POLY, pp. 154-155 (1991).
Harris, *J. Macromol. Science, Rev. Macromol. Chem. Phys.*, C25(3): 325-373 (1985).
Harris (ed.), "Poly(Ethylene Glycol) Chemistry: Biotechnical and Biomedical Applications", Plenum Press, New York (1992) (Title Pages only).
Harris et al. (eds.), "Poly(ethylene glycol): Chemistry and Biological Applications," ACS Symposium Series, vol. 680, American Chemical Society (1997) (Title Pages only).
Hassan et al., *J. Biol. Chem.*, 275(49): 38197-38205 (2000).
Hassan et al., *Carbohydrates in Chemistry and Biology*, Part II, 3: 273-292 (2000).
Hayes et al., *J. Biol. Chem.*, 268(22): 16170-16178 (1993).
Hellstrom et al., *Methods Mol. Biol.*, 166: 3-16 (2001).
Hermanson et al., *Immobilized Affinity Ligand Techniques*, Academic Press (1992) (Table of Contents).
Hermanson, *Bioconjugate Techniques*, Academic Press, San Diego (1996) (Table of Contents).
Hermentin, et al., *Glycobiology*, 6(2): 217-230 (1996).
Herscovics et al., *FASEB J.*, 7(6): 540-550 (1993).
Hills et al., *Am. Biotechnol. Lab.*, 20(11): 30 (2002).
Hink et al., *Biotechnol. Prog.*, 7(1): 9-14 (1991).
Höglund, *Med. Oncol.*, 15(4): 229-233 (1998).
Hollister et al., *Glycobiology*, 11(1): 1-9 (2001).
Hounsell et al., *Glycoconj. J.*, 13(1): 19-26 (1996).
Hu et al., *Mol. Cell. Biol.*, 18(10): 6063-6074 (1998).
Ichikawa et al., *J. Am. Chem. Soc.*, 114(24): 9283-9298 (1992).
Ikonomou et al., *In Vitro Cell. Dev. Biol. Anim.*, 37(9): 549-559 (2001).
Inlow et al., *J. Tissue Cult. Methods*, 12(1): 13-16 (1989).
Inoue et al., *Biotechnol. Annu. Rev.*, 1: 297-313 (1995).
Ito et al., *Pure Appl. Chem.*, 65(4): 753-762 (1993).
Jackson et al., *Anal. Biochem.*, 165(1): 114-127 (1987).
Jarvis et al., *Curr. Opin. Biotechnol.*, 9(5): 528-533 (1998).
Jezek et al., *J. Peptide Sci.*, 5: 46-55 (1999).
Joppich et al., *Makromol. Chem.*, 180: 1381-1384 (1979).
Joshi et al., *J. Biol. Chem.*, 265(24): 14518-14525 (1990).
Jung et al., *Biochim. Biophys. Acta*, 761(2): 152-162 (1983).
Kajihara et al., *Carbohydrate Research*, 315: 137-141 (1999).
Kalsner et al., *Glycoconj. J.*, 12(3): 360-370 (1995).
Kaneko et al., *Cytogenet. Cell Genet.*, 86(3-4): 329-330 (1999).
Kaneko et al., *FEBS Lett.*, 452(3): 237-242 (1999).
Kasina et al., *Bioconjug. Chem.*, 9(1): 108-117 (1998).
Katre et al., *Proc. Natl. Acad. Sci. USA*, 84(6): 1487-1491 (1987).
Kawasaki et al., *Anal. Biochem.*, 285: 82-91 (2000).
Keana et al., *J. Org. Chem.*, 55(11): 3640-3647 (1990).
Keene et al., *J. Biol. Chem.*, 264(9): 4769-4775 (1989).

(56) References Cited

OTHER PUBLICATIONS

Kennedy, "Hydrophobic-Interaction Chromatography," in *Current Protocols in Protein Science*, pp. 8.4.1-8.4.21, Wiley (1995).
Keppler et al., *Glycobiology*, 11(2): 11R-18R (2001).
Kimura et al., *Proc. Natl. Acad. Sci. USA*, 96(8): 4530-4535 (1999).
Kisselev, *Structure*, 10(1): 8-9 (2002).
Kitamura et al., *Biochem. Biophys. Res. Commun.*, 171(3): 1387-1394 (1990).
Kitamura et al., *Cancer Res.*, 51(16): 4310-4315 (1991).
Kobayashi et al., *Eur. J. Nucl. Med.*, 27(9):1334-1339 (2000).
Kodama et al., *Tetrahedron Lett.*, 34(40): 6419-6422 (1993).
Koeller et al., *Nat. Biotechnol.*, 18(8): 835-841 (2000).
Koeller et al., *Nature*, 409(6817): 232-240 (2001).
Koide et al., *Biochem. Biophys. Res. Commun.*, 111(2): 659-667 (1983).
Kornfeld et al., *Ann. Rev. Biochem.*, 54: 631-664 (1985).
Kreitman, *Curr Pharm Biotechnol.*, 2(4): 313-325 (2001).
Krystal et al., *Blood*, 67(1): 71-99 (1986).
Kuhn et al., *J. Biol. Chem.*, 270(49): 29493-29497 (1995).
Kukowska-Latallo et al., *Genes Dev.*, 4(8): 1288-1303 (1990).
Kukuruzinska et al., *Proc. Natl. Acad. Sci. USA*, 84(8): 2145-2149 (1987).
Lai et al, *J. Biol. Chem.*, 261(7): 3116-3121 (1986).
Langer, *Science*, 249(4976): 1527-1533 (1990).
Lau et al., *J. Biotechnol.*, 75(2-3): 105-115 (1999).
Lee et al., *Biochemistry*, 28(4): 1856-1861 (1989).
Lee-Huang et al., *Proc. Natl. Acad. Sci. USA*, 81(9): 2708-2712 (1984).
Legault et al., *J. Biol. Chem.*, 270(36): 20987-20996 (1995).
Leist et al., *Science*, 305: 239-242 (2004).
Leiter et al., *J. Biol. Chem.*, 274(31): 21830-21839 (1999).
Leung, *J Immunol.* 154(11): 5919-5926 (1995).
Lewis et al., *Endocr. J.*, 47(Suppl.): S1-S8 (2000).
Li et al., *Trends Pharmacol. Sci.*, 23(5): 206-209 (2002).
Li et al., *Med. Res. Rev.*, 22(3): 225-250 (2002).
Licari et al., *Biotechnol. Bioeng.*, 39(4): 432-441 (1992).
Licari et al., *Biotechnol. Bioeng.*, 39(9): 932-944 (1992).
Lin et al., *Proc. Natl. Acad. Sci. USA*, 82: 7580-7584 (1985).
Liu et al., *Chem. Eur. J.*, 2(11): 1359-1362 (1996).
Long et al., *Exp. Hematol.*, 34(6): 697-704 (2006).
Lönnberg, *Curr. Org. Synth.*, 6(4): 400-425 (2009).
Lord et al., *Clin. Cancer Res.*, 7(7): 2085-2090 (2001).
Lougheed et al., *J. Biol. Chem.*, 274(53): 37717-37722 (1999).
Luckow et al., *Curr. Opin. Biotechnol.*, 4(5): 564-572 (1993).
Lund et al., *FASEB J.*, 9(1): 115-119 (1995).
Lund et al., *J. Immunol.*, 157(11): 4963-4969 (1996).
Mahal et al., *Science*, 276(5315): 1125-1128 (1997).
Malissard et al., *Biochem. Biophys. Res. Commun.*, 267(1): 169-173 (2000).
Maranga et al., *Biotechnol. Bioeng.*, 84(2): 245-253 (2003).
Maras et al., *J Biotechnol.*, 77(2-3): 255-263 (2000).
Meynial-Salles et al., *J. Biotechnol.*, 46(1): 1-14 (1996).
Miller, *Curr. Opin. Genet. Dev.*, 3(1): 97-101 (1993).
Min et al., *Endocr. J.*, 43(5): 585-593 (1996).
Mistry et al., *Lancet*, 348(9041): 1555-1559 (1996).
Mollicone et al., *Eur. J. Biochem.*, 191(1): 169-176 (1990).
Monaco et al., *Gene*, 180: 145-150 (1996).
Morimoto et al., *Glycoconj. J.*, 13(6): 1013-1020 (1996).
Muller et al., *J. Biol. Chem.*, 272(40): 24780-24793 (1997).
Muller et al., *J. Biol. Chem.*, 274(26): 18165-18172 (1999).
Nagata et al., *EMBO J.*, 5(3): 575-581 (1986).
Natsuka et al., *J. Biol. Chem.*, 269(24): 16789-16794 (1994).
NCBI—Accession No. NCAA26095 (2 pgs.) (2006).
NCBI—Accession No. NP_058697 (3 pgs.) (2007).
NCBI—Accession No. NP_999299 (2 pgs.) (2007).
NCBI Database hits for erythropoietin protein sequences (3 pgs.) (2007).
Ngo et al., "The Protein Folding Problem and Tertiary Structure Prediction, Chapter 14: Computational Complexity Protein Structure Prediction, and the Levinthal Paradox," pp. 433-440 and 492-495 (1994).
Nilsson et al., *Methods Enzymol.*, 104: 56-69 (1984).
Nunez et al., *Can. J. Chem.*, 59(14): 2086-2095 (1981).
O'Connell et al., *J. Biol. Chem.*, 267(35): 25010-25018 (1992).
Oetke et al., *J. Biol. Chem.*, 277(8): 6688-6695 (2002).
Oh-Eda et al., *J. Biol. Chem.*, 265: 11432-11435 (1990).
Olson et al., *J. Biol. Chem.*, 274(42): 29889-29896 (1999).
Orlean, "vol. III: The Molecular and Cellular Biology of the Yeast *Saccharomyces*: Cell Cycle and Cell Biology", in *Biogenesis of Yeast Wall and Surface Components*, Chapter 3, pp. 229-362, Cold Spring Harbor Laboratory Press (1997).
Orskov et al., *J. Biol. Chem.*, 264(22): 12826-12829 (1989).
O'Shannessy et al., *J. Appl. Biochem.*, 7: 347-355 (1985).
Palacpac et al., *Proc. Natl. Acad. Sci. USA*, 96(8): 4692-4697 (1999).
Palcic et al., *Carbohydr. Res.*, 190(1): 1-11 (1989).
Park et al., *J. Biol. Chem.*, 261(1): 205-210 (1986).
Paulson et al., *J. Biol. Chem.*, 252(23): 8624-8628 (1977).
Plummer et al., *J. Biol. Chem.*, 270(22): 13192-13196 (1995).
PNGase-F Amidase Sequence from F. Meningosepticum (RN 128688-70-0) (2007).
PNGase-F Amidase Sequence from F. Meningosepticum (RN 128688-71-1) (2007).
Prati et al., *Biotech and Bioeng.*, 79(5): 580-585 (2002).
Prieels et al., *J. Biol. Chem.*, 256(20): 10456-10463 (1981).
Pyatak et al., *Res. Commun. Chem. Pathol. Pharmacol.*, 29(1): 113-127 (1980).
Quelle et al., *Blood*, 74(2): 652-657 (1989).
Rabouille et al., *J Cell Sci.*, 112(Pt. 19): 3319-3330 (1999).
Rasko et al., *J. Biol. Chem.*, 275(7): 4988-4994 (2000).
R & D Systems, Fibroblast Growth Factors (FGFs), Internet page from www.rndsystems.com/mini_review_detail_objectname_MR01_FGFs.aspx, 2001, printed Mar. 10, 2011.
Rathnam et al., *Biochim. Biophys. Acta*, 624(2): 436-442 (1980).
Reff et al., *Cancer Control*, 9(2): 152-166 (2002).
Rosenthal et al., *Methods Enzymol.*, 235: 253-285 (1994).
Rotondaro et al., *Mol. Biotech.*, 11: 117-128 (1999).
Rudikoff et al., *Proc. Natl. Acad. Sci. USA*, 79(6):1979-1983 (1982).
Sadler et al., *Methods Enzymol.*, 83: 458-514 (1982).
Sandberg et al., *Semin. Hematol.*, 38(2 Suppl. 4): 4-12 (2001).
Saneyoshi et al., *Biol. Reprod.*, 65(6): 1686-1690 (2001).
Sasaki et al., *J. Biol. Chem.*, 262(25): 12059-12076 (1987).
Sasaki et al., *J.Biol. Chem.*, 269(20): 14730-14737 (1994).
Saxon et al., *Science*, 287(5460): 2007-2010 (2000).
Saxon et al., *J. Am. Chem. Soc.*, 124(50): 14893-14902 (2002).
Schlaeger, *Cytotechnology*, 20(1-3): 57-70 (1996).
Schwarz et al., Nucl. Med. Biol., 26(4):383-388 (1999).
Schwientek et al., *Gene*, 145(2): 299-303 (1994).
Schwientek et al., *J. Biol. Chem.*, 277(25): 22623-22638 (2002).
Scouten, *Methods Enzymol.*, 135: 30-65 (1987).
Seely et al., *J. Chromatog.*, 908: 235-241 (2001).
Seffernick et al., *J. Bacteriol.*, 183(8): 2405-2410 (2001).
Seitz, *Chembiochem.*, 1(4): 214-246 (2000).
Shah et al., *J. Pharm. Sci.*, 85(12): 1306-1311 (1996).
Shapiro et al., *Blood*, 105(2): 518-525 (2005).
Shen et al., *Biochem. Biophys. Res. Commun.*, 102(3): 1048-1054 (1981).
Shinkai et al., *Prot. Exp. Purif.*, 10: 379-385 (1997).
Sinclair et al., *J. Pharm. Sci.*, 94: 1626-1635 (2005).
Singh et al., *Chem. Commun.*, 1996(8): 993-994 (1996).
Sinha et al., *Infect. Immun.*, 29(3): 914-925 (1980).
Skolnick et al., *Trends Biotechnol.*, 18(1): 34-39 (2000).
Smith et al., *Nat. Biotechnol.*, 15(12): 1222-1223 (1997).
Snider et al., *J. Chromatogr.*, A 599(1-2): 141-155 (1992).
Sojar et al., *Arch. Biochem. Biophys.*, 259(1): 52-57 (1987).
Song et al., *J. Pharmacol. Exp. Ther.*, 301(2): 605-610 (2002).
Srinivasachar et al., *Biochemistry*, 28(6): 2501-2509 (1989).
Srivastava et al., *J. Biol. Chem.*, 267(31): 22356-22361 (1992).
Staudacher, *Trends Glycosci. Glycotechnol.*, 8(44): 391-408 (1996).
Stemmer, *Nature*, 370(6488): 389-391 (1994).
Stemmer, *Proc. Natl. Acad. Sci. USA*, 91(22): 10747-10751 (1994).

(56) References Cited

OTHER PUBLICATIONS

Stephens et al., *Eur. J. Biochem.*, 133(1): 155-162 (1983).
Stephens et al., *Eur. J. Biochem.*, 133(3): 481-489 (1983).
Stephens et al., *Eur. J. Biochem.*, 135(3): 519-527 (1983).
Strausberg et al., *Proc Natl Acad Sci USA*, 99(26): 16899-16903 (2002).
Takane et al., *J Pharmacol Exp. Ther.*, 294(2): 746-752 (2000).
Takeda et al., *Trends Biochem. Sci.*, 20(9): 367-371 (1995).
Takeuchi et al., *J. Biol. Chem.*, 265(21): 12127-12130 (1990).
Taniguchi et al., *Proteomics*, 1(2): 239-247 (2001).
Tanner et al., *Biochim. Biophys. Acta*, 906(1): 81-99. (1987).
Taylor et al., Protein Immobilization Fundamentals and Applications, Manual (1991).
Ten Hagen et al., *J. Biol. Chem.*, 274(39): 27867-27874 (1999).
Tenno et al., *J. Biol. Chem.*, 277(49): 47088-47096 (2002).
Thotakura et al., *Meth. Enzym.*, 138: 350-9 (1987).
Tom et al., *AAPS Journal*, 9(2): E227-E234 (2007).
Trottein et al., *Mol. Biochem. Parasitol.*, 107(2): 279-287 (2000).
Tsuboi et al., *Arch. Biochem. Biophys.*, 374(1): 100-106 (2000).
Tsunoda et al., *J. Pharmacol. Exp. Ther.*, 209(1): 368-372 (1999).
Tuddenham, *Nature*, 419(6902): 23-24 (2002).
Udenfriend et al., *Annu. Rev. Biochem.*, 64: 563-591 (1995).
Ulloa-Aguirre et al., *Endocrine*, 11(3): 205-215 (1999).
Uludag et al., *Biotechnol. Prog.*, 18(3): 604-611 (2002).
Uptima, Detergents: Solubilization of Biomolecules, Internet page from www.interchim.com/interchim/bio/product_uptima/produits_line/p1p_detergents.htm, 2001, printed Nov. 14, 2011.
Urdal et al., *J. Chromatogr.*, 296: 171-179 (1984).
Van Berkel et al., *Biochem. J.*, 319(Pt. 1): 117-122 (1996).
Van Reis et al., *Biotechnol. Bioeng.*, 38(4): 413-422 (1991).
Van Tetering et al., *FEBS Lett.*, 461(3): 311-314 (1999).
Veronese et al., *Appl. Biochem. Biotechnol.*, 11(2): 141-152 (1985).
Veronese, *Biomaterials*, 22(5): 405-417 (2001).
Vitetta et al., *Science*, 313: 308-309 (2006).
Vocadlo et al., "Glycosidase-Catalysed Oligosaccharide Synthesis" in *Carbohydrate Chemistry and Biology*, vol. 2, Chapter 29, pp. 723-844 (2000).
Vyas et al., *Crit. Rev. Ther. Drug Carrier Syst.*, 18(1): 1-76 (2001).
Wang et al., *Glycobiology*, 6(8): 837-842 (1996).
Wang et al., *Tetrahedron Lett.*, 37(12): 1975-1978 (1996).
Wang et al., *Protein Eng.*, 11(12): 1277-1283 (1998).
Wang et al., *Microbiol.*, 145(Pt. 11): 3245-3253 (1999).
Wellhoner et al., *J. Biol. Chem.*, 266(7): 4309-4314 (1991).
Wells, *Biochemistry*, 29(37): 8509-8517 (1990).
Weston et al., *J. Biol. Chem.*, 267(6): 4152-4160 (1992).
Weston et al., *J. Biol. Chem.*, 267(34): 24575-24584 (1992).
White et al., *J. Biol. Chem.*, 270(41): 24156-24165 (1995).
Wishart et al., *J. Biol. Chem.*, 270(45): 26782-26785 (1995).
Witkowski et al., *Biochemistry*, 38(36): 11643-11650 (1999).
Witte et al., *J. Am. Chem. Soc.*, 119(9): 2114-2118 (1997).
Witte et al., *Cancer and Metastasis Rev.*, 17: 155-161 (1998).
Woghiren et al., *Bioconjug. Chem.*, 4(5): 314-318 (1993).
Wong et al., *J. Org. Chem.*, 47(27): 5416-5418 (1982).
Wong et al., *Enzyme Microb Technol.*, 14(11): 866-874 (1992).
Wong et al., *Biotechnol. Bioeng.*, 49(6): 659-666 (1996).
Woods et al., *Eur. J. Cell Chem.*, 50(1): 132-143 (1989).
Wright et al., *J. Immunol.*, 160(7): 3393-3402 (1998).
Wu et al., *J. Drug Target.*, 10(3): 239-245 (2002).
Xing et al., *Biochem. J.*, 336(Pt. 3): 667-673 (1998).
Yamada et al., *Biochemistry*, 20(17): 4836-4842 (1981).
Yamamoto et al., *Carbohydr. Res.*, 305(3-4): 415-422 (1998).
Yarema et al., *J. Biol. Chem.*, 273(47): 31168-31179 (1998).
Yin et al., *Pharm. Res.*, 21(12): 2377-2383 (2004).
Yoshida et al., *Glycobiology*, 9(1): 53-58 (1999).
Yoshitake et al., *Biochemistry*, 24(14): 3736-3750 (1985).
Younes et al., *J. Biomed. Mater. Res.*, 21(11): 1301-1316 (1987).
Zalipsky et al., "Use of Functionalized Poly(Ethylene Glycol)s for Modification of Polypeptides" in *Poly(Ethylene Glycol) Chemistry: Biotechnical and Biomedical Applications*, Harris (ed.), Chapter 21, pp. 347-370 (Plenum Press, New York, 1992).
Zalipsky, *Bioconjug. Chem.*, 6(2): 150-165 (1995).
Zarling et al., *J. Immunol.*, 124(2): 913-920 (1980).
Zhang et al., *Biochim. Biophys. Acta*, 1425: 441-452 (1998).
Zheng et al., *Biotechnol. Bioeng.*, 65(5): 600-604 (1999).
Zhou et al., 1994, *Mol. Microbiol.*, 14(4): 609-618 (1994).
Office Action dated Feb. 29, 2012 in U.S. Appl. No. 12/858,247.
Office Action dated Mar. 21, 2012 in U.S. Appl. No. 11/794,560.
Office Action dated Mar. 29, 2012 in U.S. Appl. No. 12/594,326.
Office Action dated Apr. 18, 2012 in U.S. Appl. No. 12/663,748.
Office Action dated Apr. 19, 2012 in U.S. Appl. No. 13/215,439.
Arslan et al., *Transf. Apher. Sci.*, 37: 179-185 (2007).
Cantin et al., *Am. J. Respir. Cell Mol. Biol.*, 27(6): 659-665 (2002).
Capoccia et al., *Blood*, 108(7): 2438-2445 (2006).
Cashen et al., *Bone Marrow Trans.*, 39: 577-588 (2007).
Flomenberg et al., *Blood*, 106(5): 1867-1874 (2005).
GE Healthcare, "Ion Exchange Chromatography & Chromatofocusing: Principles and Methods," Edition AA, Amersham Biosciences, pp. 7, 11-12, 16-17, 21-23, 26-36, 41, 89, 156, 160, 161 (2004).
Hill et al., *Biol. Blood Marrow Trans.*, 12: 603-607 (2006).
Nobel et al., *Ann. Hematol.*, 82: 207-213 (2003).
Kroschinsky et al., *Trans. Apher. Sci.*, 38: 237-244 (2008).
Liles et al., *Transfusion*, 45: 295-300 (2005).
Office Action dated Aug. 8, 2012 in U.S. Appl. No. 13/157,575.
Office Action dated Aug. 17, 2012 in U.S. Appl. No. 12/594,326.
Office Action dated Sep. 21, 2012 in U.S. Appl. No. 12/663,748.
Office Action dated Sep. 24, 2012 in U.S. Appl. No. 12/784,323.
Office Action dated Sep. 25, 2012 in U.S. Appl. No. 13/186,726.
Office Action dated Oct. 23, 2012 in U.S. Appl. No. 12/811,963.
Office Action dated Nov. 9, 2012 in U.S. Appl. No. 12/663,056.
Office Action dated Nov. 26, 2012 in U.S. Appl. No. 13/215,439.
Office Action dated Dec. 21, 2012 in U.S. Appl. No. 13/246,512.
Asano et al., "Phase I Clinical Study for Recombinant Human Granulocyte Colony-Stimulating Factor," *Behring Inst. Mitt.*, 83: 222-228 (1988).
Drucker et al., "Glucagon Gene Expression in Vertebrate Brain," *J. Biol. Chem.*, 263(27): 13475-13478 (1988).
Klingemann, "Clinical Applications of Recombinant Human Colony-Stimulating Factors," *CMAJ*, 140: 137-150 (1989).
Monfardini et al., "A Branched Monomethoxypoly (ethylene glycol) for Protein Modification," *Bioconjug. Chem.*, 6(1): 62-69 (1995).
Morstyn et al., "Clinical Experience With Recombinant Human Granulocyte Colony-Stimulating Factor and Granulocyte Macrophage Colony-Stimulating Factor," *Seminars in Hematology*, 26(2)(Suppl 2): 9-13 (1989).
Moscatelli et al., "Enzymatic Properties of a β-Glucanase from *Bacillus subtilis*," *J. Biol. Chem.*, 236(11): 2858-2862 (1961).
Negrin et al., "Treatment of Myelodysplastic Syndromes with Recombinant Human Granulocyte Colony-Stimulating Factor," *Annals of Internal Medicine*, 110(12): 976-984 (1989).
Perrin et al., "Common Physical Techniques Used in Purification," in *Purification of Laboratory Chemicals*, pp. 30-31, Pergamon (1980).
Rabina et al., "Analysis of Nucleotide Sugars from Cell Lysates by Ion-Pair Solid-Phase Extraction and Reversed-Phase High-Performance Liquid Chromatography," *Glycoconj. J.*, 18(10): 799-805 (2001).
Song et al., "Reassembled Biosynthetic Pathway for a Large-Scale Synthesis of CMP-Neu5Ac," *Mar. Drugs*, 1: 34-45 (2003).
Yoshida et al., "Effect of Granulocyte Colony-Stimulating Factor on Neutropenia Due to Chemotherapy for Non-Hodgkin's Lymphoma," *Cancer*, 66(9): 1904-1909 (1990).
Office Action dated Jan. 17, 2013 in U.S. Appl. No. 13/541,185.
Office Action dated Mar. 6, 2013 in U.S. Appl. No. 13/157,575.
Office Action dated Mar. 13, 2013 in U.S. Appl. No. 12/811,963.
Office Action dated Mar. 14, 2013 in U.S. Appl. No. 12/784,323.
Office Action dated Mar. 21, 2013 in U.S. Appl. No. 13/541,185.
Office Action dated May 9, 2013 in U.S. Appl. No. 12/594,326.
Office Action dated May 21, 2013 in U.S. Appl. No. 12/811,963.
Office Action dated Jun. 6, 2013 in U.S. Appl. No. 11/701,949.
Office Action dated Jul. 11, 2013 in U.S. Appl. No. 11/652,467.
Office Action dated Jul. 17, 2013 in U.S. Appl. No. 13/215,439.
Office Action dated Jul. 30, 2013 in U.S. Appl. No. 13/246,512.
Office Action dated Aug. 12, 2013 in U.S. Appl. No. 13/541,185.
Office Action dated Sep. 6, 2013 in U.S. Appl. No. 12/784,323.

(56) References Cited

OTHER PUBLICATIONS

Office Action dated Sep. 16, 2013 in U.S. Appl. No. 11/781,885.
Office Action dated Sep. 17, 2013 in U.S. Appl. No. 11/781,888.
Office Action dated Sep. 25, 2013 in U.S. Appl. No. 12/663,748.
Office Action dated Oct. 10, 2013 in U.S. Appl. No. 10/581,538.
Office Action dated Oct. 16, 2013 in U.S. Appl. No. 11/597,258.
Office Action dated Nov. 7, 2013 in U.S. Appl. No. 12/811,963.
Ajisaka et al., *Biosci. Biotechnol. Biochem.*, 65(5): 1240-1243 (2001).
Andree et al., *Biochim. Biophys. Acta*, 544(3): 489-495 (1978).
Apicella et al., *Infect. Immun.*, 55(8): 1755-1761 (1987).
Arsequell et al., *Tetrahedron: Asymmetry*, 10(16): 3045-3094 (1999).
ATCC Catalog of Bacteria and Bacteriophages, 17th ed., p. 150-151 (1989).
Auge et al., *Carbohydr. Res.*, 151: 147-156 (1986).
Auge et al., *Carbohydr. Res.*, 200: 257-268 (1990).
Avigad et al., *J. Biol. Chem.*, 237(9): 2736-2743 (1962).
Barker et al., *J. Biol. Chem.*, 247(22): 7135-7147 (1972).
Bayer et al., *Glycobiology*, 13(11): 890-891 (2003).
Bertozzi et al., *J. Am. Chem. Soc.*, 114(26): 10639-10641 (1992).
Biemann et al., *Science*, 237(4818): 992-998 (1987).
Binder et al., *Tetrahedron*, 50(35): 10407-10418 (1994).
Bishop et al., *Endocrinology*, 136(6): 2635-2640 (1995).
Bocci, *Adv. Drug Deliv. Rev.*, 4(2): 149-169 (1989).
Borman, *Chem. Eng. News*, 84(36): 13-22 (2006).
Breton et al., *Curr. Opin. Struct. Biol.*, 9(5): 563-571 (1999).
Breton et al., *Biochimie*, 83(8): 713-718 (2001).
Brinkman-Van Der Linden et al., *J. Biol. Chem.*, 271(24): 14492-14495 (1996).
Broquet et al., *Eur. J. Biochem.*, 123(1): 9-13 (1982).
Burczak et al., *Biochim. Biophys. Acta*, 804(4): 442-449 (1984).
Burns et al., *J. Org. Chem.*, 56(8): 2648-2650 (1991).
Calvet, *Pediatr. Nephrol.*, 5(6): 751-757 (1991).
Carlson et al., *J. Biol. Chem.*, 248(16): 5742-5750 (1973).
Chang et al., *Biotechnol. Bioprocess Eng.*, 3(1): 40-43 (1998).
Chang et al., *Biochemistry*, 38(34): 10940-10948 (1999).
Clogston et al., *J. Chromatogr. A*, 637(1): 55-62 (1993).
Corfield, "Analysis of Sugar Sequences in Glycoproteins by Glycosidase Digestion and Gel Filtration," *Methods in Molecular Biology*, 19: 269-286 (1993).
Dabkowski et al., *Transplant Proc.*, 25(5): 2921 (1993).
Danaher et al., *J. Bacteriol.*, 177(24): 7275-7279 (1995).
Datta et al., *J. Biol. Chem.*, 270(4): 1497-1500 (1995).
David et al., *Pure Appl. Chem.*, 59(11): 1501-1508 (1987).
Davis et al., *Synlett* 1999, (9): 1495-1507 (1999).
De Rosa et al., *Phytochemistry*, 42(4): 1031-1034 (1996).
Deangelis et al., *Biochemistry*, 33(31): 9033-9039 (1994).
Deluca et al., *J. Am. Chem. Soc.*, 117(21): 5869-5870 (1995).
Dennis et al., *J. Biol. Chem.*, 277(38): 35035-35043 (2002).
Dickinson et al., *Proc. Natl. Acad. Sci. USA*, 93(25): 14379-14384 (1996).
Dreyfus et al., *Anal. Biochem.*, 249(1): 67-78 (1997).
Dudas et al., *Infect. Immun.*, 56(2): 499-504 (1988).
Dudziak et al., *Tetrahedron*, 56(32): 5865-5869 (2000).
Edano et al., *Biol. Pharm. Bull.*, 21(4): 382-385 (1998).
Ellis, "Vaccines" Plotkin et al. (eds.), Chapter 29, W.B. Saunders Co., Philadelphia, pp. 568-575 (1988).
EMBL Accession No. M80599 and M86935 (Jan. 23, 1992).
EMBL Accession No. S56361 (May 4, 1993).
EMBL Accession No. 000039 (Jun. 2, 1994).
Ernst et al., *Glycoconj. J.*, 16(2): 161-170 (1999).
Fu et al., *Bioconjug. Chem.*, 12(2): 271-279 (2001).
Fujita et al., *Biochim. Biophys. Acta*, 1528(1): 9-14 (2001).
GE Healthcare, Instructions 28/9064-05 AA (2006).
GE Healthcare, Instructions 28/9064-05 AC (2006).
Genbank Accession No. AAA98726, "Factor IX," pp. 1-3 (Apr. 14, 2009).
Genbank Accession No. CAA01607, "Factor IX of Homo sapiens," pp. 1-2 (Apr. 14, 2009).
Genbank Accession No. D49915 (Sep. 1, 1995).
Genbank Accession No. U02304 (Mar. 8, 1994).
Genbank Accession No. U18918 (Oct. 1, 1995).
Gibson et al., *J. Bacteriol.*, 175(9): 2702-2712 (1993).
Gilbert, "Methods in Enzymology" Packer (ed.), 2(251): 8-28, Biothiols Part A, Elsevier (1995).
Gilbert et al., "The Synthesis of Sialylated Oligosaccharides Using a CMP-Neu5Ac Synthetase/Sialyltransferase Fusion," *Nature Biotechnology*, 16: 769-772 (1998).
Gillespie et al., FASEB Journal, 4(7): A2068 [Abstract No. 2173] (1990).
Gillespie et al., *J. Biol. Chem.*, 267(29): 21004-21010 (1992).
Goodson et al., *Biotechnology (N.Y.)*, 8(4): 343-346 (1990).
Greenwell et al., *Blood Group a Synthesising Activity of the Blood Group B Gene Specified .alpha.-3-D-Galactosyl Transferase*, p. 268-269 (1979).
Greenwell et al., *Carbohydr. Res.*, 149(1): 149-170 (1986).
Gross et al., *Eur. J. Biochem.*, 168(3): 595-602 (1987).
Grundmann et al., *Nucleic Acids Res.*, 18(3): 667 (1990).
Gu et al., *FEBS Lett.*, 275(1-2): 83-86 (1990).
Guivisdalsky et al., *J. Med. Chem.*, 33(9): 2614-2621 (1990).
Hakomori et al., "Methods in Enzymology," Fleischer et al. (eds.), 33(32): 345-367, Biomembranes Part B, Elsevier USA (1974).
Hedner et al., "Recombinant Activated Factor VII in the Treatment of Bleeding Episodes in Patients With Inherited and Acquired Bleeding Disorders," *Transfusion Medicine Reviews*, VII(2): 78-83 (1993).
Heimgartner et al., "Reversible and Irreversible Cross-Linking of Immunoglobulin Heavy Chains Through Their Carbohydrate Residues," *Biochem. J.*, 267: 585-591 (1990).
Helling et al., *Cancer Res.*, 54(1): 197-203 (1994).
Higa et al., *J. Biol. Chem.*, 260(15): 8838-8849 (1985).
Higashi et al., *J. Biol. Chem.*, 272(41): 25724-25730 (1997).
High et al., *Mol. Microbiol.*, 9(6): 1275-1282 (1993).
Hoffman et al., *Thromb. Haemost.*, 85(6): 958-965 (2001).
Ichikawa et al., *J. Am. Chem. Soc.*, 113(12): 4698-4700 (1991).
Ichikawa et al., *J. Am. Chem. Soc.*, 113(16): 6300-6302 (1991).
Ito et al., *J. Am. Chem. Soc.*, 115(4): 1603-1605 (1993).
Japanese Biochemical Society, "New Course in Biochemistry Experiments 3, Sugars I, Glycoproteins (top)," Tokyo Kagaku Dojin K.K., First Edition, p. 340 (1990) English Translation.
Jennemann et al., *J. Biochem.*, 115(6): 1047-1052 (1994).
Jennings et al., *Mol. Microbiol.*, 10(2): 361-369 (1993).
John et al., *J. Biol. Chem.*, 266(29): 19303-19311 (1991).
Jonsson et al., *EMBO J.*, 10(2): 477-488 (1991).
Joziasse et al., *J. Biol. Chem.*, 260(8): 4941-4951 (1985).
Joziasse et al., *J. Biol. Chem.*, 264(24): 14290-14297 (1989).
Kawai et al., *J. Lipid Res.*, 26(3): 338-343 (1985).
Kerwood et al., *Biochemistry*, 31(51): 12760-12768 (1992).
Khidekel et al., *J. Am. Chem. Soc.*, 125(52): 16162-16163 (2003).
Kitagawa et al., *Biochem. Biophys. Res. Commun.*, 194(1): 375-382 (1993).
Kitagawa et al., *J. Biol. Chem.*, 269(27): 17872-17878 (1994).
Knight et al., *Mol. Microbiol.*, 6(11): 1565-1573 (1992).
Koeller et al., "Complex Carbohydrate Synthesis Tools for Glycobiologists: Enzyme-Based Approach and Programmable One-Pot Strategies," *Glycobiology*, 10(11): 1157-1169 (2000).
Kogan, *Synth. Commun.*, 22(16): 2417-2424 (1992).
Koike et al., *Carbohydr. Res.*, 162(2): 237-246 (1987).
Kurosawa et al., *Eur. J. Biochem.*, 219(1-2): 375-381 (1994).
Larsen et al, *Proc. Natl. Acad. Sci. USA*, 86(21): 8227-8231 (1989).
Lee et al., *Science*, 239(4845): 1288-1291 (1988).
Lidholt et al, *Biochem. J.*, 261(3): 999-1007 (1989).
Livingston et al., *J. Biol. Chem.*, 268(16): 11504-11507 (1993).
Lundstrom-Ljung et al., *J. Biol. Chem.*, 270(14): 7822-7828 (1995).
Luo et al., "Spontaneous Calcification of Arteries and Cartilage in Mice Lacking Matrix GLA Protein," *Nature*, 386: 78-81 (1997).
Maccioni et al., *Biochim Biophys Acta.*, 1437(2): 101-118 (1999).
Mackenzie et al., *J. Am. Chem. Soc.*, 120(22): 5583-5584 (1998).
Madnick et al., *Arch. Biochem. Biophys.*, 212(2): 432-442 (1981).
Mandrell et al., *J. Exp. Med.*, 168(1): 107-126 (1988).
Mandrell et al., *J. Exp. Med.*, 171(5): 1649-1664 (1990).
Mandrell et al., *J. Bacteriol.*, 173(9): 2823-2832 (1991).
Mandrell, *Infect. Immun.*, 60(7): 3017-3020 (1992).

(56) References Cited

OTHER PUBLICATIONS

Manfioletti et al., "The Protein Encoded by a Growth Arrest-Specific Gene (*gas6*) Is a New Member of the Vitamin K-Dependent Proteins Related to Protein S, a Negative Coregulator in the Blood Coagulation Cascade," *Mol. Cell. Bio.*, 13(8): 4976-4985 (1993).
Marinier et al., *J. Med. Chem.*, 40(20): 3234-3247 (1997).
Mathews et al., *J. Biol. Chem.*, 262(16): 7537-7545 (1987).
Mizuguchi et al., *Thromb. Haemost.*, Abstract 1474: 466, Suppl. (Aug. 1999).
Muramatsu et al., *Comprehensive Research on Clinical Organ Xenotransplantation by Genetic Regulation*, p. 10-12. (1997) English Translation.
Nelsestuen et al., "Vitamin K-Dependent Proteins," *Vitamins and Hormones*, 58: 355-389 (2000).
Nemansky et al., *FEBS Lett.*, 312(1): 31-36 (1992).
Nilsson, *Trends Biotechnol.*, 6(10): 256-264 (1988).
Nucci et al., *Adv. Drug Deliv. Rev.*, 6(2): 133-151 (1991).
Nunez et al., *Biochemistry*, 15(17): 3843-3847 (1976).
Palcic et al., *Glycobiology*, 1(2): 205-209 (1991).
Parsons et al., *Microb. Pathog.*, 7(1): 63-72 (1989).
Patra et al., *Protein Expr. Purif.*, 18(2): 182-192 (2000).
Paulson et al., *Chemical Abstracts*, 86(25): 213 [Abstract No. 185016b] (1977).
Paulson et al., *J. Biol. Chem.*, 252(7): 2356-2362 (1977).
Paulson et al., *J. Biol. Chem.*, 264(19):10931-10934 (1989).
Pfaffli et al., *Carbohydr. Res.*, 23(2): 195-206 (1972).
Pradel et al., *J. Bacteriol.*, 174(14): 4736-4745 (1992).
Preuss et al., *J. Biol. Chem.*, 268(35): 26273-26278 (1993).
Probert et al., *Tetrahedron Lett.*, 38(33): 5861-5864 (1997).
Raju et al., "Glycoengineering of Therapeutic Glycoproteins: In Vitro Galactosylation and Sialylation of Glycoproteins with Terminal *N*-Acetylglucosamine and Galactose Residues," *Biochemistry*, 40(30): 8868-8876 (2001).
Rao et al., *Protein Sci.*, 8(11): 2338-2346 (1999).
Rearick et al., *J. Biol. Chem.*, 254(11): 4444-4451 (1979).
Rice et al., *J. Biol. Chem.*, 265(30): 18423-18428 (1990).
Robertson et al., *Mol. Microbio.*, 8(5): 891-901 (1993).
Rosevear et al., *Biochemistry*, 21(6): 1421-1431 (1982).
Sadler et al., *J. Biol. Chem.*, 254(11): 4434-4442 (1979).
Sadler et al., *J. Biol. Chem.*, 254(13): 5934-5941 (1979).
Saenko et al., *Haemophilia*, 12(suppl. 3): 42-51 (2006).
Sambrook et al., "Molecular Cloning: A Laboratory Manual" 2nd ed., Cold Spring Harbor Laboratory Press, Cold Spring Harbor, New York, pp. 9.50-9.51 (1989).
Sandlin et al., *J. Bacteriol.*, 176(10): 2930-2937 (1994).
Schmidt et al., *Trends Cardiovasc. Med.*, 13(1): 39-45 (2003).
Schneider et al., *Infect. Immun.*, 56(4): 942-946 (1988).
Schneider et al., *J. Exp. Med.*, 174(6): 1601-1605 (1991).
Schram et al., *Biochim. Biophys. Acta*, 482(1): 138-144 (1977).
Sears et al., *Science*, 291(5512): 2344-2350 (2001).
Shames et al., *Glycobiology*, 1(2): 187-191 (1991).
Shao et al., *Glycobiology*, 12(11): 763-770 (2002).
Simon et al., *J. Am. Chem. Soc.*, 110(21): 7159-7163 (1988).
Sogin et al., *Biochemistry* 19(23): 5417-5420 (1980).
Sorensen et al., "Incorporation of an Active Site Inhibitor in Factor VIIa Alters the Affinity for Tissue Factor," *J. Biol. Chem.*, 272(18): 11863-11868 (1997).
Stamenkovic et al., *J. Exp. Med.*, 172(2): 641-643 (1990).
Stennicke et al., *Anal. Biochem.*, 248(1): 141-148 (1997).
Stephens et al., *Infect Immun.*, 62(7): 2947-2952 (1994).
Stoolmiller et al., *J. Biol. Chem.*, 244(2): 236-246 (1969).
Suzuki et al., *J. Biol. Chem.*, 260(3): 1362-1365 (1985).
Swiss-Prot Accession No. P19817 (Feb. 1, 1991).
Swiss-Prot Accession No. P25740 (May 1, 1992).
Swiss-Prot Accession No. P27129 (Aug. 1, 1992).
Takegawa et al., *J. Biol. Chem.*, 270(7): 3094-3099 (1995).
Takeya et al., *J. Biol. Chem.*, 263(29): 14868-14877 (1988).
Takeya et al., *Jpn. J. Med. Sci. Biol.*, 46(1): 1-15 (1993).
Tarui et al., *J. Biosci. Bioeng.*, 90(5): 508-514 (2000).
Toone et al., *Tetrahedron*, 45(17): 5365-5422 (1989).
Tsai et al., *Infect. Immun.*, 59(10): 3604-3609 (1991).
Tsuboi et al., "6'-Sulfo Sialyl $Le^x$ but Not 6-Sulfo Sialyl $Le^x$ Expressed on the Cell Surface Supports L-selectin-mediated Adhesion," *J. Biol. Chem.*, 271(44): 27213-27216 (1996).
Tsuji, "Molecular Cloning and Functional Analysis of Sialyltransferases," *J. Biochemistry*, 120: 1-13 (1996).
Tsujihara et al., *Chem. Pharm. Bull.*, (Tokyo) 29(11): 3262-3273 (1981).
Van Den Eijnden et al., *J. Biol. Chem.*, 256(7): 3159-3162 (1981).
Van Den Eijnden et al., *J. Biol. Chem.*, 258(6): 3435-3437 (1983).
Van Putten et al., *EMBO J.*, 12(11): 4043-4051 (1993).
Van Roey et al., *Biochemistry*, 33(47): 13989-13996 (1994).
Vann et al., *J Biol Chem.*, 262(36): 17556-17562 (1987).
Verheul et al., *Microbiol. Rev.*, 57(1): 34-49 (1993).
Vijay et al., *J. Biol. Chem.*, 250(1): 164-170 (1975).
Waddling et al., *Biochemistry*, 39(27): 7878-7885 (2000).
Wakarchuk et al., *J. Biol. Chem.*, 271(32): 19166-19173 (1996).
Wang et al., *Protein Eng.*, 10(4): 405-411 (1997).
Webster et al., *J. Biol. Chem.*, 258(17): 10637-10641 (1983).
Weinstein et al., *J. Biol. Chem.*, 257(22): 13835-13844 (1982).
Weinstein et al., *J. Biol. Chem.*, 257(22): 13845-13853 (1982).
Wen et al., *FASEB Journal*, 6(1): A231 [abstract No. 1329] (1992).
Wen et al., *J. Biol. Chem.*, 267(29): 21011-21019 (1992).
Whisstock et al., *Q. Rev. Biophys.*, 36(3): 307-340 (2003).
Wikipedia, Image:Ceramide.svg, http://en.wikipedia.org/wiki/Ceramide, pp. 1-2 (2007).
Wong et al., *J. Org. Chem.*, 57(16): 4343-4344 (1992).
Xiao et al., *J. Biol. Chem.*, 280(22): 21099-21106 (2005).
Yamamoto et al., *J. Biol. Chem.*, 265(31): 19257-19262 (1990).
Yamamoto et al., *Nature*, 345(6272): 229-233 (1990).
Yamasaki et al., *J. Bacteriol.*, 175(14): 4565-4568 (1993).
Yoshikawa et al., *Phytochemistry*, 34(5): 1431-1433 (1993).
Zalipsky et al., *Polymer Prepr.*, 27(1): 1-2 (1986).
Zalipsky et al., *Int. J. Pept. Protein Res.*, 30(6): 740-783 (1987).
Zapata et al., *J. Biol. Chem.*, 264(25): 14769-14774 (1989).
Zhou et al., *J. Biol. Chem.*, 269(15): 11162-11169 (1994).
Weerapana et al., "Investigating Bacterial N-Linked Glycosylation: Synthesis and Glycosyl Acceptor Activity of the Undecaprenyl Pyrophosphate-Linked Bacillosamine," *J. Am. Chem. Soc.*, 127(40): 13766-13767 (2005).

\* cited by examiner

FIGURE 3

| Pharmacokinetic parameters G-CSF (XM-22 or pegfilgrastim) [unit] | Pilot cohort (25 μg/kg, test) | Group A (50 μg/kg XM22, test) | Group B (100 μg/kg XM22, test) | Group D (100 μg/kg Neulasta®, Reference) |
|---|---|---|---|---|
| AUC$_{(0-tlast)}$ [hr*pg/mL] | 965895.10 | 2516797.22 | 15744903.59 | 12450575.03 |
| AUC$_{(0-\infty)}$ [hr*pg/mL] | 1123056.06 | 2651018.14 | 15903783.04 | 12617511.87 |
| Cl [mL/hr/kg] | 22.26 | 18.86 | 6.29 | 7.93 |
| C$_{max}$ [pg/mL] | 36424.95 | 62430.32 | 296626.65 | 287545.34 |
| t$_{max}$ [hr] | 10.00 | 18.00 | 30.12 | 24.00 |
| t$_{1/2}$ [hr] | 48.84 | 34.13 | 35.57 | 25.35 |
| MRT [hr] | 54.55 | 48.85 | 45.60 | 35.37 |

Pharmacodynamic Results in Cynomolgus Monkeys

GlycoPEG-GCSF and Receptor though non-specific addition of poly(ethylene glycol) molecules has been carried out successfully, the pharmaceutical usefulness is limited due to problems such as lack of homogeneity and small increases in in vivo half-life.

METHODS OF TREATMENT USING GLYCOPEGYLATED G-CSF

CROSS REFERENCE TO RELATED APPLICATIONS

The present application is the U.S. national phase of International Patent Application PCT/US2008/059045, which claims the benefit of U.S. Provisional Patent Application No. 60/909,917, filed Apr. 3, 2007; U.S. Provisional Patent Application No. 60/911,788, filed Apr. 13, 2007; and U.S. Provisional Patent Application No. 60/986,240, filed Nov. 7, 2007, all of which are hereby incorporated in their entirety for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 18,572 bytes ASCII (Text) file named "705497SequenceListing.txt," created Oct. 1, 2009.

BACKGROUND OF THE INVENTION

Granulocyte colony stimulating factor (G-CSF) is a glycoprotein which stimulates the survival, proliferation, differentiation and function of neutrophil granulocyte progenitor cells and mature neutrophils. The two forms of recombinant human G-CSF in clinical use are potent stimulants of neutrophil granulopoiesis and have demonstrated efficacy in preventing infectious complications of some neutropenic states. They can be used to accelerate neutrophil recovery from myelosuppressive treatments.

G-CSF decreases the morbidity of cancer chemotherapy by reducing the incidence of febrile neutropenia, the morbidity of high-dose chemotherapy supported by marrow transplantation, and the incidence and duration of infection in patients with severe chronic neutropenia. Further, G-CSF has been shown to have therapeutic effect when administered after the onset of myocardial infarction.

Acute myelosuppression as a consequence of cytotoxic chemotherapy is well recognized as a dose-limiting factor in cancer treatment. Although other normal tissues may be adversely affected, bone marrow is particularly sensitive to proliferation-specific treatments such as chemotherapy and radiation therapy. For some cancer patients, hematopoietic toxicity frequently limits the opportunity for chemotherapy dose escalation. Repeated or high dose cycles of chemotherapy can lead to stem cell depletion of hematopoietic stem cells and their progeny.

Prevention of and protection from the side effects of chemotherapy and radiation therapy would be of great benefit to cancer patients. G-CSF and other growth factors have been shown to alleviate such side effects by increasing the number of normal critical target cells, particularly hematopoietic progenitor cells.

The human form of G-CSF was cloned by groups from Japan and the U.S.A. in 1986 (see e.g., Nagata et al. *Nature* 319: 415-418, 1986). The natural human glycoprotein exists in two forms, one of 175 and the other of 178 amino acids. The more abundant and more active 175 amino acid form has been used in the development of pharmaceutical products by recombinant DNA technology.

The recombinant human G-CSF synthesised in an *E. coli* expression system is called filgrastim. The structure of filgrastim differs slightly from the natural glycoprotein. The other form of recombinant human G-CSF is called lenograstim and is synthesised in Chinese hamster ovary (CHO) cells.

hG-CSF is a monomeric protein that dimerizes the G-CSF receptor by formation of a 2:2 complex of 2 G-CSF molecules and 2 receptors (Horan et al. *Biochemistry*, 35(15): 4886-96 (1996)). The following hG-CSF residues have been identified by X-ray crystalographic studies as being part of the receptor binding interfaces: G4, P5, A6, S7, S8, L9, P10, Q11, S12, L15, K16, E19, Q20, L108, D109, D112, T115, T116, Q119, E122, E123, and L124 (see e.g., Aritomi et al., (1999) *Nature* 401: 713).

The commercially available forms of rhG-CSF have a short-term pharmacological effect and must often be administered more than once a day for the duration of the leukopenic state. A molecule with a longer circulation half-life would decrease the number of administrations necessary to alleviate leukopenia and prevent consequent infections. Another problem with currently available rG-CSF products is the occurrence of dose-dependent bone pain. Since bone pain is experienced by patients as a significant side effect of treatment with rG-CSF, it would be desirable to provide a rG-CSF product that does not cause bone pain, either by means of a product that inherently does not have this effect or that is effective in a sufficiently small dose that no bone pain is caused. Thus, there is clearly a need for improved recombinant G-CSF molecules.

Protein-engineered variants of hG-CSF have been reported (U.S. Pat. No. 5,581,476, U.S. Pat. No. 5,214,132, U.S. Pat. No. 5,362,853, U.S. Pat. No. 4,904,584 and Riedhaar-Olson et al. Biochemistry 35: 9034-9041, 1996). Modification of hG-CSF and other polypeptides so as to introduce at least one additional carbohydrate chain as compared to the native polypeptide has also been reported (U.S. Pat. No. 5,218,092). In addition, polymer modifications of native hG-CSF, including attachment of PEG groups, have been reported and studied (see e.g., Satake-Ishikawa et al., (1992) *Cell Structure and Function* 17: 157; Bowen et al. (1999) *Experimental Hematology* 27: 425; U.S. Pat. No. 5,824,778, U.S. Pat. No. 5,824,784, WO 96/11953, WO 95/21629, and WO 94/20069).

The attachment of synthetic polymers to the peptide backbone in an attempt to improve the pharmacokinetic properties of glycoprotein therapeutics is known in the art. An exemplary polymer that has been conjugated to peptides is poly (ethylene glycol) ("PEG"). The use of PEG to derivatize peptide therapeutics has been demonstrated to reduce the immunogenicity of the peptides. For example, U.S. Pat. No. 4,179,337 (Davis et al.) discloses non-immunogenic polypeptides such as enzymes and peptide hormones coupled to polyethylene glycol (PEG) or polypropylene glycol. In addition to reduced immunogenicity, the clearance time in circulation is prolonged due to the increased size of the PEG-conjugate of the polypeptides in question.

One mode of attachment of PEG (and its derivatives) to peptides is a non-specific bonding through a peptide amino acid residue (see e.g., U.S. Pat. No. 4,088,538 U.S. Pat. No. 4,496,689, U.S. Pat. No. 4,414,147, U.S. Pat. No. 4,055,635, and PCT WO 87/00056). Another mode of attaching PEG to peptides is through the non-specific oxidation of glycosyl residues on a glycopeptide (see e.g., WO 94/05332).

In these non-specific methods, poly(ethyleneglycol) is added in a random, non-specific manner to reactive residues on a peptide backbone. Of course, random addition of PEG molecules has its drawbacks, including a lack of homogeneity of the final product, and the possibility for reduction in the biological or enzymatic activity of the peptide. Therefore, for the production of therapeutic peptides, a derivitization strategy that results in the formation of a specifically labeled, readily characterizable, essentially homogeneous product is superior. Such methods have been developed.

Specifically labeled, homogeneous peptide therapeutics can be produced in vitro through the action of enzymes. Unlike the typical non-specific methods for attaching a synthetic polymer or other label to a peptide, enzyme-based syntheses have the advantages of regioselectivity and stereoselectivity. Two principal classes of enzymes for use in the synthesis of labeled peptides are glycosyltransferases (e.g., sialyltransferases, oligosaccharyltransferases, N-acetylglucosaminyltransferases), and glycosidases. These enzymes can be used for the specific attachment of sugars which can be subsequently modified to comprise a therapeutic moiety. Alternatively, glycosyltransferases and modified glycosidases can be used to directly transfer modified sugars to a peptide backbone (see e.g., U.S. Pat. No. 6,399,336, and U.S. Patent Application Publications 20030040037, 20040132640, 20040137557, 20040126838, and 20040142856, each of which are incorporated by reference herein). Methods combining both chemical and enzymatic synthetic elements are also known (see e.g., Yamamoto et al. Carbohydr. Res. 305: 415-422 (1998) and U.S. Patent Application Publication 20040137557 which is incorporated herein by reference).

In response to the need for improved therapeutic G-CSF, the present invention provides a glycopegylated G-CSF that is therapeutically active and which has pharmacokinetic parameters and properties that are improved relative to an identical, or closely analogous, G-CSF peptide that is not glycopegylated. Furthermore, the invention provides methods for increasing hematopoiesis in a subject, particularly a subject who has received or will receive radiation or chemotherapy treatment.

SUMMARY OF THE INVENTION

Accordingly, in one aspect, the invention provides methods and compositions for mobilizing stem cell production in a bone marrow transplant recipient. These methods and compositions include administering to a bone marrow tranplant recipient an amount of a peptide which is a covalent conjugate between a G-CSF peptide and a polymeric modifying group. In one aspect, the polymeric modifying group is covalently attached to the peptide at a glycosyl or amino acid residue of the peptide via an intact glycosyl linking group.

In another aspect, the invention provides methods and compositions for increasing the number of granulocytes in a subject. The method includes the step of administering to the subject an amount of a peptide which is a covalent conjugate between a G-CSF peptide and a polymeric modifying group. In one aspect, the G-CSF peptide has the amino acid sequence of SEQ ID NO: 1, and the polymeric modifying group is covalently attached to the G-CSF peptide in the region of the amino acid sequence extending from glycine at position 126 to serine at position 143.

In still another aspect, the invention provides methods and compositions for increasing stem cell production in a subject. The methods include the step of administering to the subject an amount of a peptide which is a covalent conjugate between a G-CSF peptide and a polymeric modifying group. In a further aspect, the G-CSF peptide comprises a structure according to the formula

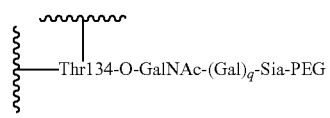

wherein
q is 0 or 1; and
Sia-PEG has a structure according to the formula:

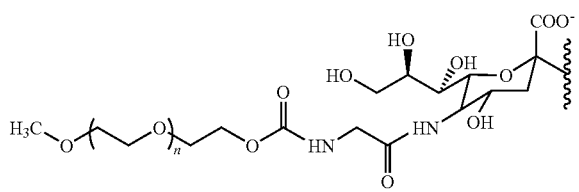

in which n is an integer from 1 to 2000.

In one aspect, the invention provides methods for preventing, treating and alleviating myelosuppresssion, particularly myelosuppression which results from cancer therapy. In one aspect, this method comprises administering to a recipient an amount of a peptide, which is a covalent conjugate between a G-CSF peptide and a polymeric modifying group. The polymeric modifying group of the covalent conjugate can be covalently attached to the G-CSF peptide at a glycosyl or amino acid residue of the G-CSF peptide via an intact glycosyl linking group.

In another aspect, the invention provides methods for treating a condition in a subject, where the condition is characterized by a compromised white blood cell production in the subject. In one aspect, the method for treating the condition comprises a step of administering to the subject an amount of a peptide, which is a covalent conjugate between a G-CSF peptide and a polymeric modifying group. The polymeric modifying group of the covalent conjugate can be covalently attached to the G-CSF peptide at a glycosyl or amino acid residue of the G-CSF peptide via an intact glycosyl linking group. The amount of peptide which is administered to the subject is effective to ameliorate the condition in the subject.

In still another aspect, the invention provides methods for treating neutropenia in a mammal. These methods include the step of administering a pharmaceutically effective amount of a peptide which is a covalent conjugate between a G-CSF peptide and a polymeric modifying group. The polymeric modifying group of the covalent conjugate can be covalently attached to the G-CSF peptide at a glycosyl or amino acid residue of the G-CSF peptide via an intact glycosyl linking group.

In yet another aspect, the invention provides methods for treating thrombocytopenia in a mammal. These methods include the step of administering a pharmaceutically effective amount of a peptide which is a covalent conjugate between a G-CSF peptide and a polymeric modifying group. The polymeric modifying group of the covalent conjugate can be covalently attached to the G-CSF peptide at a glycosyl or amino acid residue of the G-CSF peptide via an intact glycosyl linking group.

In one aspect, the invention provides methods for expanding hematopoietic stem cells in culture. These methods include the step of administering to the stem cells an effective amount of a peptide which is a covalent conjugate between a G-CSF peptide and a polymeric modifying group. The polymeric modifying group of the covalent conjugate can be covalently attached to the G-CSF peptide at a glycosyl or amino acid residue of the G-CSF peptide via an intact glycosyl linking group.

In another aspect, the invention provides methods for stimulating hematopoiesis in a subject. These methods include the step of administering to the subject an effective amount of a peptide, which is a covalent conjugate between a G-CSF peptide and a polymeric modifying group. The polymeric modifying group of the covalent conjugate can be covalently attached to the G-CSF peptide at a glycosyl or amino acid residue of the G-CSF peptide via an intact glycosyl linking group.

In still another aspect, the invention provides methods for increasing the number of hematopoietic progenitor cells in a subject. These methods include the step of administering to the subject an effective amount of a peptide, which is a covalent conjugate between a G-CSF peptide and a polymeric modifying group. The polymeric modifying group of the covalent conjugate can be covalently attached to the G-CSF peptide at a glycosyl or amino acid residue of the G-CSF peptide via an intact glycosyl linking group.

In one aspect, the invention provides methods for mobilizing stem cell production in a donor. These methods include the step of adminstering to the donor an effective amount of a peptide, which is a covalent conjugate between a G-CSF peptide and a polymeric modifying group. The polymeric modifying group of the covalent conjugate can be covalently attached to the G-CSF peptide at a glycosyl or amino acid residue of the G-CSF peptide via an intact glycosyl linking group.

In another aspect, the invention provides methods for enhancing long-term engraftment of bone marrow provided to a recipient. These methods include the step of administering to the bone marrow recipient a peptide, which is a covalent conjugate between a G-CSF peptide and a polymeric modifying group. The polymeric modifying group of the covalent conjugate can be covalently attached to the G-CSF peptide at a glycosyl or amino acid residue of the G-CSF peptide via an intact glycosyl linking group.

In still another aspect, the invention provides methods for mobilizing hematopoietic progenitor cells in a subject. These methods include the step of administering to the subject a first composition comprising a compound of formula 1,1'-[1,4-phenylene-bis-(methylene)-bis-1,4,8,11-tetraazacyclotetradecane (AMD3100) and a second composition comprising a peptide which is a covalent conjugate between a G-CSF peptide and a polymeric modifying group. The polymeric modifying group can be covalently attached to the G-CSF peptide at a glycosyl or amino acid residue of the G-CSF peptide via an intact glycosyl linking group. The first and second composition can be administered to the subject sequentially in any order or simultaneously.

In one aspect, the invention provides an oral dosage form. This oral dosage form can comprise the components: (a) a peptide which is a covalent conjugate between a G-CSF peptide and a polymeric modifying group. The polymeric modifying group can be covalently attached to the G-CSF peptide at a glycosyl or amino acid residue of the G-CSF peptide via an intact glycosyl linking group; (b) surfactant(s); (c) fatty acid(s); and (d) enteric material. In one aspect, components (a), (b) and (c) are mixed in liquid phase and lyophilized prior to combination with component (d).

In another aspect, the invention provides a method for increasing stem cell production in a donor, wherein the method includes the steps of administering to the donor an amount of a peptide which is a covalent conjugate between a G-CSF peptide and a polymeric modifying group. In a further aspect, the polymeric modifying group is attached to the peptide at a glycosyl or amino acid residue of the peptide via a glycosyl linking group. In a still further aspect, the amount of the peptide administered to the donor is in the range of from about 1 mg to about 20 mg.

In still another aspect, the invention provides a method for increasing stem cell production in a donor, wherein the method includes the steps of administering to the donor an amount of a peptide which is a covalent conjugate between a G-CSF peptide and a polymeric modifying group. In a further aspect, the polymeric modifying group is attached to the peptide at a glycosyl or amino acid residue of the peptide via a glycosyl linking group. In a still further aspect, the amount of the peptide administered to the donor is in a unit dosage form. In one embodiment, the unit dosage is selected from: 25 µg/kg, 50 µg/kg, 100 µg/kg, and 200 µg/kg.

DESCRIPTION OF THE DRAWINGS

FIG. 3 is a table of data related to pharmacokinetic parameters for four different test groups.

DETAILED DESCRIPTION OF THE INVENTION AND THE PREFERRED EMBODIMENTS

Abbreviations

Figure 1:
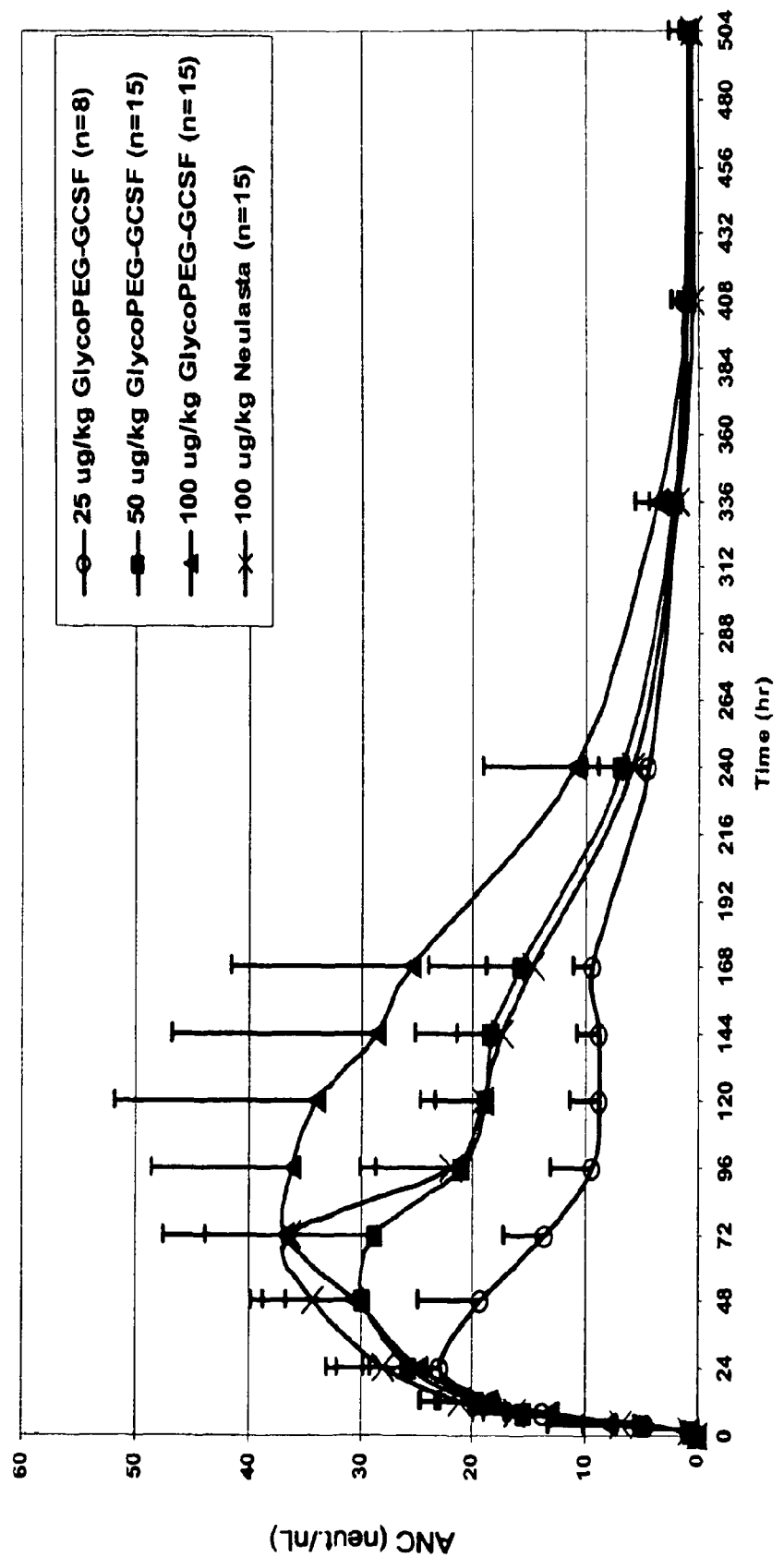
FIG. 1 illustrates data related to absolute neutrophil count (ANC) in response to XM22 (25 µg/kg; 50 µg/kg; 100 µg/kg) and Neulasta (100 µg/kg).

PEG, poly(ethyleneglycol); PPG, poly(propyleneglycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; and NeuAc, sialyl(N-acetylneuraminyl); M6P, mannose-6-phosphate; Sia, sialic acid, N-acetylneuraminyl, and derivatives and analogues thereof.

"G-CSF" refers to Granulocyte Colony Stimulating Factor.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

All oligosaccharides described herein are described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature, see, *Essentials of Glycobiology* Varki et al. eds. CSHL Press (1999).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

"Peptide" refers to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The amino acid or nucleic acid sequence of a peptide is "homologous" to another if there is some degree of sequence identity between the two. Preferably, a homologous sequence will have at least about 85% sequence identity to the reference sequence, preferably with at least about 90% to 100% sequence identity, more preferably with at least about 91% sequence identity, with at least about 92% sequence identity, with at least about 93% sequence identity, with at least about 94% sequence identity, more preferably still with at least about 95% to 99% sequence identity, preferably with at least about 96% sequence identity, with at least about 97% sequence identity, with at least about 98% sequence identity, still more preferably with at least about 99% sequence identity, and about 100% sequence identity to the reference amino acid or nucleotide sequence.

The term "peptide conjugate," refers to species of the invention in which a peptide is conjugated with a modified sugar as set forth herein.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, the term "modified sugar," refers to a naturally- or non-naturally-occurring carbohydrate that is enzymatically added onto an amino acid or a glycosyl residue of a peptide in a process of the invention. The modified sugar is selected from enzyme substrates including, but not limited to sugar nucleotides (mono-, di-, and tri-phosphates), activated sugars (e.g., glycosyl halides, glycosyl mesylates) and sugars that are neither activated nor nucleotides. The "modified sugar" is covalently functionalized with a "modifying group." Useful modifying groups include, but are not limited to, PEG moieties, therapeutic moieties, diagnostic moieties, biomolecules and the like. The modifying group is preferably not a naturally occurring, or an unmodified carbohydrate. The locus of functionalization with the modifying group is selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol). Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)$_m$ in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as polypropylene glycol ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The "area under the curve" or "AUC", as used herein in the context of administering a peptide drug to a patient, is defined as total area under the curve that describes the concentration of drug in systemic circulation in the patient as a function of time from zero to infinity.

The term "half-life" or "t½", as used herein in the context of administering a peptide drug to a patient, is defined as the time required for plasma concentration of a drug in a patient to be reduced by one half. There may be more than one half-life associated with the peptide drug depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. For some glycosylated peptides, rapid beta phase clearance may be mediated via receptors on macrophages, or endothelial cells that recognize terminal galactose, N-acetylgalactosamine, N-acetylglucosamine, mannose, or fucose. Slower beta phase clearance may occur via renal glomerular filtration for molecules with an effective radius <2 nm (approximately 68 kD) and/or specific or non-specific uptake and metabolism in tissues. GlycoPEGylation may cap terminal sugars (e.g., galactose or N-acetylgalactosamine) and thereby block rapid alpha phase clearance via receptors that recognize these sugars. It may also confer a larger effective radius and thereby decrease the volume of distribution and tissue uptake, thereby prolonging the late beta phase. Thus, the precise impact of glycoPEGylation on alpha phase and beta phase half-lives may vary depending upon the size, state of glycosylation, and other parameters, as is well known in the art. Further explanation of "half-life" is found in Pharmaceutical Biotechnology (1997, DFA Crommelin and R D Sindelar, eds., Harwood Publishers, Amsterdam, pp 101-120).

The term "glycoconjugation," as used herein, refers to the enzymatically mediated conjugation of a modified sugar species to an amino acid or glycosyl residue of a polypeptide, e.g., a G-CSF peptide of the present invention. A subgenus of "glycoconjugation" is "glyco-PEGylation," in which the modifying group of the modified sugar is poly(ethylene glycol), and alkyl derivative (e.g., m-PEG) or reactive derivative (e.g., H$_2$N-PEG, HOOC-PEG) thereof.

The terms "large-scale" and "industrial-scale" are used interchangeably and refer to a reaction cycle that produces at least about 250 mg, preferably at least about 500 mg, and more preferably at least about 1 gram of glycoconjugate at the completion of a single reaction cycle.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group and to the remainder of the conjugate is not degraded, e.g., oxidized, e.g., by sodium metaperiodate. "Intact glycosyl linking groups" of the invention may be derived from a naturally occurring oligosaccharide by addition of glycosyl unit(s) or removal of one or more glycosyl unit from a parent saccharide structure.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, G-CSF, GM-CSF, M-CSF, EPO and the like.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g., multivalent agents. Therapeutic moiety also includes proteins and constructs that include proteins. Exemplary proteins include, but are not limited to, Granulocyte Colony Stimulating Factor (GCSF), Granulocyte Macrophage Colony Stimulating Factor (GMCSF), Interferon (e.g., Interferon-α, -β, -γ), Interleukin (e.g., Interleukin II), serum proteins (e.g., Factors VII, VIIa, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor ((TNFR)/Fc domain fusion protein)).

As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering," means oral administration, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including preventing the disease or condition from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "effective amount" or "an amount effective to" or a "therapeutically effective amount" or any grammatically equivalent term means the amount that, when administered to an animal for treating a disease, is sufficient to effect treatment for that disease.

The term "isolated" refers to a material that is substantially or essentially free from components, which are used to produce the material. For peptide conjugates of the invention, the term "isolated" refers to material that is substantially or essentially free from components which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous. "Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of a α1,2 fucosyltransferase, a substantially uniform fucosylation pattern exists if substantially all (as defined below) of the Galβ1,4-GlcNAc-R and sialylated analogues thereof are fucosylated in a peptide conjugate of the invention. In the fucosylated structures set forth herein, the Fuc-GlcNAc linkage is generally α1,6 or α1,3, with α1,6 generally preferred. It will be understood by one of skill in the art, that the starting material may contain glycosylated acceptor moieties (e.g., fucosylated Galβ1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —CN and —NO₂ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR—C(NR'R"R'")=NR"", —NR—C(NR'R")=NR'", —S(O)R', —S(O)₂R', —S(O)₂NR'R", —NRSO₂R', —CN and —NO₂, —R', —N₃, —CH(Ph)₂, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_u$—U—, wherein T and U are independently —NR—, —O—, —CRR'— or a single bond, and u is an integer of from 0 to 3. Alternatively, two of the substituents on adjacent atoms of the aryl or heteroaryl ring may optionally be replaced with a substituent of the formula -A-(CH₂)$_r$—B—, wherein A and B are independently —CRR'—, —O—, —NR—, —S—, —S(O)—, —S(O)₂—, —S(O)₂NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula (CRR')$_z$—X—(CR"R'")$_d$—, where z and d are independently integers of from 0 to 3, and X is —O—, —NR'—, —S—, —S(O)—, —S(O)₂—, or —S(O)₂NR'—. The substituents R, R', R" and R'" are preferably independently selected from hydrogen or substituted or unsubstituted ($C_1$-$C_6$)alkyl.

As used herein, the term "heteroatom" is meant to include oxygen (O), nitrogen (N), sulfur (S) and silicon (Si).

"Stem cell" refers to a "generic" or undifferentiated cell that can make copies of itself indefinitely, and can become specialized for various tissues in the body. Stem cells can give rise to normal blood components including red cells, white cells and platelets. Stem cells are normally located in the bone marrow and in the blood and can be harvested for a transplant.

The term "hematopoietic cell" refers to a cell associated with the formation of blood cells. This term can be used interchangeably with the term "stem cell" as defined above.

As used herein, the term "mobilizing stem cell production" is meant to include all processes which increase the number of stem cells in vivo or in vitro. The increased number of stem cells can be the result of an increase in the number of progenitor cells. Also included within the term are the processes of transport of stem cells to and from the bone marrow.

Similarly, the term "mobilizing hematopoietic cell production" is meant to include all processes which increase the number of hematopoietic cells in vivo or in vitro. The increased number of hematopoeitic cells can be the result of an increased number of progenitor cells, an increase in the rate of maturation of pluripotent stem cells into hematopoietic cells, and some combination thereof. Also included within the term are the processes of transport of hematopoietic cells to and from the bone marrow.

The term "granulocytes" refers to white blood cells characterised by the presence of granules in their cytoplasm.

Introduction

The present invention encompasses methods of administering glycopegylated G-CSF for preventing, alleviating, and treating disorders and conditions related to hematopoeitic deficiency, which often results from chemotherapy, radiation therapy, and thrombocytopenia. G-CSF primarily acts on the bone marrow to increase the production of inflammatory leukocytes, and further functions as an endocrine hormone to initiate the replenishment of neutrophils consumed during inflammatory functions. G-CSF also has clinical applications in bone marrow replacement following chemotherapy.

The present invention provides a conjugate comprising granulocyte colony stimulating factor (G-CSF). The invention also encompasses conjugates comprising glycosylated and unglycosylated peptides having granulocyte colony stimulating activity. The conjugates may be additionally modified by further conjugation with diverse species such as therapeutic moieties, diagnostic moieties, targeting moieties and the like. For G-CSF conjugates described herein, a polymeric modifying group can be covalently attached to the G-CSF peptide at a glycosyl or amino acid residue of the G-CSF peptide, preferably via a glycosyl linking group. In an exemplary embodiment, the polymeric modifying group is a water-soluble polymer. In a further preferred embodiment, the water-solutble polymer is poly(ethylene glycol).

In exemplary embodiments, a G-CSF peptide of the invention may be administered to patients for the purposed of preventing infection in cancer patients undergoing radiation therapy, chemotherapy, and bone marrow transplantations, to mobilize progenitor cells for collection in peripheral blood progenitor cell transplantations, for treatment of severe chronic or relative leukopenia, irrespective of cause, and to support treatment of patients with acute myeloid leukemia. Additionally, polypeptide conjugates or compositions of the invention may be used for treatment of AIDS or other immunodeficiency diseases as well as bacterial infections, heart disease, and Hepatitis A, B, and C.

In one embodiment, a G-CSF peptide conjugate of the invention may be administered to a subject to increase hemaptopoiesis. Hematopoiesis is the process by which precursor cells develop into mature blood cells, including red blood cells, white blood cells, and platelets. Normal hematopoiesis is coordinated by a variety of regulators including glycoproteins such as colony stimulating factors. Such regulators modulate the survival, proliferation and differentiation of progenitor and precursor cells and the activation state of mature cells. When hematopoiesis is compromised, the result is a decrease in blood cell and platelet production, leading to compromised immunity and an inability to heal from wounds and infection.

The present invention provides methods and compositions for stimulating hematopoiesis in a subject. Methods of the invention include the step of administering to the subject an effective amount of a peptide which is a covalent conjugate between a G-CSF peptide and a polymeric modifying group.

In one aspect, stimulating hematopoiesis comprises increasing the number of hematopoietic progenitor cells in a subject, with the result that the number of mature hematopoietic cells (blood cells) is also increased. Hematopoietic progenitor cells traffic to and are retained in the bone marrow, where they can mature to become red and white blood cells. Methods of the invention for stimulating the number of hematopoietic progenitor cells include the step of administering to a subject an effective amount of a peptide which is a covalent conjugate between a G-CSF peptide and a polymeric modifying group. In one embodiment, the hematopoietic progenitor cells increased by application of the peptide are CD34+ cells.

Myelosuppression

Myelosuppression is a decrease in the production of blood cells. Normal blood contains large numbers of cells, including red blood cells to carry oxygen and white blood cells to fight infections. Normal blood also contains platelets, tiny cell fragments that initiate blood clotting. These cells and fragments are made in the bone marrow, a substance found in the centers of some bones. Healthy bone marrow makes large numbers of red blood cells, white blood cells, and platelets each day. In myelosuppression, the bone marrow makes too few of these cells. The present invention provides methods and compositions for treating, alleviating, and preventing myelosuppression.

One characteristic of myelosuppression is compromised white blood cell production in a subject. Such compromised white blood cell production can result from certain kinds of treatment, particularly cancer treatments such as chemotherapy and radiation therapy. Compromised white blood cell production can also be the result of disorders such as idiopathic thrombocytopenia purpura. In one aspect, conjugates of the invention are used to treat and ameliorate disorders characterized by a compromised white blood cell production.

Disorders which result from myelosuppression include neutropenia (including febrile neutropenia) and thrombocytopenia. Neutropenia is a condition characterized by an abnormal decrease in the number of neutrophils (the most common type of white blood cells) in the blood. The decrease may be relative or absolute. In one aspect, the invention provides methods for treatment of neutropenia in a mammal. These methods include steps for administering a pharmaceutically effective amount of G-CSF conjugates of the invention. G-CSF has been shown to affect febrile neutropenia and mortality in adult cancer patients. (Kuderer et al., *J. Clin. Onc.* (2007), 25(21):3158-67).

Thrombocytopenia is a disorder in which the number of platelets in the blood is abnormally low and is often associated with abnormal bleeding. Methods of the invention include treatments for thrombocytopenia in a mammal. These methods include steps for administering a pharmaceutically effective amount of G-CSF conjugates of the invention. As used herein, the term thrombocytopenia encompasses disorders of known origin as well as idiopathic thrombocytopenia. Thrombocytopenia and idiopathic thrombocytopenia are also referred to herein as "thrombocytopenia purpura" and "idiopathic thrombocytopenia purpura".

Stem Cell Mobilization

One way to combat myelosuppression is to mobilize stem cell production. Mobilizing stem cell production includes increasing the number of stem cells, including the number of hematopoietic progenitor cells and the number of granulocytes, including neutrophils and eosinophils. Mobilizing stem cell production also includes increasing the transport of stem cells from the bone marrow into the peripheral blood. Such mobilization aids in the harvesting of stem cells from a donor, as peripheral blood is more readily accessible than bone marrow. In one aspect, the present invention provides methods for mobilizing stem cell production in a subject.

In another aspect, myelosuppression is prevented, alleviated and treated using methods and compositions of the present invention by mobilizing hematopoietic progenitor cells in a subject. Mobilizing hematopoietic progenitor cells includes increasing the number of hematopoietic progenitor cells as well as increasing the transport of the cells to and from the bone marrow.

Hematopoietic progenitor cells, such as CD34+ cells, mature and differentiate into components of the blood, namely red and white blood cells. The instant invention provides methods for mobilizing hematopoietic progenitor cells in a subject which include the step of administering to the subject: (i) a first composition comprising a compound of formula (1) is 1,1'-[1,4-phenylene-bis-(methylene)-bis-1,4,8,11-tetraazacyclotetradecane (AMD3100), and n(2) a second composition comprising a peptide which is a covalent conjugate between a G-CSF peptide and a polymeric modifying group. In one embodiment, the first composition and the second composition are administered to the subject sequentially and in any order. In another embodiment, the first composition and the second composition are administered simultaneously. In one embodiment, both compositions are administered to the subject subcutaneously.

AMD3100 is a bicyclam derivative that has been shown to mobilize significant numbers of CD34+ cells into circulation in both normal subjects and in patients with cancer. (Liles et al., *Blood*, (2003), 102:2728-30; Devine et al., *J. Clin. Oncol.*, (2004), 22:1095-1102). Studies have shown that combining AMD3100 with a non-glycosylated form of G-CSF mobilizes higher numbers of CD34+ cells into circulation than with G-CSF alone. (Flomenberg et al., *Blood*, (2005), 106(5): 1867-1874).

In one embodiment, stem cell production is mobilized in a subject who will serve as a bone marrow or hematopoietic cell donor. The donor is provided with a peptide conjugate, as described above. Stem cells from the donor are increased in number and are mobilized to move from the bone marrow into the peripheral blood. Such cells are then easily isolated from the donor using methods known in the art. The donor in such embodiments may be the same as the recipient of the bone marrow or the hematopoietic cells (autologous donor), or the donor may be a subject who is not the recipient (allogenic donor).

In another aspect, peptide conjugates of the invention are provided in combination with at least one chemotherapeutic agent.

Bone Marrow Transplants

In some aspects, the present invention provides methods and compositions for mobilizing stem cell production in a bone marrow transplant recipient. These methods include the step of administering to the recipient an amount of a peptide which is a covalent conjugate between a G-CSF peptide and a polymeric modifying group. In one embodiment, the polymeric modifying group is a water-soluble polymer, which can be covalently attached to the G-CSF peptide at a glycosyl or amino acid residue of the G-CSF peptide, preferably via an intact glycosyl linking group. The peptide may be administered to the recipient prior to transplant of the bone marrow, subsequent to the transplant, or simultaneously with the transplant.

For successful transplantation, long-term engraftment is crucial. The term "engraftment" refers to the process of infused or transplanted donor stem cells homing to the marrow of a recipient and producing blood cells of all types. Engraftment is first evident when new white cells, red cells and platelets begin to appear in the recipient's blood following stem cell transplantation. Long-term engraftment refers to the process in which infused or transplanted donor cells remain in the marrow of the recipient and produce blood cells over an extended period of time without rejection by the immune system of the recipient. Inclusion of intermediate and late progenitor cells in a transplant can accelerate the production of donor-derived mature cells and support the engraftment process.

Accordingly, the present invention provides methods and compositions for enhancing long-term engraftment of bone marrow provided to a recipient. In one exemplary embodiment, a peptide of the invention is administered to a donor prior to the bone marrow transplant. The peptide increases hematopoiesis in the donor, in particular increasing the number of progenitor cells, which increases the success and longevity of engraftment when the bone marrow and/or the hematopoietic cells are transplanted into a recipient. The transplanted bone marrow can be the recipient's own bone marrow (autologous), or the bone marrow can be transplanted from a donor of the same species (allogenic).

In another embodiment, a peptide of the invention is administered to the recipient of the bone marrow to enhance long-term engraftment of the donated bone marrow, whether that bone marrow comes from the recipient itself or from another individual. Application of the peptide to the recipient can serve to increase hematopoiesis in the recipient, thus enhancing engraftment by stimulating the donated bone marrow to increase production of hematopoietic progenitor cells.

Hematopoietic Cell Transplants

Transplantation of hematopoietic cells is a common treatment for a variety of inherited or malignant diseases. While some transplantation procedures utilize the entire bone marrow population, other procedures utilize more defined populations enriched for stem cells. In addition to bone marrow, such cells can be derived from other sources, such as peripheral blood and neonatal umbilical cord blood. One advantage of using stem cells from peripheral blood is that these cells are more easily accessed in peripheral blood than in bone marrow. However, a limiting factor for peripheral blood stem cell transplantation is the low number of circulating pluripotent stem/progenitor cells. Thus, there is a need for expanding stem cells ex vivo for use in transplantation.

Accordingly, the present invention provides methods for expanding hematopoietic cells in culture. Such methods include in an exemplary embodiment administering an effective amount of a peptide of the invention to a culture of hematopoietic cells. Such a peptide will in an exemplary embodiment be a conjugate between a G-CSF peptide and a polymeric modifying group. In one embodiment, the polymeric modifying group is a water-soluble polymer, which can be covalently attached to the G-CSF peptide at a glycosyl or amino acid residue of the G-CSF peptide, preferably via an intact glycosyl linking group. In one embodiment, the present invention provides methods of providing expanded populations of stem cells, as well as progenitor cells, which can be used for transplantations. These methods include the step of administering to a culture of stem cells an effective amount of amount of peptides of the invention.

Organ Transplants

Similar to bone marrow transplants, solid organ transplants, such as liver, kidney, heart and lung can evoke a variety of immune responses in a recipient. Such immune responses can lead to acute rejection of these grafts. G-CSF and other hematopoietic growth factors can be used to treat such responses, (U.S. Pat. No. 5,718,893). Accordingly, the methods and compositions of the present invention can be used to prevent or reduce the occurrence of acute rejection of organ transplants in a patient.

Heart Disease

In one embodiment, methods and compositions of the present invention can be used to alleviate heart disease and improve heart function. In one embodiment, methods and compositions of the invention are used to stimulate the release of blood vessel-forming stem cells. Treatment with G-CSF can reduce angina in patients with heart disease, including patients who have undergone multiple surgeries and who have taken maximum doses of conventional medicines. (see, e.g., *Medical News Today*, Jun. 4, 2007, "Severe Heart Disease Patients Offered New Hope".) Other studies have shown that G-CSF can rescue and protect heart muscles to prevent these muscles from dying even when the muscles have been damaged by heart disease. (see, e.g., *Sunday Telegraph News*, Aug. 5, 2007, "Our World-first hearts that Repair Themselves".) G-CSF alone or in combination with adult stem cells from patients can be used as a treatment to repair dead tissue in the heart and generate new blood vessels.

Neurological Disease

In one embodiment, methods and compositions of the invention can be used to treat neurological diseases, including without limitation Alzheimer's disease and other degenerative brain disorders. Studies in mouse models of Alzheimer's disease have shown that G-CSF can reverse Alzheimer's-like symptoms in these models. (see Tsai et al., (2007), *J. Exp. Med.* 204(6): 1273-80). These studies indicate that injection of G-CSF into the bloodstream facilitate release of hematopoietic stem cells from bone marrow. These stem cells pass into the brain from the bloodstream, where they attach to sites of damage and become differentiated into new cells. The application of G-CSF causes new cells to grow where neuron damage is the greatest.

G-CSF Conjugates

According to any of the methods set forth above, the peptide is a covalent conjugate between a G-CSF peptide and a polymeric modifying group. The polymeric modifying group can be covalently attached to the G-CSF peptide at a glycosyl or amino acid residue of the G-CSF peptide, preferably via a glycosyl linking group. In one embodiment, the glycosyl linking group is an intact glycosyl linking group. In preferred embodiments, the polymeric modifying group and the glycosyl linking group are covalently attached through a linker. In an exemplary embodiment, the polymeric modifying group is a water-soluble polymer such as poly(ethylene glycol).

G-CSF has been cloned and sequenced. In an exemplary embodiment, G-CSF has an amino acid sequence according to SEQ ID NO:1. The skilled artisan will readily appreciate that the present invention is not limited to the sequences depicted herein.

The present invention further encompasses G-CSF variants, as well known in the art. As an example, but in no way meant to be limiting to the present invention, a G-CSF variant has been described in U.S. Pat. No. 6,166,183, in which a G-CSF comprising the natural complement of lysine residues and further linked to one or two polyethylene glycol molecules is described. Additionally, U.S. Pat. Nos. 6,004,548, 5,580,755, 5,582,823, and 5,676,941 describe a G-CSF variant in which one or more of the cysteine residues at position 17, 36, 42, 64, and 74 are replaced by alanine or alternatively serine. U.S. Pat. No. 5,416,195 describes a G-CSF molecule in which the cysteine at position 17, the aspartic acid at position 27, and the serines at positions 65 and 66 are substituted with serine, serine, proline, and proline, respectively. Other variants are well known in the art, and are described in, for example, U.S. Pat. No. 5,399,345. Still further variants have an amino acid selected from SEQ ID Nos:3-11.

The expression and activity of a modified G-CSF molecule of the present invention can be assayed using methods well known in the art, and as described in, for example, U.S. Pat. No. 4,810,643. As an example, activity can be measured using radio-labeled thymidine uptake assays. Briefly, human bone marrow from healthy donors is subjected to a density cut with Ficoll-Hypaque (1.077 g/ml, Pharmacia, Piscataway, N.J.) and low density cells are suspended in Iscove's medium (GIBCO, La Jolla, Calif.) containing 10% fetal bovine serum, glutamine and antibiotics. About $2 \times 10^4$ human bone marrow cells are incubated with either control medium or the G-CSF or the present invention in 96-well flat bottom plates at about 37° C. in 5% $CO_2$ in air for about 2 days. Cultures are then pulsed for about 4 hours with 0.5 µCi/well of $^3$H-thymidine (New England Nuclear, Boston, Mass.) and uptake is measured as described in, for example, Ventua, et al. (1983, Blood 61:781). An increase in $^3$H-thymidine incorporation into human bone marrow cells as compared to bone marrow cells treated with a control compound is an indication of an active and viable G-CSF compound.

Conjugates of the invention are formed by the enzymatic attachment of a modified sugar to the glycosylated or unglycosylated G-CSF peptide. The modified sugar, when interposed between the G-CSF peptide and the modifying group on the sugar becomes what may be referred to herein e.g., as an "intact glycosyl linking group." Using the exquisite selectivity of enzymes such as glycosyltransferases, the present method provides peptides that bear a desired group at one or more specific locations. Thus, according to the present invention, a modified sugar is attached directly to a selected locus on the G-CSF peptide chain or, alternatively, the modified sugar is appended onto a carbohydrate moiety of a glycopeptide. Peptides in which modified sugars are bound to both a glycopeptide carbohydrate and directly to an amino acid residue of the G-CSF peptide backbone are also within the scope of the present invention.

In contrast to known chemical and enzymatic peptide elaboration strategies, it is possible to use methods of the invention to assemble peptides and glycopeptides that have a substantially homogeneous derivatization pattern; the enzymes used according to the invention are generally selective for a particular amino acid residue or combination of amino acid residues of the G-CSF peptide. Such methods can also apply to large-scale production of modified peptides and glycopeptides. Thus, the methods of the invention provide a practical means for large-scale preparation of glycopeptides having preselected uniform derivatization patterns. The methods are particularly well suited for modification of therapeutic peptides, including but not limited to, glycopeptides that are incompletely glycosylated during production in cell culture cells (e.g., mammalian cells, insect cells, plant cells, fungal cells, yeast cells, or prokaryotic cells) or transgenic plants or animals.

The present invention also provides conjugates of glycosylated and unglycosylated G-CSF peptides with increased therapeutic half-life due to, for example, reduced clearance rate, or reduced rate of uptake by the immune or reticuloendothelial system (RES). Moreover, the methods of the invention provide a means for masking antigenic determinants on peptides, thus reducing or eliminating a host immune response against the peptide. Selective attachment of targeting agents can also be used to target a peptide to a particular tissue or cell surface receptor that is specific for the particular targeting agent.

In one embodiment, the present invention provides a conjugate between a selected modifying group and a G-CSF peptide. The link between the peptide and the modifying moiety includes a glycosyl linking group interposed between the peptide and the selected moiety. As discussed herein, the selected modifying moiety is essentially any species that can be attached to a saccharide unit, resulting in a "modified sugar" that is recognized by an appropriate transferase enzyme, which appends the modified sugar onto the peptide, or a glycosyl residue attached thereto. The saccharide component of the modified sugar, when interposed between the peptide and a selected moiety, becomes a "glycosyl linking group," e.g., an "intact glycosyl linking group." The glycosyl linking group is formed from any mono- or oligo-saccharide that, after modification with the modifying group, is a substrate for an enzyme that adds the modified sugar to an amino acid or glycosyl residue of a peptide.

The glycosyl linking group can be, or can include, a saccharide moiety that is degradatively modified before or during the addition of the modifying group. For example, the glycosyl linking group can be derived from a saccharide residue that is produced by oxidative degradation of an intact saccharide to the corresponding aldehyde, e.g., via the action of metaperiodate, and subsequently converted to a Schiff base with an appropriate amine, which is then reduced to the corresponding amine.

The conjugates of the invention will typically correspond to the general structure:

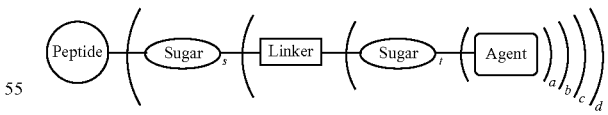

in which the symbols a, b, c, d and s represent a positive, non-zero integer; and t is either 0 or a positive integer. The "agent" is typically a water-soluble moiety, e.g., a PEG moiety. The linker can be any of a wide array of linking groups, infra. Alternatively, the linker may be a single bond or a "zero order linker."

Modifying groups can include, as is discussed further herein, any species that can be attached to a saccharide unit. Such groups include polymers, including water-soluble and water-insoluble polymers, and can also include therapeutic moieties, diagnostic moieties, targeting moietyies, toxin moieties and the like. In an exemplary embodiment, the selected modifying group is a water-soluble polymer, e.g., m-PEG. The water-soluble polymer is covalently attached to the G-CSF peptide via a glycosyl linking group, which is covalently attached to an amino acid residue or a glycosyl residue of the G-CSF peptide. The invention also provides conjugates in which an amino acid residue and a glycosyl residue are modified with a glycosyl linking group.

The peptides of the present invention include at least on N- or O-linked glycosylation site. In addition to providing conjugates that are formed through an enzymatically added glycosyl linking group, the present invention provides conjugates that are highly homogenous in their substitution patterns. Using the methods of the invention, it is possible to form peptide conjugates in which essentially all of the modified sugar moieties across a population of conjugates of the invention are attached to multiple copies of a structurally identical amino acid or glycosyl residue. Thus, in one aspect, the invention provides a peptide conjugate having a population of water-soluble polymer moieties, which are covalently bound to the G-CSF peptide through an intact glycosyl linking group. In an exemplary embodiment of a conjugate of the invention, essentially each member of the population of water-soluble polymer moieties is bound via the glycosyl linking group to a glycosyl residue of the G-CSF peptide, and each glycosyl residue of the G-CSF peptide to which the glycosyl linking group is attached has the same structure.

Also provided is a peptide conjugate having a population of water-soluble polymer moieties covalently bound thereto through a glycosyl linking group. In one embodiment, essentially every member of the population of water soluble polymer moieties is bound to an amino acid residue of the G-CSF peptide via a glycosyl linking group, and each amino acid residue having a glycosyl linking group attached thereto has the same structure.

The present invention also provides conjugates analogous to those described above in which the G-CSF peptide is conjugated to a therapeutic moiety, diagnostic moiety, targeting moiety, toxin moiety or the like via an intact glycosyl linking group. Each of the above-recited moieties can be a small molecule, natural polymer (e.g., polypeptide) or synthetic polymer.

Modified Sugars

The present invention provides modified sugars, modified sugar nucleotides and conjugates of the modified sugars. In modified sugar compounds of the invention, the sugar moiety is preferably a saccharide, a deoxy-saccharide, an aminosaccharide, or an N-acyl saccharide. The term "saccharide" and its equivalents, "saccharyl," "sugar," and "glycosyl" refer to monomers, dimers, oligomers and polymers. The sugar moiety is also functionalized with a modifying group. The modifying group is conjugated to the sugar moiety, typically, through conjugation with an amine, sulfhydryl or hydroxyl, e.g., primary hydroxyl, moiety on the sugar. In an exemplary embodiment, the modifying group is attached through an amine moiety on the sugar, e.g., through an amide, a urethane or a urea that is formed through the reaction of the amine with a reactive derivative of the modifying group.

Any sugar can be utilized as the sugar core of the conjugates of the invention. Exemplary sugar cores that are useful in forming the compositions of the invention include, but are not limited to, glucose, galactose, mannose, fucose, and sialic acid. Other useful sugars include amino sugars such as glucosamine, galactosamine, mannosamine, the 5-amine analogue of sialic acid and the like. The sugar core can be a structure found in nature or it can be modified to provide a site for conjugating the modifying group. For example, in one embodiment, the invention provides a peptide conjugate comprising a sialic acid derivative in which the 9-hydroxy moiety is replaced with an amine. The amine is readily derivatized with an activated analogue of a selected modifying group.

Glycosyl Linking Group

In accordance with the peptide conjugates of any of the methods set forth above, some embodiments of the peptide conjugates comprise a glycosyl linking group which is a sialic acid residue.

The link between the G-CSF peptide and a selected moiety, such as a water-soluble polymer, includes an intact glycosyl linking group interposed between the peptide and the selected moiety. As discussed herein, the selected moiety is essentially any species that can be attached to a saccharide unit, resulting in a "modified sugar" that is recognized by an appropriate transferase enzyme, which appends the modified sugar onto the G-CSF peptide. The saccharide component of the modified sugar, when interposed between the G-CSF peptide and a selected moiety, becomes an "intact glycosyl linking group." The glycosyl linking group is formed from any mono- or oligo-saccharide that, after modification with a selected moiety, is a substrate for an appropriate transferase.

In one embodiment, the glycosyl linking group is a sialic acid residue which has a structure according to the formula:

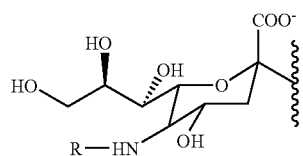

in which R is the water-soluble polymer and the water-soluble polymer is attached to the sialic acid residue through said linker.

In another embodiment, the glycosyl linking group is a sialic acid residue which has a structure according to the formula:

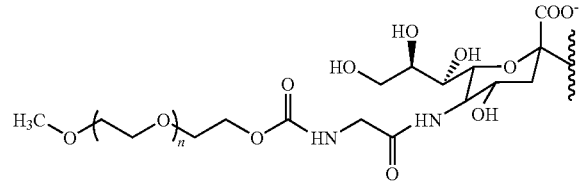

in which n is an integer from 1 to 2000.

In still another embodiment, the glycosyl linking group comprises a modified sialyl residue having the formula:

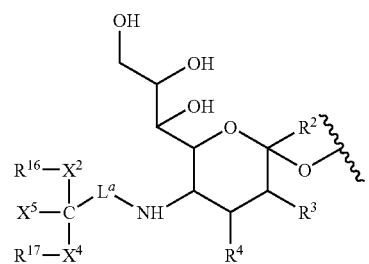

wherein
  $R^2$ is H, $CH_2OR^7$, $COOR^7$ or $OR^7$
wherein
  $R^7$ represents H, substituted or unsubstituted alkyl or substituted or unsubstituted heteroalkyl;
  $R^3$ and $R^4$ are members independently selected from H, substituted or unsubstituted alkyl, $OR^8$, $NHC(O)R^9$
wherein
  $R^8$ and $R^9$ are independently selected from H, substituted or unsubstituted alkyl, substituted or unsubstituted heteroalkyl or sialic acid;
  $L^a$ is a linker selected from a bond, substituted or unsubstituted alkyl and substituted or unsubstituted heteroalkyl'
  $R^{16}$ and $R^{17}$ are independently selected polymeric arms;
  $X^2$ and $X^4$ are independently selected linkage fragments joining polymeric moieties $R^{16}$ and $R^{17}$ to C; and
  $X^5$ is a non-reactive group.

In a further embodiment, the amino acid residue is a member selected from serine or threonine. In a still further embodiment, the amino acid residue is threonine at position 133 of SEQ. ID. NO:1.

In one embodiment, the glycosyl linking group comprises a substructure that is selected from:

$$\text{---(GalNAc-Gal)}_p\text{-R}^{15}; \text{ and } \text{---(GalNAc-Gal)}_p\text{-Sia-R}^{15}$$

wherein
  $R^{15}$ is a modified sialyl residue; and
  p is an integer from 1 to 10.

In a further embodiment, the glycosyl linking group has a formula selected from:

$$\begin{array}{l}
(Fuc)_t \quad\quad Man\text{-(GlcNAc-Gal)}_p\text{-R}^{15'}; \\
| \quad\quad\quad\quad\quad | \\
AA\text{-GlcNAc-GlcNAc-Man} \\
\quad\quad\quad\quad\quad\quad | \\
\quad\quad\quad\quad\quad\quad Man
\end{array}$$

$$\begin{array}{l}
(Fuc)_t \quad\quad Man \\
| \quad\quad\quad\quad\quad | \\
AA\text{-GlcNAc-GlcNAc-Man} \\
\quad\quad\quad\quad\quad\quad | \\
\quad\quad\quad\quad\quad\quad Man\text{-(GlcNAc-Gal)}_p\text{-R}^{15'};
\end{array}$$

$$\begin{array}{l}
(Fuc)_t \quad\quad Man\text{-(GlcNAc-Gal)}_p\text{-R}^{15'} \\
| \quad\quad\quad\quad\quad | \\
AA\text{-GlcNAc-GlcNAc-Man} \\
\quad\quad\quad\quad\quad\quad | \\
\quad\quad\quad\quad\quad\quad Man\text{-(GlcNAc-Gal)}_p\text{-R}^{15'};
\end{array}$$

$$\begin{array}{l}
(Fuc)_t \quad\quad Man\text{-(GlcNAc-Gal)}_p\text{-R}^{15'} \\
| \quad\quad\quad\quad\quad | \\
AA\text{-GlcNAc-GlcNAc-Man-(GlcNAc-Gal)}_p\text{-R}^{15'} \\
\quad\quad\quad\quad\quad\quad | \\
\quad\quad\quad\quad\quad\quad Man\text{-(GlcNAc-Gal)}_p\text{-R}^{15'}; \text{ and}
\end{array}$$

$$\begin{array}{l}
\quad\quad\quad\quad\quad\quad\quad (GlcNAc\text{-Gal})_p\text{-R}^{15'} \\
\quad\quad\quad\quad\quad\quad\quad | \\
(Fuc)_t \quad\quad Man\text{-(GlcNAc-Gal)}_p\text{-R}^{15'} \\
| \quad\quad\quad\quad\quad | \\
AA\text{-GlcNAc-GlcNAc-Man-(GlcNAc-Gal)}_p\text{-R}^{15'} \\
\quad\quad\quad\quad\quad\quad | \\
\quad\quad\quad\quad\quad\quad Man\text{-(GlcNAc-Gal)}_p\text{-R}^{15'} \\
\quad\quad\quad\quad\quad\quad | \\
\quad\quad\quad\quad\quad\quad (GlcNAc\text{-Gal})_p\text{-R}^{15'}
\end{array}$$

wherein
  AA is an amino acid residue of said peptide;
  t is an integer equal to 0 or 1;
  p is an integer from 1 to 10; and
  $R^{15'}$ is a member selected from H, OH, sialic acid, said modified sialyl residue and Sia-Sia$^p$
wherein
  Sia$^p$ is said modified sialyl residue,
  wherein at least one $R^{15'}$ is selected from said modified sialyl residue and Sia-Sia$^p$. In one embodiment, the amino acid residue is an asparagine residue.

In another embodiment, said G-CSF peptide comprises a structure according to the formula $$\text{---Thr134-O-GalNAc-(Gal)}_q\text{-Sia-PEG}$$

wherein q is 0 or 1; and Sia-PEG has a structure according to the formula:

$$H_3C-O-(-O-)_n-O-HN-\overset{O}{\underset{}{C}}-HN-\text{[sialic acid moiety with COO}^-, \text{HO, OH, OH]}$$

in which n is an integer from 1 to 2000. In a further embodiment, n is an integer from 400 to 500. In a still further embodiment, the G-CSF peptide has the amino acid sequence SEQ ID NO:1.

In the discussion that follows the invention is illustrated by reference to the use of selected derivatives of sialic acid. Those of skill in the art will recognize that the focus of the discussion is for clarity of illustration and that the structures and compositions set forth are generally applicable across the genus of saccharide groups, modified saccharide groups, activated modified saccharide groups and conjugates of modified saccharide groups.

In an exemplary embodiment, the invention provides a peptide conjugate comprising a modified sugar amine that has the formula:

$$G-NH-L-R^1$$

in which G is a glycosyl moiety, L is a bond or a linker and $R^1$ is the modifying group. Exemplary bonds are those that are formed between an $NH_2$ on the glycosyl moiety and a group of complementary reactivity on the modifying group. Thus, exemplary bonds include, but are not limited to $NHR^1$, $OR^1$, $SR^1$ and the like. For example, when $R^1$ includes a carboxylic acid moiety, this moiety may be activated and coupled with an $NH_2$ moiety on the glycosyl residue affording a bond having the structure $NHC(O)R^1$. Similarly, the OH and SH groups can be converted to the corresponding ether or thioether derivatives, respectively.

Exemplary linkers include alkyl and heteroalkyl moieties. The linkers include linking groups, for example acyl-based linking groups, e.g., —C(O)NH—, —OC(O)NH—, and the like. The linking groups are bonds formed between components of the species of the invention, e.g., between the glycosyl moiety and the linker (L), or between the linker and the modifying group ($R^1$). Other linking groups are ethers, thioethers and amines. For example, in one embodiment, the linker is an amino acid residue, such as a glycine residue. The carboxylic acid moiety of the glycine is converted to the corresponding amide by reaction with an amine on the glycosyl residue, and the amine of the glycine is converted to the corresponding amide or urethane by reaction with an activated carboxylic acid or carbonate of the modifying group.

Another exemplary linker is a PEG moiety or a PEG moiety that is functionalized with an amino acid residue. The based on species in which the —NH moiety is replaced by, for example, —S, —O and —$CH_2$.

More particularly, the invention provides a peptide conjugate comprising compounds in which NH-L-$R^1$ is: $NHC(O)(CH_2)_a NHC(O)(CH_2)_b(OCH_2CH_2)_c O(CH_2)_d NHR^1$, $NHC(O)(CH_2)_b(OCH_2CH_2)_c O(CH_2)_d NHR^1$, $NHC(O)O(CH_2)_b(OCH_2CH_2)_c O(CH_2)_d NHR^1$, $NH(CH_2)_a NHC(O)(CH_2)_b(OCH_2CH_2)_c O(CH_2)_d NHR^1$, $NHC(O)(CH_2)_a NHR^1$, $NH(CH_2)_a NHR^1$, and $NHR^1$. In these formulae, the indices a, b and d are independently selected from the integers from 0 to 20, preferably from 1 to 5. The index c is an integer from 1 to 2500.

In an illustrative embodiment, G is sialic acid and selected compounds of the invention have the formulae:

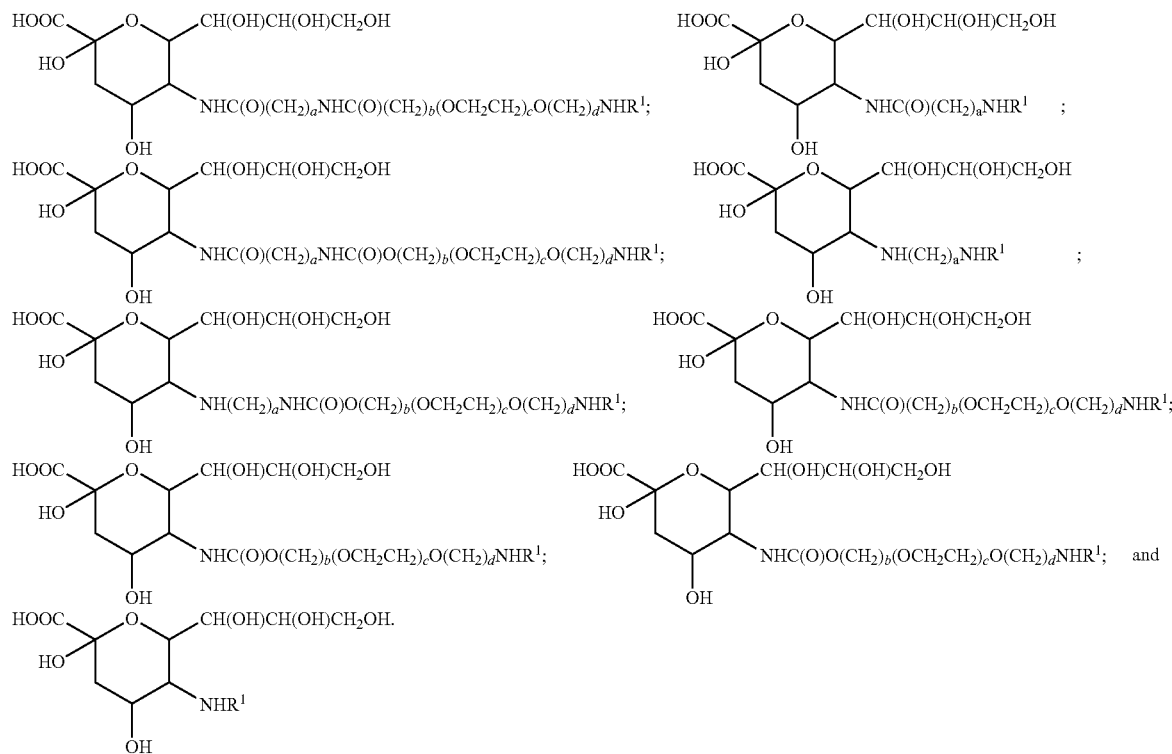

PEG is to the glycosyl group through the amino acid residue at one PEG terminus and bound to $R^1$ through the other PEG terminus. Alternatively, the amino acid residue is bound to $R^1$ and the PEG terminus not bound to the amino acid is bound to the glycosyl group.

An exemplary species for NH-L-R' has the formula: —$NH\{C(O)(CH_2)_a NH\}_s \{C(O)(CH_2)_b(OCH_2CH_2)_c O(CH_2)_d CH\} R^1$, in which the indices s and t are independently 0 or 1. The indices a, b and d are independently integers from 0 to 20, and c is an integer from 1 to 2500. Other similar linkers are As those of skill in the art will appreciate, the sialic acid moiety in the exemplary compounds above can be replaced with any other amino-saccharide including, but not limited to, glucosamine, galactosamine, mannosamine, their N-acetyl derivatives, and the like.

In another illustrative embodiment, a primary hydroxyl moiety of the sugar is functionalized with the modifying group. For example, the 9-hydroxyl of sialic acid can be converted to the corresponding amine and functionalized to provide a compound according to the invention. Formulae according to this embodiment include:

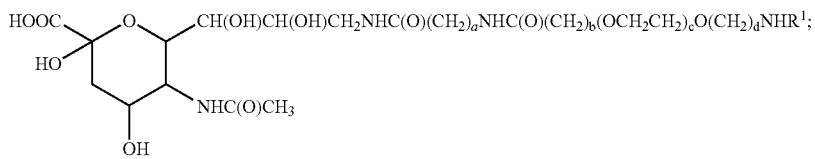

-continued

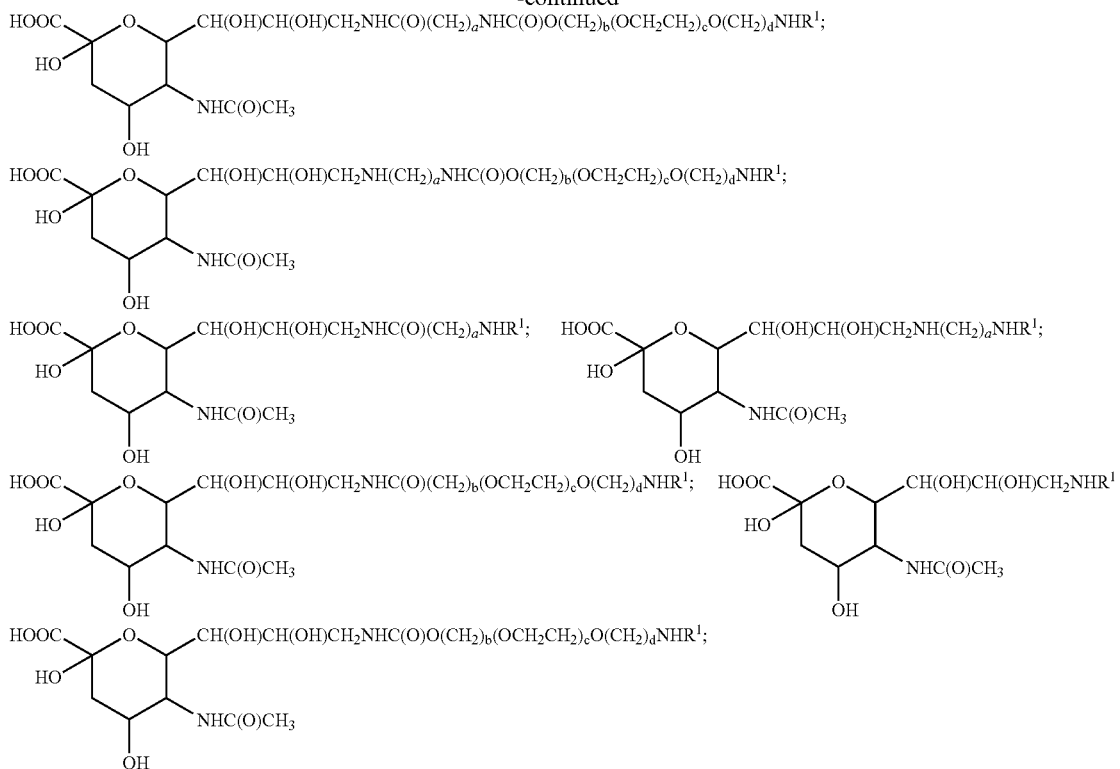

In a further exemplary embodiment, the invention provides a peptide conjugate comprising modified sugars in which the 6-hydroxyl position is converted to the corresponding amine moiety, which bears a linker-modifying group cassette such as those set forth above. Exemplary saccharyl groups that can be used as the core of these modified sugars include Gal, GalNAc, Glc, GlcNAc, Fuc, Xyl, Man, and the like. A representative modified sugar according to this embodiment has the formula:

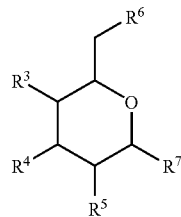

in which $R^3$-$R^5$ and $R^7$ are members independently selected from H, OH, C(O)CH$_3$, NH, and NH C(O)CH$_3$. $R^6$ is OR$^1$, NHR$^1$ or NH-L-R$^1$, which is as described above.

Selected conjugates of the invention are based on mannose, galactose or glucose, or on species having the stereochemistry of mannose, galactose or glucose. The general formulae of these conjugates are:

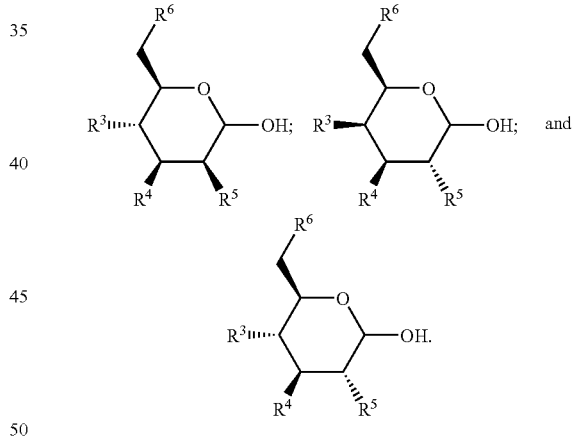

In another exemplary embodiment, the invention provides compounds as set forth above that are activated as the corresponding nucleotide sugars. Exemplary sugar nucleotides that are used in the present invention in their modified form include nucleotide mono-, di- or triphosphates or analogs thereof. In one embodiment, the modified sugar nucleotide is selected from a UDP-glycoside, CMP-glycoside, or a GDP-glycoside. Even more preferably, the sugar nucleotide portion of the modified sugar nucleotide is selected from UDP-galactose, UDP-galactosamine, UDP-glucose, UDP-glucosamine, GDP-mannose, GDP-fucose, CMP-sialic acid, or CMP-NeuAc. In an exemplary embodiment, the nucleotide phosphate is attached to C-1.

Thus, in an illustrative embodiment in which the glycosyl moiety is sialic acid, the invention provides peptide conjugates that are formed using compounds having the formulae:

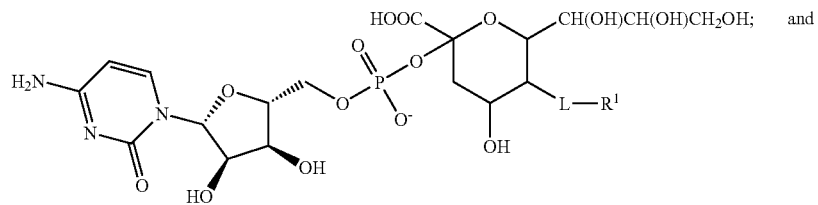

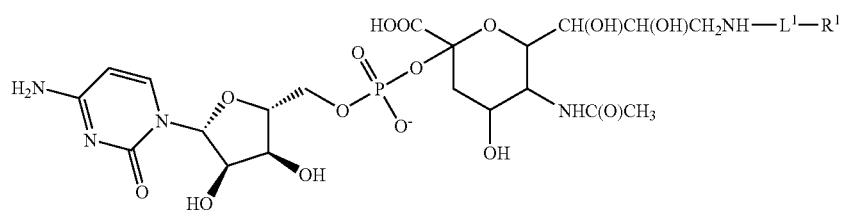

in which L-R$^1$ is as discussed above, and L$^1$-R$^1$ represents a linker bound to the modifying group. As with L, exemplary linker species according to L$^1$ include a bond, alkyl or heteroalkyl moieties.

In another exemplary embodiment, the invention provides a conjugate formed between a modified sugar of the invention and a substrate, e.g., a peptide, lipid, aglycone, etc., more particularly between a modified sugar and a glycosyl residue of a glycopeptide or a glycolipid. In this embodiment, the sugar moiety of the modified sugar becomes a glycosyl linking group interposed between the substrate and the modifying group. An exemplary glycosyl linking group is an intact glycosyl linking group, in which the glycosyl moiety or moieties forming the linking group are not degraded by chemical (e.g., sodium metaperiodate) or enzymatic processes (e.g., oxidase). Selected conjugates of the invention include a modifying group that is attached to the amine moiety of an aminosaccharide, e.g., mannosamine, glucosamine, galactosamine, sialic acid etc. Exemplary modifying group-intact glycosyl linking group cassette according to this motif is based on a sialic acid structure, such as that having the formulae:

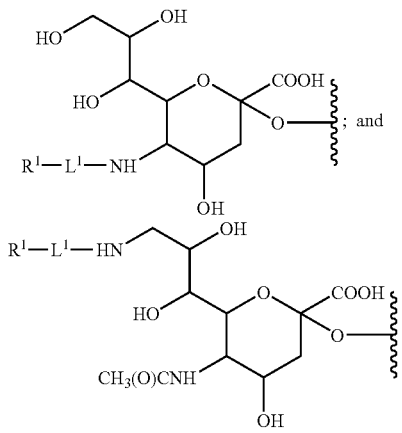

R$^1$, L$^1$ and L$^2$ are as described above.

In still a further exemplary embodiment, the conjugate is formed between a substrate and the 1-position of a saccharyl moiety that in which the modifying group is attached through a linker at the 6-carbon position of the saccharyl moiety. Thus, illustrative conjugates according to this embodiment have the formulae:

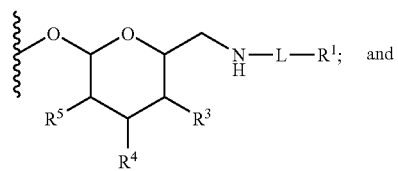

in which the radicals are as discussed above. Those of skill will appreciate that the modified saccharyl moieties set forth above can also be conjugated to a substrate at the 2, 3, 4, or 5 carbon atoms.

Illustrative compounds according to this embodiment include compounds having the formulae:

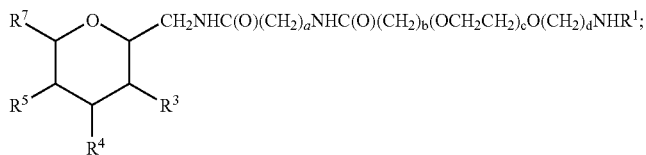

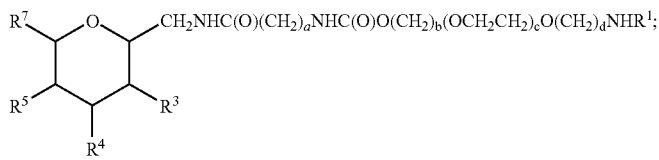

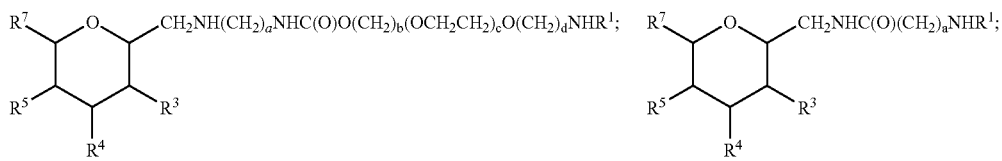

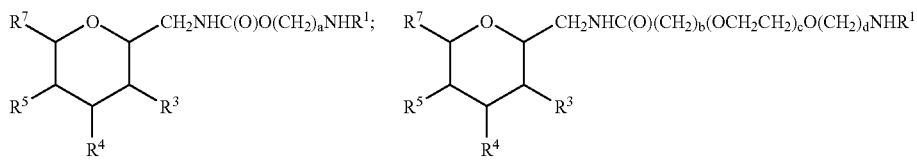

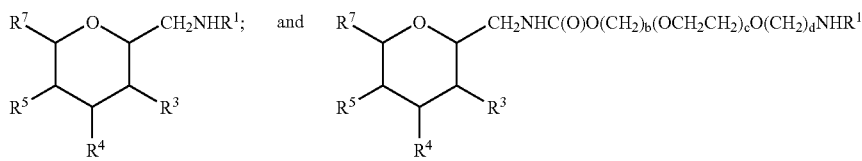

in which the R groups and the indices are as described above.

The invention also provides sugar nucleotides modified with L-R$^1$ at the 6-carbon position. Exemplary species according to this embodiment include:

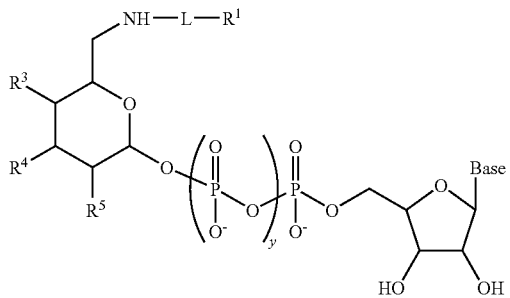

in which the R groups, and L, represent moieties as discussed above. The index "y" is 0, 1 or 2.

A further exemplary nucleotide sugar of the invention, based on a species having the stereochemistry of GDP mannose. An exemplary species according to this embodiment has the structure:

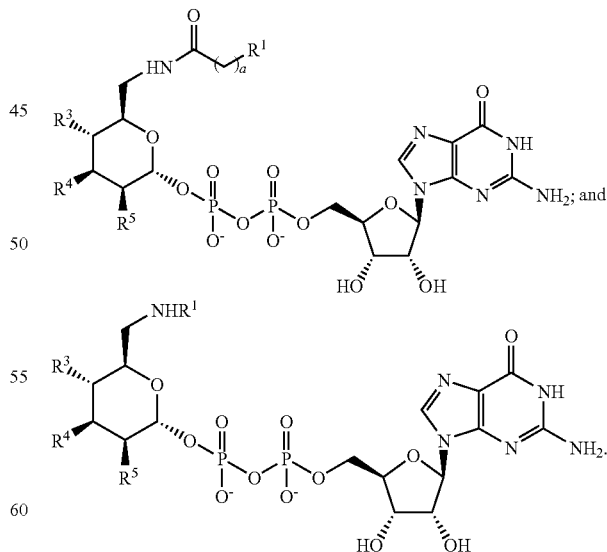

In a still further exemplary embodiment, the invention provides a conjugate, based on the stereochemistry of UDP galactose. An exemplary compound according to this embodiment has the structure:

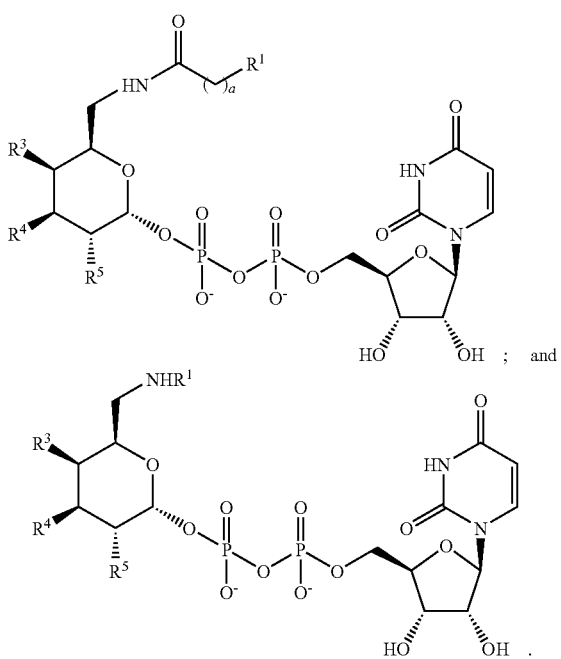

In another exemplary embodiment, the nucleotide sugar is based on the stereochemistry of glucose. Exemplary species according to this embodiment have the formulae:

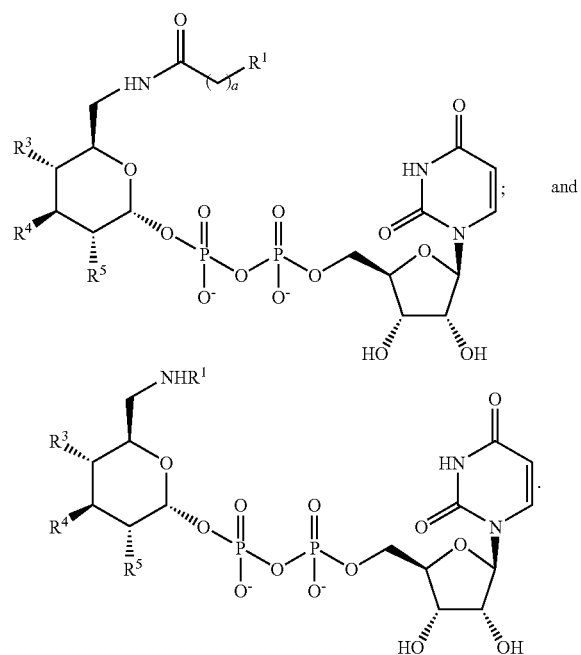

The modifying group, $R^1$, is any of a number of species including, but not limited to, water-soluble polymers, water-insoluble polymers, therapeutic agents, diagnostic agents and the like. The nature of exemplary modifying groups is discussed in greater detail herein below.

Water-Soluble Polymers

In some embodiments, the polymeric modifying groups of G-CSF conjugates of the invention are water-soluble polymers. These water-soluble polymers can be linear or branched polymers. In one embodiment, the water-soluble polymer has a molecular weight distribution that is essentially homodisperse.

In some embodiments, the conjugates of the invention comprise water-soluble polymers which are poly(ethylene glycol), e.g., methoxy-poly(ethylene glycol). The poly(ethylene glycol) used in the present invention is not restricted to any particular form or molecular weight range. For unbranched poly(ethylene glycol) molecules the molecular weight is preferably between 500 and 100,000. A molecular weight of 2,000-60,000 is preferably used and more preferably of from about 5,000 to about 30,000.

In another embodiment the poly(ethylene glycol) is a branched PEG having more than one PEG moiety attached. Examples of branched PEGs are described in U.S. Pat. No. 5,932,462; U.S. Pat. No. 5,342,940; U.S. Pat. No. 5,643,575; U.S. Pat. No. 5,919,455; U.S. Pat. No. 6,113,906; U.S. Pat. No. 5,183,660; WO 02/09766; Kodera Y., *Bioconjugate Chemistry* 5: 283-288 (1994); and Yamasaki et al., *Agric. Biol. Chem.*, 52: 2125-2127, 1998. Other useful branched PEG structures are disclosed herein.

In an exemplary embodiment the molecular weight of each poly(ethylene glycol) of the branched PEG is equal to or greater than about 2,000, 5,000, 10,000, 15,000, 20,000, 40,000 or 60,000 Daltons.

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly(amino acids), e.g., poly(aspartic acid) and poly(glutamic acid); nucleic acids; synthetic polymers (e.g., poly(acrylic acid), poly (ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

In one embodiment of the invention, water-soluble polymers utilized are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie*, 57:5-29 (2002). Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine).

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly(ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a protein or peptide, forming conjugates between the poly(ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

The art-recognized methods of polymer activation set forth above are of use in the context of the present invention in the formation of the branched polymers set forth herein and also for the conjugation of these branched polymers to other species, e.g., sugars, sugar nucleotides and the like.

Exemplary poly(ethylene glycol) molecules of use in the invention include, but are not limited to, those having the formula:

in which $R^8$ is H, OH, $NH_2$, substituted or unsubstituted alkyl, substituted or unsubstituted aryl, substituted or unsubstituted heteroaryl, substituted or unsubstituted heterocycloalkyl, substituted or unsubstituted heteroalkyl, e.g., acetal, OHC—, $H_2N$—$(CH_2)_q$—, HS—$(CH_2)_q$—, or —$(CH_2)_qC(Y)Z^1$. The index "e" represents an integer from 1 to 2500. The indices b, d, and q independently represent integers from 0 to 20. The symbols Z and $Z^1$ independently represent OH, $NH_2$, leaving groups, e.g., imidazole, p-nitrophenyl, HOBT, tetrazole, halide, S—$R^9$, the alcohol portion of activated esters; —$(CH_2)_pC(Y^1)V$, or —$(CH_2)_pU(CH_2)_sC(Y^1)_v$. The symbol Y represents H(2), =O, =S, =N—$R^{10}$. The symbols X, Y, $Y^1$, $A^1$, and U independently represent the moieties O, S, N—$R^{11}$. The symbol V represents OH, $NH_2$, halogen, S—$R^{12}$, the alcohol component of activated esters, the amine component of activated amides, sugar-nucleotides, and proteins. The indices p, q, s and v are members independently selected from the integers from 0 to 20. The symbols $R^9$, $R^{10}$, $R^{11}$ and $R^{12}$ independently represent H, substituted or unsubstituted alkyl, substituted or unsubstituted heteroalkyl, substituted or unsubstituted aryl, substituted or unsubstituted heterocycloalkyl and substituted or unsubstituted heteroaryl.

In other exemplary embodiments, the poly(ethylene glycol) molecule is selected from the following:

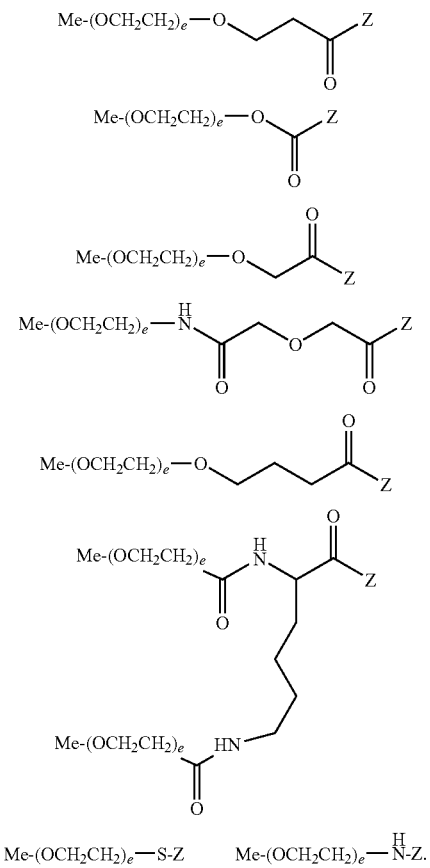

The poly(ethylene glycol) useful in forming the conjugate of the invention is either linear or branched. Branched poly(ethylene glycol) molecules suitable for use in the invention include, but are not limited to, those described by the following formula:

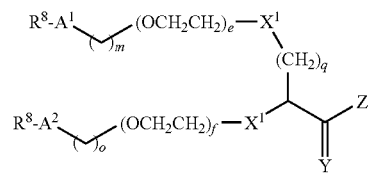

in which $R^8$ and $R^{8'}$ are members independently selected from the groups defined for $R^8$, above. $A^1$ and $A^2$ are members independently selected from the groups defined for $A^1$, above. The indices e, f, o, and q are as described above. Z and Y are as described above. $X^1$ and $X^{1'}$ are members independently selected from S, SC(O)NH, HNC(O)S, SC(O)O, O, NH, NHC(O), (O)CNH and NHC(O)O, OC(O)NH.

In other exemplary embodiments, the branched PEG is based upon a cysteine, serine or di-lysine core. Thus, further exemplary branched PEGs include:

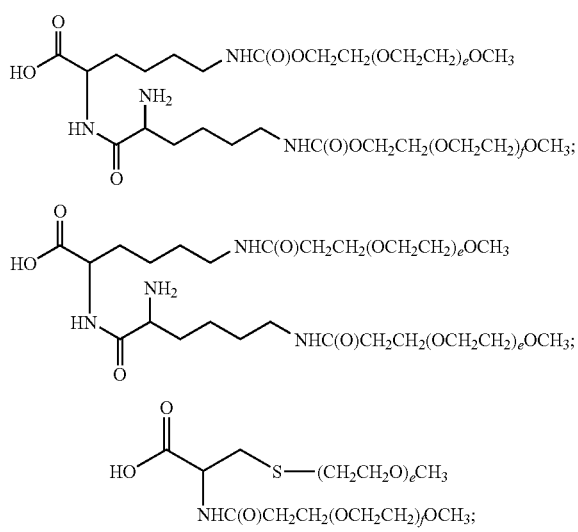

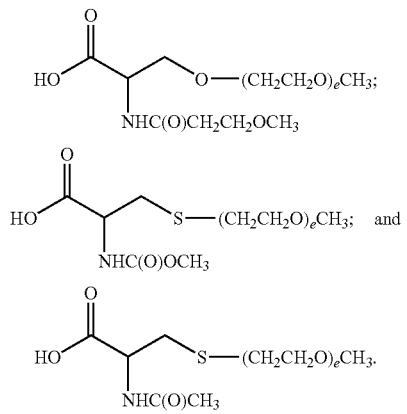

In yet another embodiment, the branched PEG moiety is based upon a tri-lysine peptide. The tri-lysine can be mono-, di-, tri-, or tetra-PEG-ylated. Exemplary species according to this embodiment have the formulae:

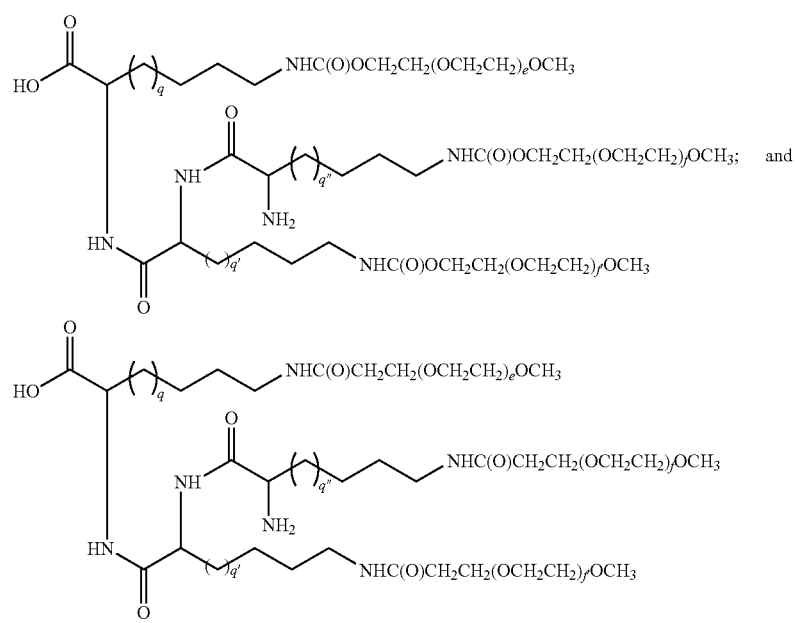

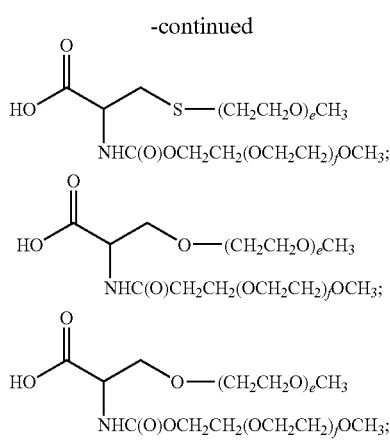

in which e, f and f' are independently selected integers from 1 to 2500; and q, q' and q" are independently selected integers from 1 to 20.

In exemplary embodiments of the invention, the PEG is m-PEG (5 kD, 10 kD, or 20 kD). An exemplary branched PEG species is a serine- or cysteine-(m-PEG)$_2$ in which the m-PEG is a 20 kD m-PEG.

As will be apparent to those of skill, the branched polymers of use in the invention include variations on the themes set forth above. For example the di-lysine-PEG conjugate shown above can include three polymeric subunits, the third bonded to the α-amine shown as unmodified in the structure above. Similarly, the use of a tri-lysine functionalized with three or four polymeric subunits is within the scope of the invention.

Specific embodiments according to the invention include:

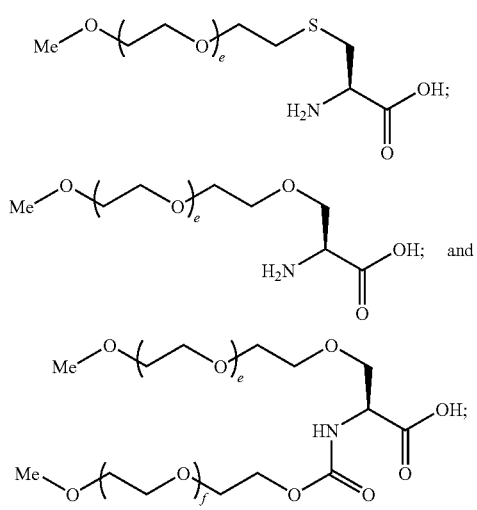

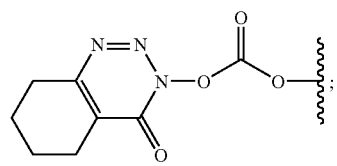

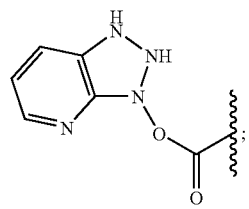

and carbonates and active esters of these species, such as:

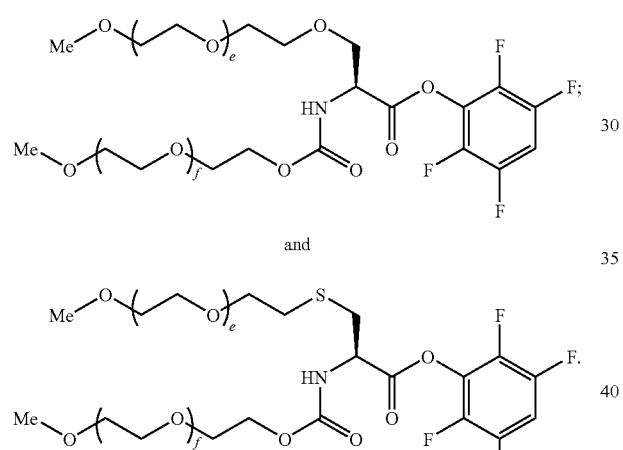

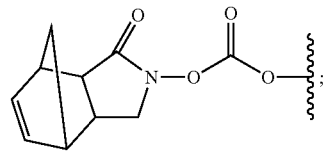

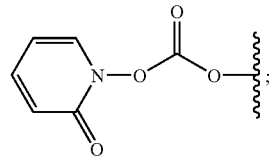

and

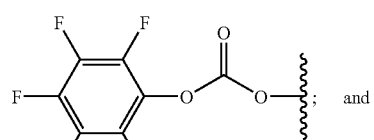; and

Other activating, or leaving groups, appropriate for activating linear PEGs of use in preparing the compounds set forth herein include, but are not limited to the species:

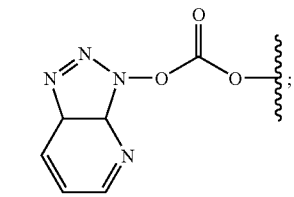

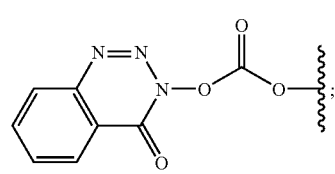

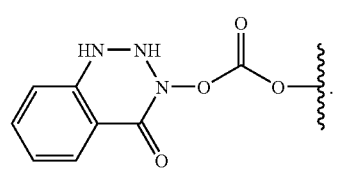

PEG molecules that are activated with these and other species and methods of making the activated PEGs are set forth in WO 04/083259.

Those of skill in the art will appreciate that one or more of the m-PEG arms of the branched polymer can be replaced by a PEG moiety with a different terminus, e.g., OH, COOH, $NH_2$, $C_2$-$C_{10}$-alkyl, etc. Moreover, the structures above are readily modified by inserting alkyl linkers (or removing carbon atoms) between the α-carbon atom and the functional group of the side chain. Thus, "homo" derivatives and higher homologues, as well as lower homologues are within the scope of cores for branched PEGs of use in the present invention.

The branched PEG species set forth herein are readily prepared by methods such as that set forth in the scheme below:

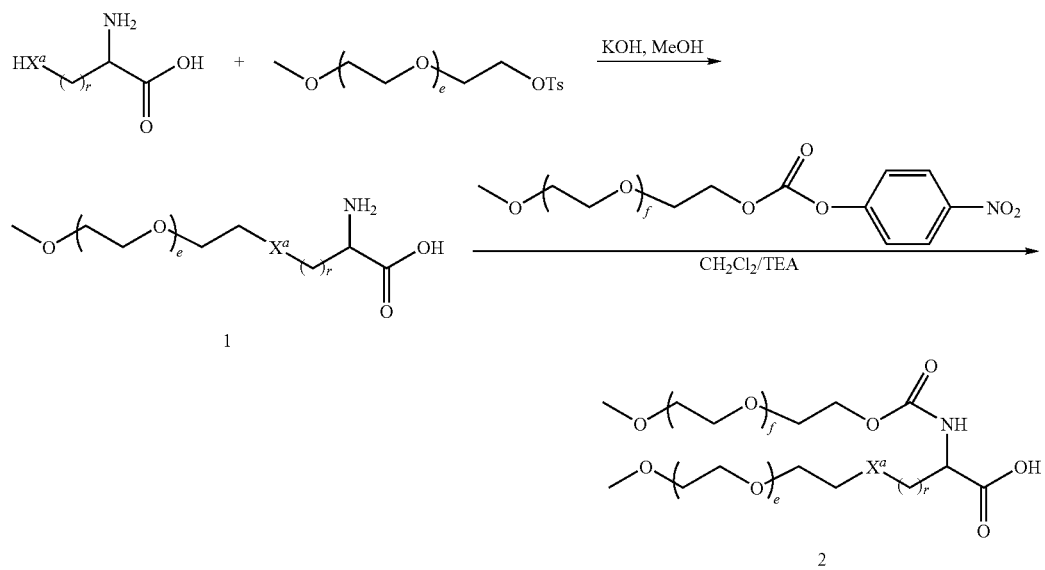

in which $X^a$ is O or S and r is an integer from 1 to 5. The indices e and f are independently selected integers from 1 to 2500.

Thus, according to this scheme, a natural or unnatural amino acid is contacted with an activated m-PEG derivative, in this case the tosylate, forming 1 by alkylating the side-chain heteroatom $X^a$. The mono-functionalized m-PEG amino acid is submitted to N-acylation conditions with a reactive m-PEG derivative, thereby assembling branched m-PEG 2. As one of skill will appreciate, the tosylate leaving group can be replaced with any suitable leaving group, e.g., halogen, mesylate, triflate, etc. Similarly, the reactive carbonate utilized to acylate the amine can be replaced with an active ester, e.g., N-hydroxysuccinimide, etc., or the acid can be activated in situ using a dehydrating agent such as dicyclohexylcarbodiimide, carbonyldiimidazole, etc.

In an exemplary embodiment, the modifying group is a PEG moiety, however, any modifying group, e.g., water-soluble polymer, water-insoluble polymer, therapeutic moiety, etc., can be incorporated in a glycosyl moiety through an appropriate linkage. The modified sugar is formed by enzymatic means, chemical means or a combination thereof, thereby producing a modified sugar. In an exemplary embodiment, the sugars are substituted with an active amine at any position that allows for the attachment of the modifying moiety, yet still allows the sugar to function as a substrate for an enzyme capable of coupling the modified sugar to the G-CSF peptide. In an exemplary embodiment, when galactosamine is the modified sugar, the amine moiety is attached to the carbon atom at the 6-position.

The in vivo half-life of therapeutic glycopeptides can also be enhanced with PEG moieties such as polyethylene glycol (PEG). For example, chemical modification of proteins with PEG (PEGylation) increases their molecular size and decreases their surface- and functional group-accessibility, each of which are dependent on the size of the PEG attached to the protein. This results in an improvement of plasma half-lives and in proteolytic-stability, and a decrease in immunogenicity and hepatic uptake (Chaffee et al. *J. Clin. Invest.* 89: 1643-1651 (1992); Pyatak et al. *Res. Commun. Chem. Pathol Pharmacol.* 29: 113-127 (1980)). PEGylation of interleukin-2 has been reported to increase its antitumor potency in vivo (Katre et al. *Proc. Natl. Acad. Sci. USA.* 84: 1487-1491 (1987)) and PEGylation of a F(ab')2 derived from the monoclonal antibody A7 has improved its tumor localization (Kitamura et al. *Biochem. Biophys. Res. Commun.* 28: 1387-1394 (1990)). Thus, in another embodiment, the in vivo half-life of a peptide derivatized with a PEG moiety by a method of the invention is increased relevant to the in vivo half-life of the non-derivatized peptide.

The increase in peptide in vivo half-life is best expressed as a range of percent increase in this quantity. The lower end of the range of percent increase is about 40%, about 60%, about 80%, about 100%, about 150% or about 200%. The upper end of the range is about 60%, about 80%, about 100%, about 150%, or more than about 250%.

G-CSF Peptide

Essentially any Granulocyte Colony Stimulating Factor peptide or agent, having any sequence, is of use as the peptide component of the conjugates of the present invention. Granulocyte Colony Stimulating Factor has been cloned and sequenced. In an exemplary embodiment, the G-CSF peptide has the sequence presented in SEQ ID NO:1:

```
                                               (SEQ ID NO: 1)
MTPLGPASSLPQSFLLKCLEQVRKIQGDGAALQEKLCATYKLCHPEELVL

LGHSLGIPWAPLSSCPSQALQLAGCLSQLHSGLFLYQGLLQALEGISPEL

GPTLDTLQLDVADFATTIWQQMEELGMAPALQPTQGAMPAFASAFQRRAG

GVLVASHLQSFLEVSYRVLRHLAQP.
```

In another exemplary embodiment, the G-CSF peptide has the sequence presented in SEQ ID NO:2:

```
                                               (SEQ ID NO: 2)
TPLGPASSLPQSFLLKCLEQVRKIQGDGAALQEKLCATYKLCHPEELVLL

GHSLGIPWAPLSSCPSQALQLAGCLSQLHSGLFLYQGLLQALEGISPELG

PTLDTLQLDVADFATTIWQQMEELGMAPALQPTQGAMPAFASAFQRRAGG

VLVASHLQSFLEVSYRVLRHLAQP.
```

In other exemplary embodiments, the G-CSF peptide has a sequence presented in SEQ ID Nos:3-11, below.

(SEQ ID NO: 3)
MTPLGPASSLPQSFLLKCLEQVRKIQGDGAALQEKLVSECATYKLCHPEE
LVLLGHSLGIPWAPLSSCPSQALQLAGCLSQLHSGLFLYQGLLQALEGIS
PELGPTLDTLQLDVADFATTIWQQMEELGMAPALQPTQGAMPAFASAFQR
RAGGVLVASHLQSFLEVSYRVLRHLAQP (SEQ ID NO: 4)
MAGPATQSPMKLMALQLLLWHSALWTVQEATPLGPASSLPQSFLLKCLEQ
VRKIQGDGAALQEKLCATYKLCHPEELVLLGHSLGIPWAPLSSCPSQALQ
LAGCLSQLHSGLFLYQGLLQALEGISPELGPTLDTLQLDVADFATTIWQQ
MEELGMAPALQPTQGAMPAFASAFQRRAGGVLVASHLQSFLEVSYRVLRH
LAQP (SEQ ID NO: 5)
MAGPATQSPMKLMALQLLLWHSALWTVQEATPLGPASSLPQSFLLKCLEQ
VRKIQGDGAALQEKLVSECATYKLCHPEELVLLGHSLGIPWAPLSSCPSQ
ALQLAGCLSQLHSGLFLYQGLLQALEGISPELGPTLDTLQLDVADFATTI
WQQMEELGMAPALQPTQGAMPAFASAFQRRAGGVLVASHLQSFLEVSYRV
LRHLAQP (SEQ ID NO: 6)
MVTPLGPASSLPQSFLLKCLEQVRKIQGDGAALQEKLCATYKLCHPEELV
LLGHTLGIPWAPLSSCPSQALQLAGCLSQLHSGLFLYQGLLQALEGISPE
LGPTLDTLQLDVADFATTIWQQMEELGMAPALQPTQGAMPAFASAFQRRA
GGVLVASHLQSFLEVSYRVLRHLAQP;

(SEQ ID NO: 7)
MTPLGPASSLPQSFLLKCLEQVRKIQGDGAALQEKLCATYKLCHPEELVL
LGHTLGIPWAPLSSCPSQALQLAGCLSQLHSGLFLYQGLLQALEGISPEL
GPTLDTLQLDVADFATTIWQQMEELGMAPALQPTQGAMPAFASAFQRRAG
GVLVASHLQSFLEVSYRVLRHLAQP;

(SEQ ID NO: 8)
MVTPLGPASSLPQSFLLKCLEQVRKIQGDGAALQEKLCATYKLCHPEELV
LLGSSLGIPWAPLSSCPSQALQLAGCLSQLHSGLFLYQGLLQALEGISPE
LGPTLDTLQLDVADFATTIWQQMEELGMAPALQPTQGAMPAFASAFQRRA
GGVLVASHLQSFLEVSYRVLRHLAQP;

(SEQ ID NO: 9)
MQTPLGPASSLPQSFLLKCLEQVRKIQGDGAALQEKLCATYKLCHPEELV
LLGHSLGIPWAPLSSCPSQALQLAGCLSQLHSGLFLYQGLLQALEGISPE
LGPTLDTLQLDVADFATTIWQQMEELGMAPALQPTQGAMPAFASAFQRRA
GGVLVASHLQSFLEVSYRVLRHLAQP;

(SEQ ID NO: 10)
MTPLGPASSLPQSFLLKCLEQVRKIQGDGAALQEKLCATYKLCHPEELVL
LGHSLGIPWAPLSSCPSQALQLAGCLSQLHSGLFLYQGLLQALEGISPEL
GPTLDTLQLDVADFATTIWQQMEELGMAPALQPTQGAMPAFASAFQRRAG
GVLVASHLQSFLEVSYRVLRHLAQPTQGAMP;
and (SEQ ID NO: 11)
MTPLGPASSLPQSFLLKCLEQVRKIQGDGAALQEKLCATYKLCHPEELVL
LGSSLGIPWAPLSSCPSQALQLAGCLSQLHSGLFLYQGLLQALEGISPEL
GPTLDTLQLDVADFATTIWQQMEELGMAPTTTPTQTAMPAFASAFQRRAG
GVLVASHLQSFLEVSYRVLRHLAQP The present invention is in no way limited to the sequences set forth herein.

In an exemplary embodiment, the G-CSF peptides of the invention include at least one O-linked glycosylation site, which is glycosylated with a glycosyl residue that includes a PEG moiety. The PEG is covalently attached to the G-CSF peptide via an intact glycosyl linking group. The glycosyl linking group is covalently attached to either an amino acid residue or a glycosyl residue of the G-CSF peptide. Alternatively, the glycosyl linking group is attached to one or more glycosyl units of a glycopeptide. The invention also provides conjugates in which the glycosyl linking group is attached to both an amino acid residue and a glycosyl residue.

The PEG moiety is attached to an intact glycosyl linker directly, or via a non-glycosyl linker, e.g., substituted or unsubstituted alkyl, substituted or unsubstituted heteroalkyl.

In an exemplary embodiment, the G-CSF peptide comprises a moiety having the formula of Formula I.

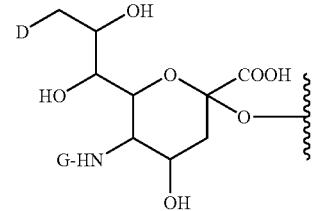

Formula I in which D is a member selected from —OH and $R^1$-L-HN—; G is a member selected from $R^1$-L- and —C(O)($C_1$-$C_6$)alkyl; $R^1$ is a moiety comprising a member selected a moiety comprising a straight-chain or branched poly(ethylene glycol) residue; and L is a linker which is a member selected from a bond, substituted or unsubstituted alkyl and substituted or unsubstituted heteroalkyl, such that when D is OH, G is $R^1$-L-, and when G is C(O)($C_1$-$C_6$)alkyl, D is $R^1$-L-NH—. In the modified sialic acid structures set forth herein, COOH also represents COO⁻ and/or a salt thereof.

In one embodiment, a $R^1$-L has the formula:

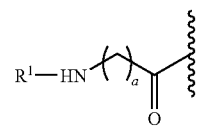

wherein a is an integer from 0 to 20.

In an exemplary embodiment, $R^1$ has a structure that is a member selected from:

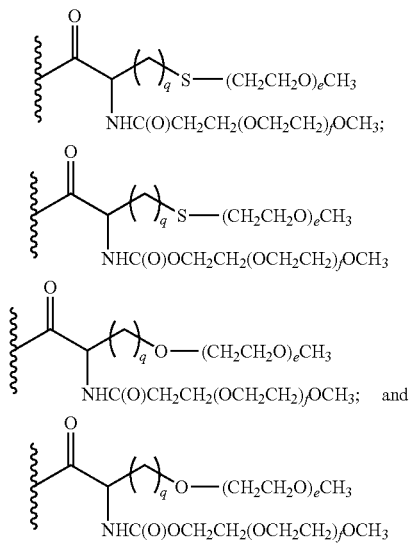

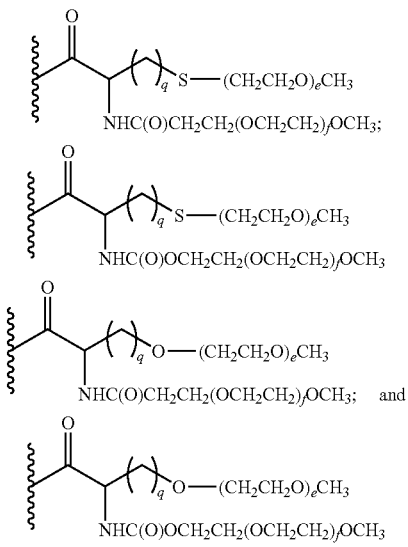

wherein e and f are integers independently selected from 1 to 2500; and q is an integer from 1 to 20. In other embodiments $R^1$ has a structure that is a member selected from:

wherein e and f are integers independently selected from 1 to 2500; and q is an integer from 1 to 20. In other embodiments $R^1$ has a structure that is a member selected from:

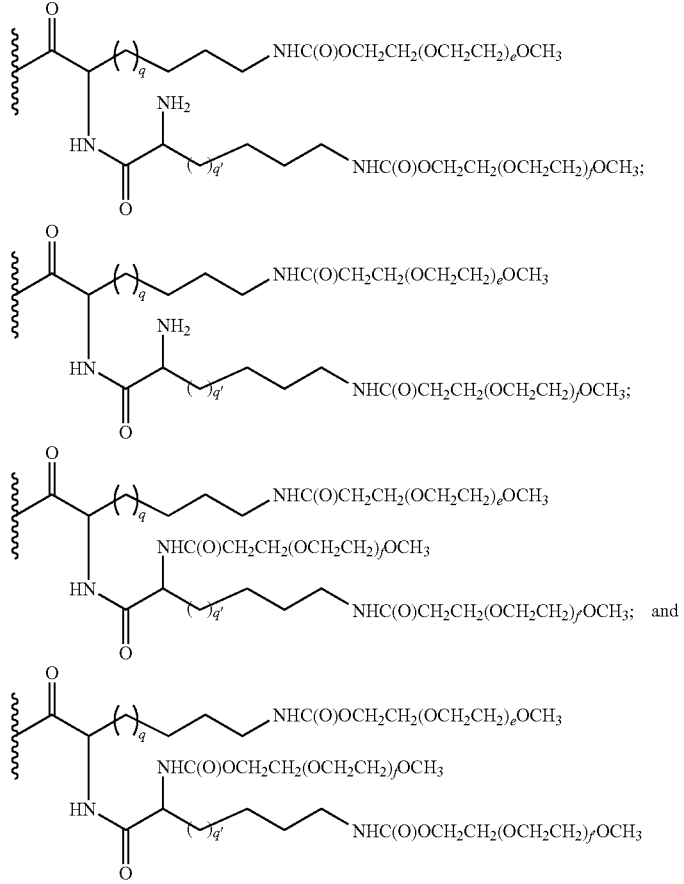

wherein e, f and f' are integers independently selected from 1 to 2500; and q and q' are integers independently selected from 1 to 20.

In still another embodiment, the invention provides a G-CSF peptide conjugate wherein $R^1$ has a structure that is a member selected from:

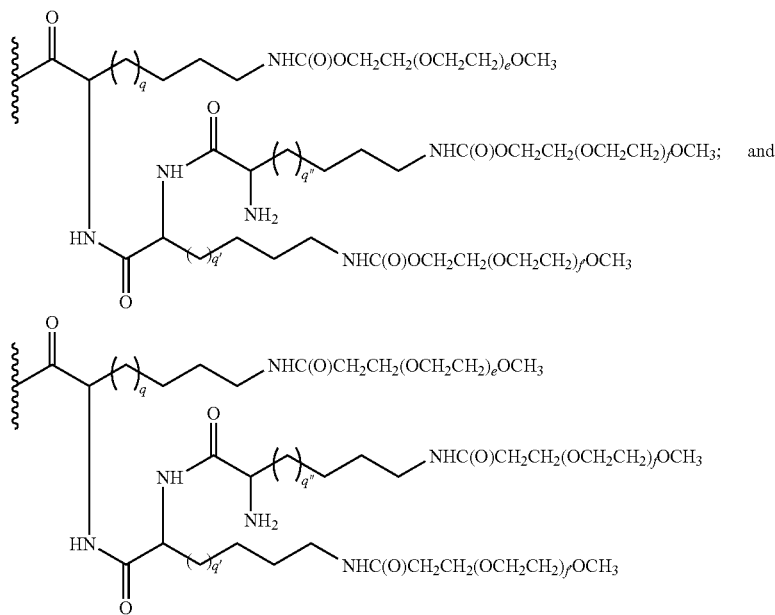

wherein e, f and f' are integers independently selected from 1 to 2500; and q, q' and q" are integers independently selected from 1 to 20.

In other embodiments, $R^1$ has a structure that is a member selected from:

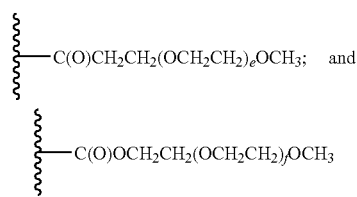

wherein e and f are integers independently selected from 1 to 2500.

In another exemplary embodiment, the invention provides a peptide comprising a moiety having the formula:

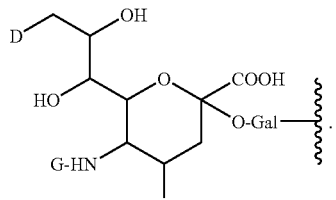

The Gal can be attached to an amino acid or to a glycosyl residue that is directly or indirectly (e.g., through a glycosyl residue) attached to an amino acid.

In other embodiments, the moiety has the formula:

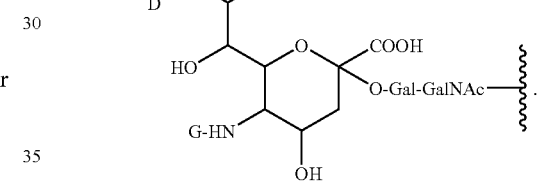

The GalNAc can be attached to an amino acid or to a glycosyl residue that is directly or indirectly (e.g., through a glycosyl residue) attached to an amino acid.

In a still further exemplary embodiment the peptide comprises a moiety according to the formula

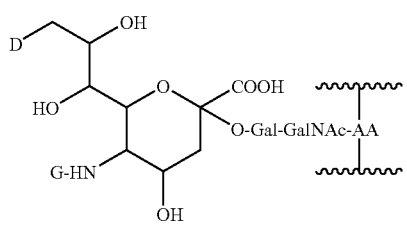

wherein AA is an amino acid residue of said peptide and, in each of the above structures, D and G are as described herein.

An exemplary amino acid residue of the G-CSF peptide at which one or more of the above species can be conjugated include serine and threonine, e.g., threonine 133 of SEQ. ID. NO.: 1.

In another exemplary embodiment, the invention provides a G-CSF conjugate that includes a glycosyl residue having the formula:

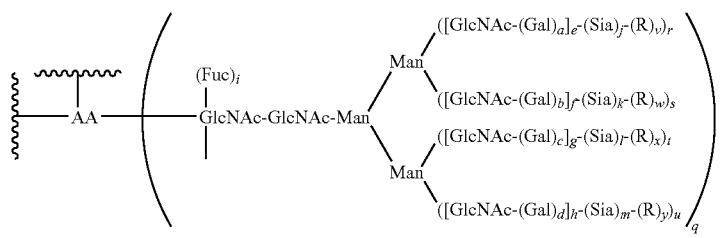

wherein a, b, c, d, i, r, s, t, and u are integers independently selected from 0 and 1. The index q is 1. The indices e, f, g, and h are independently selected from the integers from 0 to 6. The indices j, k, l, and m are independently selected from the integers from 0 and 100. The indices v, w, x, and y are independently selected from 0 and 1, and at least one of v, w, x and y is 1. The symbol AA represents an amino acid residue of the G-CSF peptide.

The symbol Sia-(R) represents a group that has the formula:

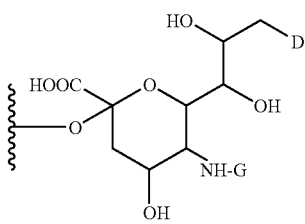

wherein D is selected from —OH and $R^1$-L-HN—. The symbol G is represents $R^1$-L- or —C(O)($C_1$-$C_6$)alkyl. $R^1$ represents a moiety that includes a straight-chain or branched poly(ethylene glycol) residue. L is a linker which is a member selected from a bond, substituted or unsubstituted alkyl and substituted or unsubstituted heteroalkyl. In general, when D is OH, G is $R^1$-L-, and when G is —C(O)($C_1$-$C_6$)alkyl, D is $R^1$-L-NH—.

In another exemplary embodiment, the PEG-modified sialic acid moiety in the conjugate of the invention has the formula:

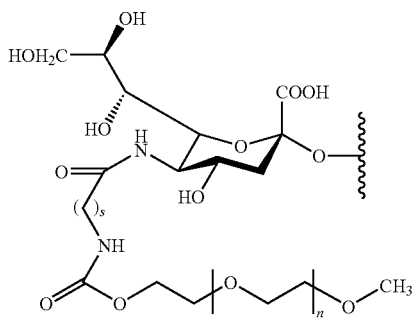

in which the index "s" represents an integer from 0 to 20, and n is an integer from 1 to 2500. In one embodiment, s is equal to 1; and the m-PEG moiety has a molecular weight of about 20 kD.

In a still further exemplary embodiment, the PEG-modified sialic acid in has the formula:

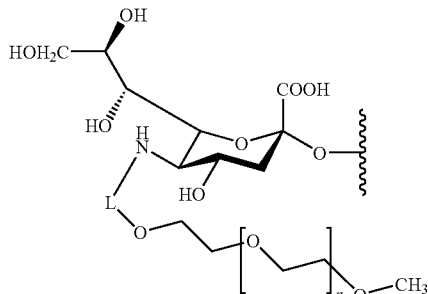

in which L is a substituted or unsubstituted alkyl or substituted or unsubstituted heteroalkyl linker moiety joining the sialic acid moiety and the PEG moiety.

In one embodiment, at least two, more preferably three, more preferably four of the above-named asparagine residues is functionalized with the N-linked glycan chain shown above.

The conjugates of the invention include intact glycosyl linking groups that are mono- or multi-valent (e.g., antennary structures). Thus, conjugates of the invention include both species in which a selected moiety is attached to a peptide via a monovalent glycosyl linking group and a multivalent linking group. Also included within the invention are conjugates in which more than one selected moiety is attached to a peptide via a multivalent linking group.

Water-Insoluble Polymers

In another embodiment, analogous to those discussed above, the modified sugars include a water-insoluble polymer, rather than a water-soluble polymer. The conjugates of the invention may also include one or more water-insoluble polymers. This embodiment of the invention is illustrated by the use of the conjugate as a vehicle with which to deliver a therapeutic peptide in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

The motifs forth above for $R^1$, L-$R^1$, $R^{15}$, $R^{15'}$ and other radicals are equally applicable to water-insoluble polymers, which may be incorporated into the linear and branched structures without limitation utilizing chemistry readily accessible to those of skill in the art.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly (isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly(ethylene terephthalate), poly(vinyl acetate), polyvinyl chloride, polystyrene, polyvinyl pyrrolidone, pluronics and polyvinylphenol and copolymers thereof.

Synthetically modified natural polymers of use in conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

Representative biodegradable polymers of use in the conjugates of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid" polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly($\alpha$-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., J. Biomed. Mater. Res. 21: 1301-1316 (1987); and Cohn et al., J. Biomed. Mater. Res. 22: 993-1009 (1988).

Presently preferred bioresorbable polymers include one or more components selected from poly(esters), poly(hydroxy acids), poly(lactones), poly(amides), poly(ester-amides), poly(amino acids), poly(anhydrides), poly(orthoesters), poly (carbonates), poly(phosphazines), poly(phosphoesters), poly (thioesters), polysaccharides and mixtures thereof. More preferably still, the biosresorbable polymer includes a poly (hydroxy) acid component. Of the poly(hydroxy) acids, polylactic acid, polyglycolic acid, polycaproic acid, polybutyric acid, polyvaleric acid and copolymers and mixtures thereof are preferred.

In addition to forming fragments that are absorbed in vivo ("bioresorbed"), preferred polymeric coatings for use in the methods of the invention can also form an excretable and/or metabolizable fragment.

Higher order copolymers can also be used in the present invention. For example, Casey et al., U.S. Pat. No. 4,438,253, which issued on Mar. 20, 1984, discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other polymers based on lactic and/or glycolic acids can also be utilized. For example, Spinu, U.S. Pat. No. 5,202,413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a difunctional compound, such as, a diisocyanate, diacylchloride or dichlorosilane.

Bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

When placed within the body, the hydrophilic region can be processed into excretable and/or metabolizable fragments. Thus, the hydrophilic region can include, for example, polyethers, polyalkylene oxides, polyols, poly(vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene)oxide. Such poly(alkylene) oxides can include, for example, poly(ethylene)oxide, poly (propylene)oxide and mixtures and copolymers thereof.

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. No. 5,410,016, which issued on Apr. 25, 1995 and U.S. Pat. No. 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly(ethylene glycol); whereas, the hydrolytically labile extensions can be a poly($\alpha$-hydroxy acid), such as polyglycolic acid or polylactic acid. See, Sawhney et al., *Macromolecules* 26: 581-587 (1993).

In another preferred embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, is of use in the present invention.

The structural formats discussed above in the context of the water-soluble polymers, both straight-chain and branched are generally applicable with respect to the water-insoluble polymers as well. Thus, for example, the cysteine, serine, dilysine, and trilysine branching cores can be functionalized with two water-insoluble polymer moieties. The methods used to produce these species are generally closely analogous to those used to produce the water-soluble polymers.

Methods for Preparing G-CSF Conjugates

In addition to the conjugates discussed above, the present invention provides methods for preparing these and other conjugates. Thus, in one aspect, the invention provides a method of forming a covalent conjugate between a selected moiety and a G-CSF peptide. Additionally, the invention provides methods for targeting conjugates of the invention to a particular tissue or region of the body.

In exemplary embodiments, the conjugate is formed between a PEG moiety (or an enzymatically transferable glycosyl moiety comprising a PEG moiety), and a glycosylated or non-glycosylated peptide. PEG is conjugated to the G-CSF peptide via an intact glycosyl linking group, which is interposed between, and covalently linked to both the G-CSF peptide and the PEG moiety, or to a PEG-non-glycosyl linker (e.g., substituted or unsubstituted alkyl, substituted or unsubstituted heteroalkyl) construct. The method includes contacting the G-CSF peptide with a mixture containing a modified sugar and a glycosyltransferase for which the modified sugar is a substrate. The reaction is conducted under conditions sufficient to form a covalent bond between the modified sugar and the G-CSF peptide. The sugar moiety of the modified sugar is selected from nucleotide sugars, activated sugars and sugars, which are neither nucleotides nor activated.

The acceptor peptide (glycosylated or non-glycosylated) is typically synthesized de novo, or recombinantly expressed in a prokaryotic cell (e.g., bacterial cell, such as *E. coli*) or in a eukaryotic cell such as a mammalian, yeast, insect, fungal or plant cell. The G-CSF peptide can be either a full-length protein or a fragment. Moreover, the G-CSF peptide can be a wild type or mutated peptide. In an exemplary embodiment, the G-CSF peptide includes a mutation that adds one or more N- or O-linked glycosylation sites to the peptide sequence.

In an exemplary embodiment, Factor IX is O-glycosylated and functionalized with a water-soluble polymer in the following manner. The peptide is either produced with an available amino acid glycosylation site or, if glycosylated, the glycosyl moiety is trimmed off to exposed the amino acid. For example, a serine or threonine is $\alpha$-1 N-acetyl amino galactosylated (GalNAc) and the NAc-galactosylated peptide is sialylated with a sialic acid-modifying group cassette using ST6GalNAcT1. Alternatively, the NAc-galactosylated peptide is galactosylated using Core-1-GalT-1 and the product is sialylated with a sialic acid-modifying group cassette using ST3GalT1. An exemplary conjugate according to this method has the following linkages: Thr-$\alpha$-1-GalNAc-$\beta$-1,3-Gal-$\alpha$2,3-Sia*, in which Sia* is the sialic acid-modifying group cassette.

In the methods of the invention, such as that set forth above, using multiple enzymes and saccharyl donors, the individual glycosylation steps may be performed separately, or combined in a "single pot" reaction. For example, in the three enzyme reaction set forth above the GalNAc transferase, GalT and SiaT and their donors may be combined in a single vessel. Alternatively, the GalNAc reaction can be performed alone and both the GalT and SiaT and the appropriate saccharyl donors added as a single step. Another mode of running the reactions involves adding each enzyme and an appropriate donor sequentially and conducting the reaction in a "single pot" motif. Combinations of each of the methods set forth above are of use in preparing the compounds of the invention.

In the conjugates of the invention, particularly the glycopegylated N-linked glycans, the Sia-modifying group cassette can be linked to the Gal in an $\alpha$-2,6, or $\alpha$-2,3 linkage.

The methods of the invention also provide for modification of incompletely glycosylated peptides that are produced recombinantly. Employing a modified sugar in a method of the invention, the G-CSF peptide can be simultaneously further glycosylated and derivatized with, e.g., a PEG moiety, therapeutic agent, or the like. The sugar moiety of the modified sugar can be the residue that would properly be conjugated to the acceptor in a fully glycosylated peptide, or another sugar moiety with desirable properties.

G-CSF peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X- serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-acetylgalactosamine, galactose, mannose, GlcNAc, glucose, fucose or xylose) to a the hydroxy side chain of a hydroxyamino acid, preferably serine or threonine, although 5-hydroxyproline or 5-hydroxylysine may also be used.

In one exemplary embodiment, G-CSF is expressed in a mammalian system and modified by treatment of sialidase to trim back terminal sialic acid residues, followed by PEGylation using ST3Gal3 and a donor of PEG-sialic acid.

In another exemplary embodiment, G-CSF expressed in mammalian cells is first treated with sialidase to trim back terminal sialic acid residues, then PEGylated using ST3Gal3 and a donor of PEG-sialic acid, and then sialylated using ST3Gal3 and a sialic acid donor.

G-CSF expressed in a mammalian system can also be treated with sialidase and galactosidase to trim back its sialic acid and galactose residues, then galactosylated using a galactose donor and a galactosyltransferase, and then PEGylated using ST3Gal3 and a donor of PEG-sialic acid.

In yet another exemplary embodiment, the G-CSF is not first treated with sialidase, but is glycopegylated using a sialic acid transfer reaction with the modifying group-sialic acid cassette, and an enzyme such as ST3Gal3.

In a further exemplary embodiment, G-CSF is expressed in insect cells and modified in the following procedure: N-acetylglucosamine is first added to G-CSF using an appropriate N-acetylglucosamine donor and one or more of GnT-I, II, IV, and V; G-CSF is then PEGylated using a donor of PEG-galactose and a galactosyltransferase.

G-CSF produced in yeast can also be glycopegylated. For example, G-CSF is first treated with endoglycanase to trim back the glycosyl groups, galactosylated using a galactose donor and a galactosyltransferase, and is then PEGylated with ST3Gal3 and a donor of PEG-sialic acid.

Addition of glycosylation sites to a peptide or other structure is conveniently accomplished by altering the amino acid sequence such that it contains one or more glycosylation sites. The addition may also be made by the incorporation of one or more species presenting an —OH group, preferably serine or threonine residues, within the sequence of the G-CSF peptide (for O-linked glycosylation sites). The addition may be made by mutation or by full chemical synthesis of the G-CSF peptide. The G-CSF peptide amino acid sequence is preferably altered through changes at the DNA level, particularly by mutating the DNA encoding the peptide at preselected bases such that codons are generated that will translate into the desired amino acids. The DNA mutation(s) are preferably made using methods known in the art.

In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

The present invention also provides means of adding (or removing) one or more selected glycosyl residues to a peptide, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the G-CSF peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. Chemical deglycosylation is preferably brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal. Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876, 980, 6,030,815, 5,728,554, and 5,922,577.

Exemplary attachment points for selected glycosyl residue include, but are not limited to: (a) consensus sites for N- and O-glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC Crit. Rev. Biochem., pp. 259-306 (1981).

In an exemplary embodiment, the invention provides a method of making a PEG-ylated G-CSF comprising the moiety:

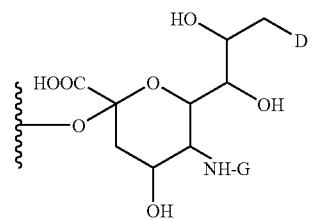

wherein D is —OH or $R^1$-L-HN—. The symbol G represents $R^1$-L- or —C(O)($C_1$-$C_6$)alkyl. $R^1$ is a moiety comprising a straight-chain or branched poly(ethylene glycol) residue. The symbol L represents a linker selected from a bond, substituted or unsubstituted alkyl and substituted or unsubstituted heteroalkyl. In general, when D is OH, G is $R^1$-L-, and when G is —C(O)($C_1$-$C_6$)alkyl, D is $R^1$-L-NH—. The method of the invention includes, (a) contacting a substrate G-CSF peptide with a PEG-sialic acid donor and an enzyme that is capable of transferring the PEG-sialic acid moiety from the donor to the substrate G-CSF peptide.

An exemplary PEG-sialic acid donor is a nucleotide sugar such as that having the formula:

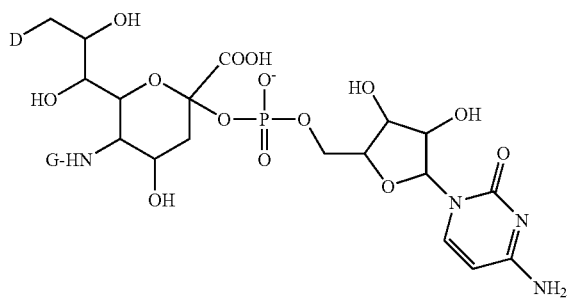

and an enzyme that transfers the PEG-sialic acid onto an amino acid or glycosyl residue of the G-CSF peptide, under conditions appropriate for the transfer.

In one embodiment the substrate G-CSF peptide is expressed in a host cell prior to the formation of the conjugate of the invention. An exemplary host cell is a mammalian cell. In other embodiments the host cell is an insect cell, plant cell, a bacteria or a fungi.

The method presented herein is applicable to each of the G-CSF conjugates set forth in the sections above.

G-CSF peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-acetylgalactosamine, galactose, mannose, GlcNAc, glucose, fucose or xylose) to the hydroxy side chain of a hydroxyamino acid, preferably serine or threonine, although unusual or non-natural amino acids, e.g., 5-hydroxyproline or 5-hydroxylysine may also be used.

Addition of glycosylation sites to a peptide or other structure can be accomplished in accordance with the present invention by altering the amino acid sequence such that it contains one or more glycosylation sites. Addition of glycosylation sites may also be accomplished by the incorporation of one or more species presenting an —OH group, preferably serine or threonine residues, within the sequence of the peptide (for O-linked glycosylation sites). The addition may be made by mutation or by full chemical synthesis of the peptide. The peptide amino acid sequence in in some embodiments altered through changes at the DNA level, particularly by mutating the DNA encoding the peptide at preselected bases such that codons are generated that will translate into the desired amino acids. The DNA mutation(s) are made using methods known in the art.

In an exemplary embodiment, a glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, Proc. Natl. Acad. Sci. USA 91:10747-10751 (1994); Stemmer, Nature 370:389-391 (1994); and U.S. Pat. Nos. 5,605, 793, 5,837,458, 5,830,721 and 5,811,238.

Exemplary methods of adding or removing glycosylation sites, and adding or removing glycosyl structures or substructures are described in detail in WO04/099231, WO03/031464 and related U.S. and PCT applications.

The present invention also utilizes means of adding (or removing) one or more selected glycosyl residues to a G-CSF peptide, after which a modified sugar is conjugated to at least one of the selected glycosyl residues of the peptide. Such techniques are useful, for example, when it is desired to conjugate the modified sugar to a selected glycosyl residue that is either not present on a G-CSF peptide or is not present in a desired amount. Thus, prior to coupling a modified sugar to a peptide, the selected glycosyl residue is conjugated to the G-CSF peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Exemplary attachment points for selected glycosyl residue include, but are not limited to: (a) consensus sites for N-linked glycosylation, and sites for O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC CRIT. REV. BIOCHEM., pp. 259-306 (1981).

In accordance with the present invention PEG modified sugars are conjugated to a glycosylated or non-glycosylated peptide using an appropriate enzyme to mediate the conjugation. Preferably, the concentrations of the modified donor sugar(s), enzyme(s) and acceptor peptide(s) are selected such that glycosylation proceeds until the desired degree of modification of the acceptor is achieved. It will be appreciated that the considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., Pure Appl. Chem. 65: 753 (1993), U.S. Pat. Nos. 5,352,670, 5,374,541, 5,545,553, and commonly owned U.S. Pat. Nos. 6,399,336, and 6,440,703 which are incorporated herein by reference.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In one embodiment, each of the first and second enzyme is a glycosyltransferase. In another preferred embodiment, one enzyme is an endoglycosidase. In another embodiment, more than two enzymes are used to assemble the modified glycoprotein of the invention. The enzymes are used to alter a saccharide structure on the G-CSF peptide at any point either before or after the addition of the modified sugar to the peptide.

In still another embodiment, methods of the invention utilize one or more exo- or endoglycosidase. The glycosidase can be a mutant and/or a variant, which forms or is engineered to form glycosyl bonds rather than rupture them. Such a mutant glycanase generally includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

Such a mutant enzyme can catalyze the reaction by a synthesis step that is analogous to the reverse reaction of the endoglycanase hydrolysis step. In such an embodiment, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In one embodiment, enzymes utilized to produce a conjugate of the invention are present in a catalytic amount. The catalytic amount of a particular enzyme varies according to the concentration of that enzyme's substrate as well as to reaction conditions such as temperature, time and pH. Means for determining the catalytic amount for a given enzyme under preselected substrate concentrations and reaction conditions are well known to those of skill in the art.

The temperature at which reactions according to the present invention are carried out can range from just above freezing to the temperature at which the most sensitive enzyme denatures. Preferred temperature ranges are about 0° C. to about 55° C., and more preferably about 20° C. to about 37° C. In another exemplary embodiment, one or more components of the present method are conducted at an elevated temperature using a thermophilic enzyme.

In one aspect, the reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art will appreciate that the rate of reaction is dependent on a number of variable factors (e.g., enzyme concentration, donor concentration, acceptor concentration, temperature, solvent volume), which are optimized for a selected system.

The present invention also provides for the industrial-scale production of modified peptides. As used herein, an "industrial scale" generally refers to the production of at least one gram of finished, purified conjugate.

In the discussion that follows, the invention is exemplified by the conjugation of modified sialic acid moieties to a glycosylated peptide. The exemplary modified sialic acid is labeled with PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than PEG including other PEG moieties, therapeutic moieties, and biomolecules.

An enzymatic approach can be used for the selective introduction of PEGylated or PPGylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the G-CSF peptide backbone, onto existing sugar residues of a glycopeptide or onto sugar residues that have been added to a peptide.

An acceptor for the sialyltransferase is present on the G-CSF peptide to be modified by the methods of the present invention either as a naturally occurring structure or one placed there recombinantly, enzymatically or chemically. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art (see, e.g., Paulson et al., *J. Biol. Chem.* 253: 5617-5624 (1978)).

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the G-CSF peptide to include an acceptor by methods known to those of skill in the art. In an exemplary embodiment, a GalNAc residue is added by the action of a GalNAc transferase.

In an exemplary embodiment, the galactosyl acceptor is assembled by attaching a galactose residue to an appropriate acceptor linked to the G-CSF peptide, e.g., a GlcNAc. The method includes incubating the G-CSF peptide to be modified with a reaction mixture that contains a suitable amount of a galactosyltransferase (e.g., galβ1,3 or galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions.

In the discussion that follows, the method of the invention is exemplified by the use of modified sugars having a PEG moiety attached thereto. The focus of the discussion is for clarity of illustration. Those of skill will appreciate that the discussion is equally relevant to those embodiments in which the modified sugar bears a therapeutic moiety, biomolecule or the like.

In an exemplary embodiment of the invention in which a carbohydrate residue is "trimmed" prior to the addition of the modified sugar high mannose is trimmed back to the first generation biantennary structure. A modified sugar bearing a PEG moiety is conjugated to one or more of the sugar residues exposed by the "trimming back." In one example, a PEG moiety is added via a GlcNAc moiety conjugated to the PEG moiety. The modified GlcNAc is attached to one or both of the terminal mannose residues of the biantennary structure. Alternatively, an unmodified GlcNAc can be added to one or both of the termini of the branched species.

In another exemplary embodiment, a PEG moiety is added to one or both of the terminal mannose residues of the biantennary structure via a modified sugar having a galactose residue, which is conjugated to a GlcNAc residue added onto the terminal mannose residues. Alternatively, an unmodified Gal can be added to one or both terminal GlcNAc residues.

In yet a further example, a PEG moiety is added onto a Gal residue using a modified sialic acid.

In another exemplary embodiment, a high mannose structure is "trimmed back" to the mannose from which the biantennary structure branches. In one example, a PEG moiety is added via a GlcNAc modified with the polymer. Alternatively, an unmodified GlcNAc is added to the mannose, followed by a Gal with an attached PEG moiety. In yet another embodiment, unmodified GlcNAc and Gal residues are sequentially added to the mannose, followed by a sialic acid moiety modified with a PEG moiety.

In a further exemplary embodiment, high mannose is "trimmed back" to the GlcNAc to which the first mannose is attached. The GlcNAc is conjugated to a Gal residue bearing a PEG moiety. Alternatively, an unmodified Gal is added to the GlcNAc, followed by the addition of a sialic acid modified with a water-soluble sugar. In yet a further example, the terminal GlcNAc is conjugated with Gal and the GlcNAc is subsequently fucosylated with a modified fucose bearing a PEG moiety.

Other exemplary embodiments are set forth in commonly owned U.S. Patent application Publications: 20040132640; 20040063911; 20040137557; U.S. patent application Ser. Nos. 10/369,979; 10/410,913; 10/360,770; 10/410,945 and PCT/US02/32263 each of which is incorporated herein by reference.

The examples set forth above provide an illustration of the power of the methods set forth herein. Using the methods described herein, it is possible to "trim back" and build up a carbohydrate residue of substantially any desired structure. The modified sugar can be added to the termini of the carbohydrate moiety as set forth above, or it can be intermediate between the peptide core and the terminus of the carbohydrate.

In an exemplary embodiment, an existing sialic acid is removed from a G-CSF glycopeptide using a sialidase, thereby unmasking all or most of the underlying galactosyl residues. Alternatively, a peptide or glycopeptide is labeled with galactose residues, or an oligosaccharide residue that terminates in a galactose unit. Following the exposure of or addition of the galactose residues, an appropriate sialyltransferase is used to add a modified sialic acid. The approach is summarized in Scheme 1.

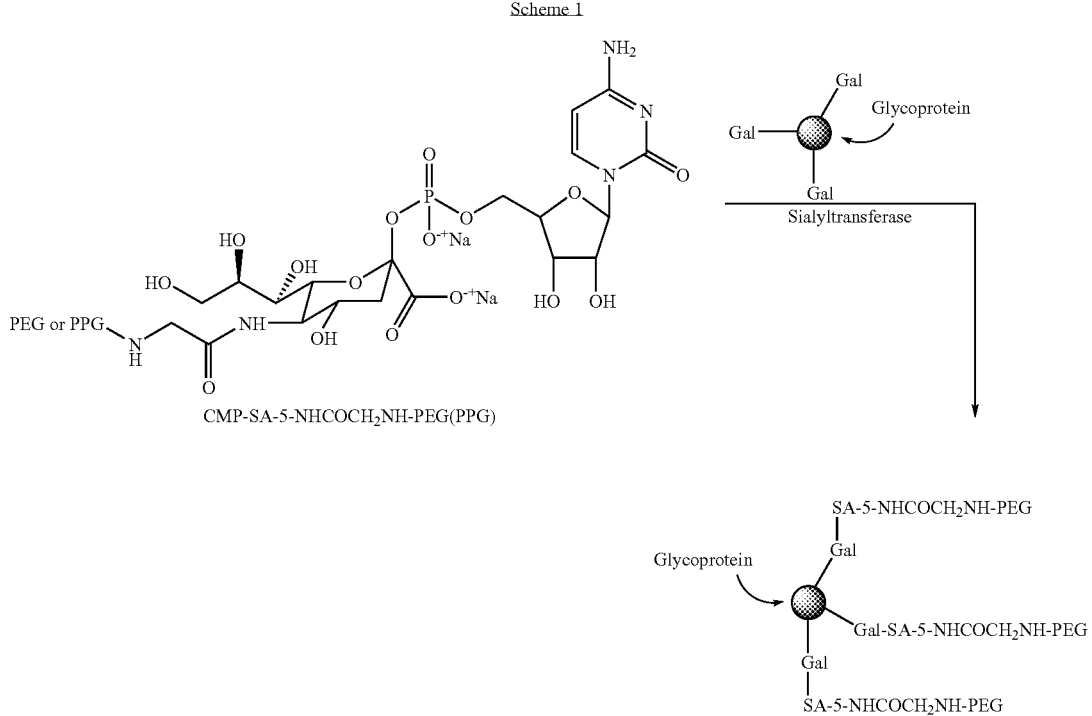

High mannose may also be trimmed back to the first GlcNAc attached to the Asn of the peptide. In one example, the GlcNAc of the GlcNAc-(Fuc)$_a$ residue is conjugated with ha GlcNAc bearing a water soluble polymer. In another example, the GlcNAc of the GlcNAc-(Fuc)$_a$ residue is modified with Gal, which bears a water soluble polymer. In a still further embodiment, the GlcNAc is modified with Gal, followed by conjugation to the Gal of a sialic acid modified with a PEG moiety.

In yet a further approach, summarized in Scheme 2, a masked reactive functionality is present on the sialic acid. The masked reactive group is preferably unaffected by the conditions used to attach the modified sialic acid to the G-CSF. After the covalent attachment of the modified sialic acid to the G-CSF peptide, the mask is removed and the G-CSF peptide is conjugated with an agent such as PEG. The agent is conjugated to the peptide in a specific manner by its reaction with the unmasked reactive group on the modified sugar residue.

Scheme 2

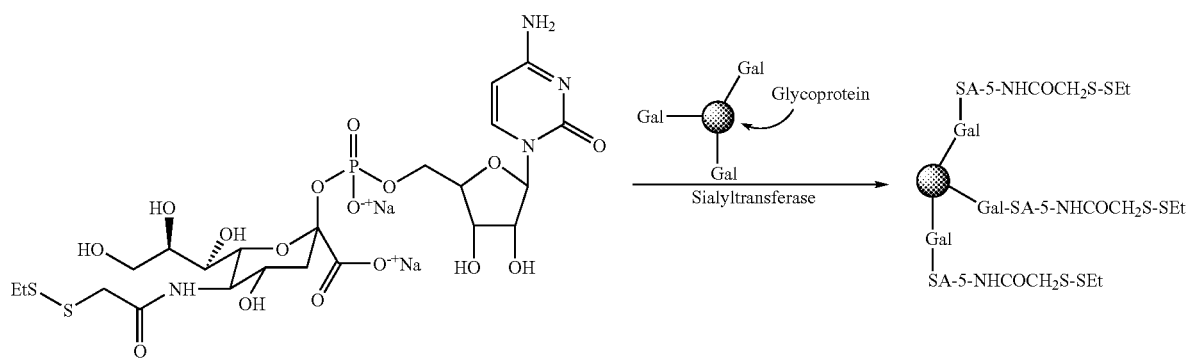

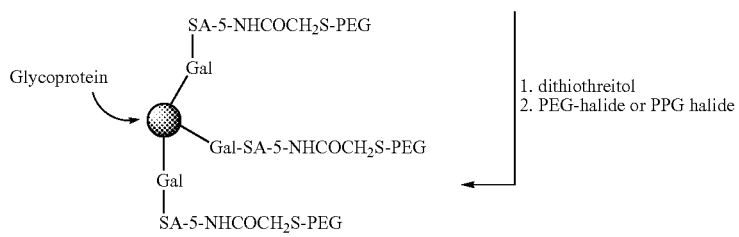

Any modified sugar set forth herein can be used with its appropriate glycosyltransferase, depending on the terminal sugars of the oligosaccharide side chains of the glycopeptide (Table 1). As discussed above, the terminal sugar of the glycopeptide required for introduction of the PEGylated structure can be introduced naturally during expression or it can be produced post expression using the appropriate glycosidase(s), glycosyltransferase(s) or mix of glycosidase(s) and glycosyltransferase(s).

TABLE 1

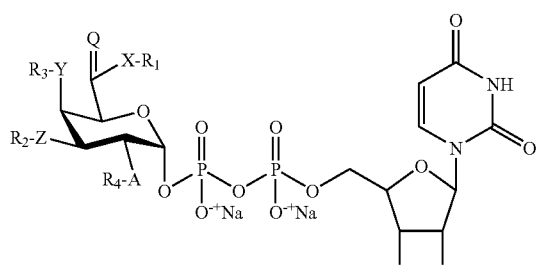

UDP-galactose-derivatives

TABLE 1-continued

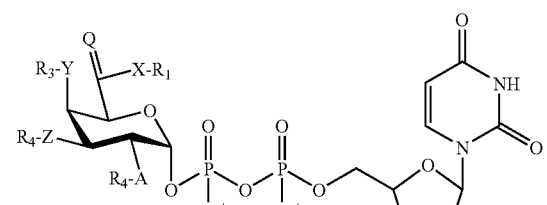

UDP-galactosamine-derivatives
(when A = NH, $R_4$ may be acetyl)

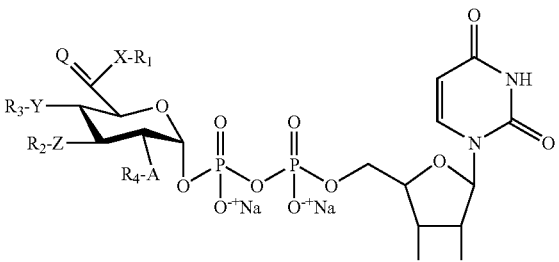

UDP-Glucose-derivatives

TABLE 1-continued

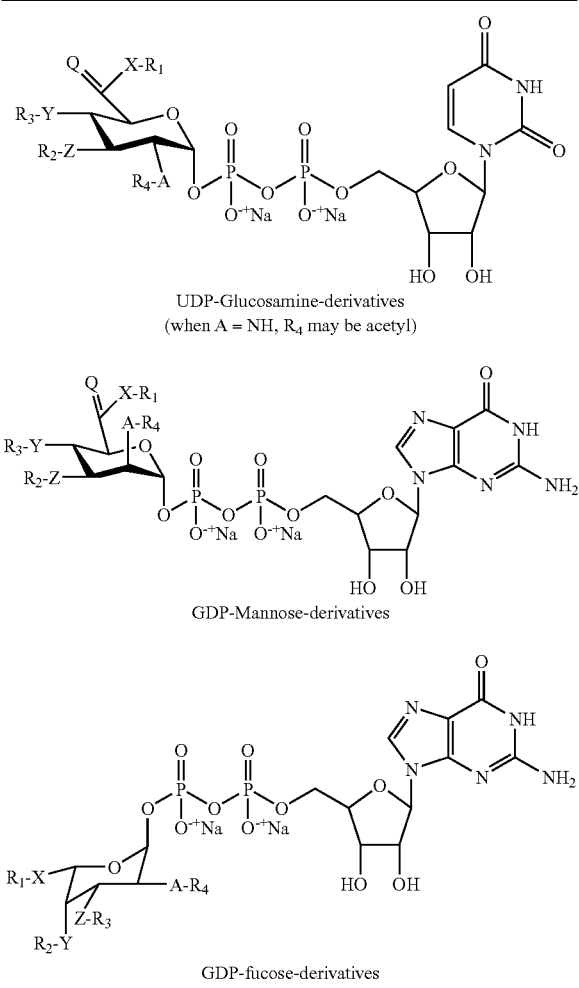

UDP-Glucosamine-derivatives
(when A = NH, R$_4$ may be acetyl)

GDP-Mannose-derivatives

GDP-fucose-derivatives

X = O, NH, S, CH$_2$, N—(R$_{1-5}$)$_2$.
Y = X; Z = X; A = X; B = X.
Q = H$_2$, O, S, NH, N—R.
R, R$_{1-4}$ = H, Linker-M, M.
M = PEG, e.g., m-PEG In a further exemplary embodiment, UDP-galactose-PEG is reacted with bovine milk β1,4-galactosyltransferase, thereby transferring the modified galactose to the appropriate terminal N-acetylglucosamine structure. The terminal GlcNAc residues on the glycopeptide may be produced during expression, as may occur in such expression systems as mammalian, insect, plant or fungus, but also can be produced by treating the glycopeptide with a sialidase and/or glycosidase and/or glycosyltransferase, as required.

In another exemplary embodiment, a GlcNAc transferase, such as GNT1-5, is utilized to transfer PEGylated-GlcN to a terminal mannose residue on a glycopeptide. In a still further exemplary embodiment, an the N- and/or O-linked glycan structures are enzymatically removed from a glycopeptide to expose an amino acid or a terminal glycosyl residue that is subsequently conjugated with the modified sugar. For example, an endoglycanase is used to remove the N-linked structures of a glycopeptide to expose a terminal GlcNAc as a GlcNAc-linked-Asn on the glycopeptide. UDP-Gal-PEG and the appropriate galactosyltransferase is used to introduce the PEG-galactose functionality onto the exposed GlcNAc.

In an alternative embodiment, the modified sugar is added directly to the G-CSF peptide backbone using a glycosyltransferase known to transfer sugar residues to the peptide backbone. This exemplary embodiment is set forth in Scheme 3. Exemplary glycosyltransferases useful in practicing the present invention include, but are not limited to, GalNAc transferases (GalNAc T1-14), GlcNAc transferases, fucosyltransferases, glucosyltransferases, xylosyltransferases, mannosyltransferases and the like. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of agents can be introduced into proteins or glycopeptides that lack the glycosyltransferase substrate peptide sequence by engineering the appropriate amino acid sequence into the polypeptide chain.

Scheme 3

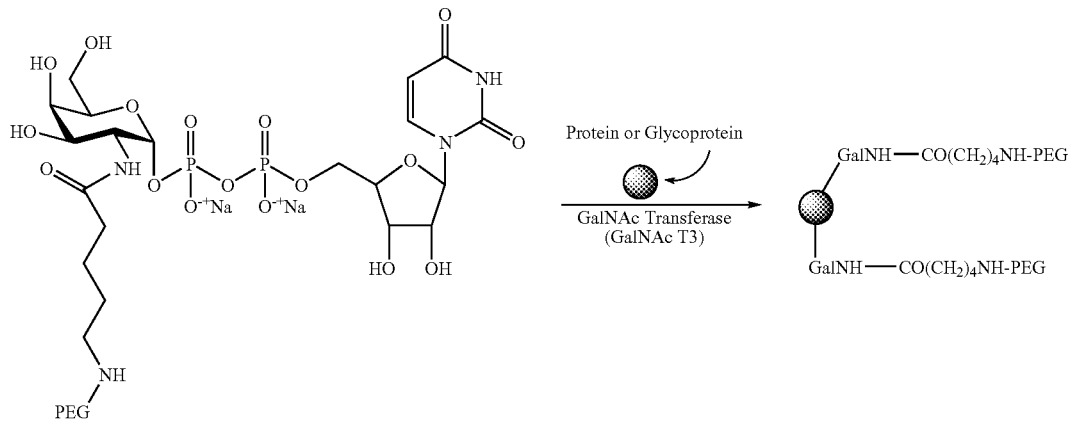

In each of the exemplary embodiments set forth above, one or more additional chemical or enzymatic modification steps can be utilized following the conjugation of the modified sugar to the peptide. In an exemplary embodiment, an enzyme (e.g., fucosyltransferase) is used to append a glycosyl unit (e.g., fucose) onto the terminal modified sugar attached to the G-CSF peptide. In another example, an enzymatic reaction is utilized to "cap" sites to which the modified sugar failed to conjugate. Alternatively, a chemical reaction is utilized to alter the structure of the conjugated modified sugar. For example, the conjugated modified sugar is reacted with agents that stabilize or destabilize its linkage with the peptide component to which the modified sugar is attached. In another example, a component of the modified sugar is deprotected following its conjugation to the peptide. One of skill will appreciate that there is an array of enzymatic and chemical procedures that are useful in the methods of the invention at a stage after the modified sugar is conjugated to the G-CSF peptide. Further elaboration of the modified sugar-peptide conjugate is within the scope of the invention.

Enzymes

In addition to the enzymes discussed above in the context of forming the acyl-linked conjugate, the glycosylation pattern of the conjugate and the starting substrates (e.g., peptides, lipids) can be elaborated, trimmed back or otherwise modified by methods utilizing other enzymes. The methods of remodeling peptides and lipids using enzymes that transfer a sugar donor to an acceptor are discussed in great detail in DeFrees, WO 03/031464 A2, published Apr. 17, 2003. A brief summary of selected enzymes of use in the present method is set forth below.

Glycosyltransferases

Glycosyltransferases catalyze the addition of activated sugars (donor NDP- or NMP-sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-NAG$_2$Glc$_3$Man$_9$ in an en block transfer followed by trimming of the core. In this case the nature of the "core" saccharide is somewhat different from subsequent attachments. A very large number of glycosyltransferases are known in the art.

The glycosyltransferase to be used in the present invention may be any as long as it can utilize the modified sugar as a sugar donor. Examples of such enzymes include Leloir pathway glycosyltransferase, such as galactosyltransferase, N-acetylglucosaminyltransferase, N-acetylgalactosaminyltransferase, fucosyltransferase, sialyltransferase, mannosyltransferase, xylosyltransferase, glucurononyltransferase and the like.

For enzymatic saccharide syntheses that involve glycosyltransferase reactions, glycosyltransferase can be cloned, or isolated from any source. Many cloned glycosyltransferases are known, as are their polynucleotide sequences. See, e.g., "The WWW Guide To Cloned Glycosyltransferases," (http://www.vei.co.uk/TGN/gt_guide.htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, and oligosaccharyltransferases. Suitable glycosyltransferases include those obtained from eukaryotes, as well as from prokaryotes.

DNA encoding glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out with oligonucleotide probes generated from the glycosyltransferases gene sequence. Probes may be labeled with a detectable group such as a fluorescent group, a radioactive atom or a chemiluminescent group in accordance with known procedures and used in conventional hybridization assays. In the alternative, glycosyltransferases gene sequences may be obtained by use of the polymerase chain reaction (PCR) procedure, with the PCR oligonucleotide primers being produced from the glycosyltransferases gene sequence. See, U.S. Pat. No. 4,683,195 to Mullis et al. and U.S. Pat. No. 4,683,202 to Mullis.

The glycosyltransferase may be synthesized in host cells transformed with vectors containing DNA encoding the glycosyltransferases enzyme. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

In an exemplary embodiment, the invention utilizes a prokaryotic enzyme. Such glycosyltransferases include enzymes involved in synthesis of lipooligosaccharides (LOS), which are produced by many gram negative bacteria (Preston et al., *Critical Reviews in Microbiology* 23(3): 139-180 (1996)). Such enzymes include, but are not limited to, the proteins of the rfa operons of species such as *E. coli* and *Salmonella typhimurium*, which include a β1,6 galactosyltransferase and a β1,3 galactosyltransferase (see, e.g., EMBL Accession Nos. M80599 and M86935 (*E. coli*); EMBL Accession No. S56361 (*S. typhimurium*)), a glucosyltransferase (Swiss-Prot Accession No. P25740 (*E. coli*), an β1,2-glucosyltransferase (rfaJ)(Swiss-Prot Accession No. P27129 (*E. coli*) and Swiss-Prot Accession No. P19817 (*S. typhimurium*)), and an β1,2-N-acetylglucosaminyltransferase (rfaK) (EMBL Accession No. U00039 (*E. coli*). Other glycosyltransferases for which amino acid sequences are known include those that are encoded by operons such as rfaB, which have been characterized in organisms such as *Klebsiella pneumoniae, E. coli, Salmonella typhimurium, Salmonella enterica, Yersinia enterocolitica, Mycobacterium leprosum*, and the rh1 operon of *Pseudomonas aeruginosa*.

Also suitable for use in the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the P$^k$ blood group trisaccharide sequence, D-galactosyl-α-1,4-D-galactosyl-β-1,4-D-glucose, which have been identified in the LOS of the mucosal pathogens *Neisseria gonnorhoeae* and *N. meningitidis* (Scholten et al., *J. Med. Microbiol.* 41: 236-243 (1994)). The genes from *N. meningitidis* and *N. gonorrhoeae* that encode the glycosyltransferases involved in the biosynthesis of these structures have been identified from *N. meningitidis* immunotypes L3 and L1 (Jennings et al., *Mol. Microbiol.* 18: 729-740 (1995)) and the *N. gonorrhoeae* mutant F62 (Gotshlich, *J. Exp. Med.* 180: 2181-2190 (1994)). In *N. meningitidis*, a locus consisting of three genes, lgtA, lgtB and 1 g E, encodes the glycosyltransferase enzymes required for addition of the last three of the sugars in the lacto-N-neotetraose chain (Wakarchuk et al., *J. Biol. Chem.* 271: 19166-73 (1996)). Recently the enzymatic activity of the lgtB and lgtA gene product was demonstrated, providing the first direct evidence for their proposed glycosyltransferase function (Wakarchuk et al., *J. Biol. Chem.* 271(45): 28271-276 (1996)). In *N. gonorrhoeae*, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the $P^k$ blood group antigen structure (Gotshlich (1994), supra.). In *N. meningitidis*, a separate immunotype L1 also expresses the $P^k$ blood group antigen and has been shown to carry an lgtC gene (Jennings et al., (1995), supra.). *Neisseria* glycosyltransferases and associated genes are also described in U.S. Pat. No. 5,545,553 (Gotshlich). Genes for α1,2-fucosyltransferase and α1,3-fucosyltransferase from *Helicobacter pylori* has also been characterized (Martin et al., *J. Biol. Chem.* 272: 21349-21356 (1997)). Also of use in the present invention are the glycosyltransferases of *Campylobacter jejuni* (see, for example, http://afmb.cnrs-mrs.fr/~pedro/CAZY/gtf_42.html).

Fucosyltransferases

In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer non-nucleotide sugars to an acceptor are also of use in the present invention.

In some embodiments, the acceptor sugar is, for example, the GlcNAc in a Galβ(1→3,4)GlcNAcβ-group in an oligosaccharide glycoside. Suitable fucosyltransferases for this reaction include the Galβ(1→3,4)GlcNAcβ1-α(1→3,4)fucosyltransferase (FTIII E.C. No. 2.4.1.65), which was first characterized from human milk (see, Palcic, et al., *Carbohydrate Res.* 190:1-11 (1989); Prieels, et al., *J. Biol. Chem.* 256: 10456-10463 (1981); and Nunez, et al., *Can. J. Chem.* 59: 2086-2095 (1981)) and the Galβ(1→4)GlcNAcβ-αfucosyltransferases (FTIV, FTV, FTVI) which are found in human serum. FTVII (E.C. No. 2.4.1.65), a sialyl α(2→3)Galβ ((1→3)GlcNAcβ fucosyltransferase, has also been characterized. A recombinant form of the Galβ(1→3,4) GlcNAcβ-α (1→3,4)fucosyltransferase has also been characterized (see, Dumas, et al., *Bioorg. Med. Letters* 1: 425-428 (1991) and Kukowska-Latallo, et al., *Genes and Development* 4: 1288-1303 (1990)). Other exemplary fucosyltransferases include, for example, α1,2 fucosyltransferase (E.C. No. 2.4.1.69). Enzymatic fucosylation can be carried out by the methods described in Mollicone, et al., *Eur. J. Biochem.* 191: 169-176 (1990) or U.S. Pat. No. 5,374,655. Cells that are used to produce a fucosyltransferase will also include an enzymatic system for synthesizing GDP-fucose.

Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345: 229-233 (1990), bovine (GenBank j04989, Joziasse et al., *J. Biol. Chem.* 264: 14290-14297 (1989)), murine (GenBank m26925; Larsen et al., *Proc. Nat'l. Acad. Sci. USA* 86: 8227-8231 (1989)), porcine (GenBank L36152; Strahan et al., *Immunogenetics* 41: 101-105 (1995)). Another suitable α1,3 galactosyltransferase is that which is involved in synthesis of the blood group B antigen (EC 2.4.1.37, Yamamoto et al., *J. Biol. Chem.* 265: 1146-1151 (1990) (human)). Yet a further exemplary galactosyltransferase is core Gal-T1.

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., *Eur. J. Biochem.* 183: 211-217 (1989)), human (Masri et al., *Biochem. Biophys. Res. Commun.* 157: 657-663 (1988)), murine (Nakazawa et al., *J. Biochem.* 104: 165-168 (1988)), as well as E.C. 2.4.1.38 and the ceramide galactosyltransferase (EC 2.4.1.45, Stahl et al., *J. Neurosci. Res.* 38: 234-242 (1994)). Other suitable galactosyltransferases include, for example, α1,2 galactosyltransferases (from e.g., *Schizosaccharomyces pombe*, Chapell et al., *Mol. Biol. Cell* 5: 519-528 (1994)).

Sialyltransferases

Sialyltransferases are another type of glycosyltransferase that is useful in the recombinant cells and reaction mixtures of the invention. Cells that produce recombinant sialyltransferases will also produce CMP-sialic acid, which is a sialic acid donor for sialyltransferases. Examples of sialyltransferases that are suitable for use in the present invention include ST3Gal III (e.g., a rat or human ST3Gal III), ST3Gal IV, ST3Gal I, ST3GalII, ST6Gal I, ST3Gal V, ST6Gal II, ST6GalNAc I, ST6GalNAc II, and ST6GalNAc III (the sialyltransferase nomenclature used herein is as described in Tsuji et al., *Glycobiology* 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., *J. Biol. Chem.* 256: 3159 (1981), Weinstein et al., *J. Biol. Chem.* 257: 13845 (1982) and Wen et al., *J. Biol. Chem.* 267: 21011 (1992). Another exemplary α2,3-sialyltransferase (EC 2.4.99.4) transfers sialic acid to the non-reducing terminal Gal of the disaccharide or glycoside. see, Rearick et al., *J. Biol. Chem.* 254: 4444 (1979) and Gillespie et al., *J. Biol. Chem.* 267: 21004 (1992). Further exemplary enzymes include Gal-(β-1,4-GlcNAc α-2,6 sialyltransferase (See, Kurosawa et al. *Eur. J. Biochem.* 219: 375-381 (1994)).

Preferably, for glycosylation of carbohydrates of glycopeptides the sialyltransferase will be able to transfer sialic acid to the sequence Galβ1,4GlcNAc-, the most common penultimate sequence underlying the terminal sialic acid on fully sialylated carbohydrate structures (see, Table 2).

TABLE 2

Sialyltransferases which use the Galβ1,4GlcNAc sequence as an acceptor substrate

| Sialyltransferase | Source | Sequence(s) formed | Ref. |
| --- | --- | --- | --- |
| ST6Gal I | Mammalian | NeuAcα2,6Galβ1,4GlcNAc- | 1 |
| ST3Gal III | Mammalian | NeuAcα2,3Galβ1,4GlcNAc- NeuAcα2,3Galβ1,3GlcNAc- | 1 |
| ST3Gal IV | Mammalian | NeuAcα2,3Galβ1,4GlcNAc- NeuAcα2,3Galβ1,3GlcNAc- | 1 |
| ST6Gal II | Mammalian | NeuAcα2,6Galβ1,4GlcNA | |
| ST6Gal II | photobacterium | NeuAcα2,6Galβ1,4GlcNAc- | 2 |

TABLE 2-continued

Sialyltransferases which use the Galβ1,4GlcNAc
sequence as an acceptor substrate

| Sialyltransferase | Source | Sequence(s) formed | Ref. |
|---|---|---|---|
| ST3Gal V | N. meningitides N. gonorrhoeae | NeuAcα2,3Galβ1,4GlCNAc- | 3 |

1) Goochee et al., Bio/Technology 9: 1347-1355 (1991)
2) Yamamoto et al., J. Biochem. 120: 104-110 (1996)
3) Gilbert et al., J. Biol. Chem. 271: 28271-28276 (1996)

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1,3GlcNAc or Galβ1,4GlcNAc glycoside (see, e.g., Wen et al., *J. Biol. Chem.* 267: 21011 (1992); Van den Eijnden et al., *J. Biol. Chem.* 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., *J. Biol. Chem.* 257: 13845 (1982)); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In one embodiment, the claimed sialylation methods use a rat ST3Gal III.

Other exemplary sialyltransferases of use in the present invention include those isolated from *Campylobacter jejuni*, including CST-I and CST-II and those forming α (2,3) linkages. See, e.g., WO99/49051.

Sialyltransferases other those listed in Table 2, are also useful in an economic and efficient large-scale process for sialylation of commercially important glycopeptides. As a simple test to find out the utility of these other enzymes, various amounts of each enzyme (1-100 mU/mg protein) are reacted with asialo-$\alpha_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides or glycopeptides, or N-linked oligosaccharides enzymatically released from the peptide backbone can be used in place of asialo-$\alpha_1$ AGP for this evaluation. Sialyltransferases with the ability to sialylate N-linked oligosaccharides of glycopeptides more efficiently than ST6Gal I are useful in a practical large-scale process for peptide sialylation.

GalNAc Transferases

N-acetylgalactosaminyltransferases are of use in practicing the present invention, particularly for binding a GalNAc moiety to an amino acid of the O-linked glycosylation site of the peptide. Suitable N-acetylgalactosaminyltransferases include, but are not limited to, α(1,3) N-acetylgalactosaminyltransferase, β(1,4) N-acetylgalactosaminyltransferases (Nagata et al., *J. Biol. Chem.* 267: 12082-12089 (1992) and Smith et al., *J. Biol. Chem.* 269: 15162 (1994)) and polypeptide N-acetylgalactosaminyltransferase (Homa et al., *J. Biol. Chem.* 268: 12609 (1993)).

Production of proteins such as the enzyme GalNAc $T_{I-XX}$ from cloned genes by genetic engineering is well known. See, e.g., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

Cell-Bound Glycosyltransferases

In another embodiment, the enzymes utilized in the method of the invention are cell-bound glycosyltransferases. Although many soluble glycosyltransferases are known (see, for example, U.S. Pat. No. 5,032,519), glycosyltransferases are generally in membrane-bound form when associated with cells. Many of the membrane-bound enzymes studied thus far are considered to be intrinsic proteins; that is, they are not released from the membranes by sonication and require detergents for solubilization. Surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition (Roth, MOLECULAR APPROACHES to SUPRACELLULAR PHENOMENA, 1990).

Methods have been developed to alter the glycosyltransferases expressed by cells. For example, Larsen et al., *Proc. Natl. Acad. Sci. USA* 86: 8227-8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose:β.-D-galactosyl-1,4-N-acetyl-D-glucosaminide α-1,3-galactosyltransferase was transfected into COS-1 cells. The transfected cells were then cultured and assayed for α 1-3 galactosyltransferase activity.

Francisco et al., *Proc. Natl. Acad. Sci. USA* 89: 2713-2717 (1992), disclose a method of anchoring β-lactamase to the external surface of *Escherichia coli*. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to procaryotic cell systems and as recognized by the authors, requires the complete tripartite fusion for proper functioning.

Sulfotransferases

The invention also provides methods for producing peptides that include sulfated molecules, including, for example sulfated polysaccharides such as heparin, heparan sulfate, carragenen, and related compounds. Suitable sulfotransferases include, for example, chondroitin-6-sulphotransferase (chicken cDNA described by Fukuta et al., *J. Biol. Chem.* 270: 18575-18580 (1995); GenBank Accession No. D49915), glycosaminoglycan N-acetylglucosamine N-deacetylase/N-sulphotransferase 1 (Dixon et al., *Genomics* 26: 239-241 (1995); UL18918), and glycosaminoglycan N-acetylglucosamine N-deacetylase/N-sulphotransferase 2 (murine cDNA described in Orellana et al., *J. Biol. Chem.* 269: 2270-2276 (1994) and Eriksson et al., *J. Biol. Chem.* 269: 10438-10443 (1994); human cDNA described in GenBank Accession No. U2304).

Glycosidases

This invention also encompasses the use of wild-type and mutant glycosidases. Mutant β-galactosidase enzymes have been demonstrated to catalyze the formation of disaccharides through the coupling of an α-glycosyl fluoride to a galactosyl acceptor molecule. (Withers, U.S. Pat. No. 6,284,494; issued Sep. 4, 2001). Other glycosidases of use in this invention include, for example, β-glucosidases, β-galactosidases, β-mannosidases, β-acetyl glucosaminidases, β-N-acetyl galactosaminidases, β-xylosidases, β-fucosidases, cellulases, xylanases, galactanases, mannanases, hemicellulases, amylases, glucoamylases, α-glucosidases, α-galactosidases, α-mannosidases, α-N-acetyl glucosaminidases, α-N-acetyl galactose-aminidases, α-xylosidases, α-fucosidases, and neuraminidases/sialidases.

Immobilized Enzymes

The present invention also provides for the use of enzymes that are immobilized on a solid and/or soluble support. In an exemplary embodiment, there is provided a glycosyltransferase that is conjugated to a PEG via an intact glycosyl linker according to the methods of the invention. The PEG-linker-enzyme conjugate is optionally attached to solid support. The use of solid supported enzymes in the methods of the invention simplifies the work up of the reaction mixture and purification of the reaction product, and also enables the facile recovery of the enzyme. The glycosyltransferase conjugate is utilized in the methods of the invention. Other combinations of enzymes and supports will be apparent to those of skill in the art.

Fusion Proteins

In other exemplary embodiments, the methods of the invention utilize fusion proteins that have more than one enzymatic activity that is involved in synthesis of a desired glycopeptide conjugate. The fusion polypeptides can be composed of, for example, a catalytically active domain of a glycosyltransferase that is joined to a catalytically active domain of an accessory enzyme. The accessory enzyme catalytic domain can, for example, catalyze a step in the formation of a nucleotide sugar that is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion protein can then catalyze not only the synthesis of the nucleotide sugar, but also the transfer of the sugar moiety to the acceptor molecule. The fusion protein can be two or more cycle enzymes linked into one expressible nucleotide sequence. In other embodiments the fusion protein includes the catalytically active domains of two or more glycosyltransferases. See, for example, U.S. Pat. No. 5,641,668. The modified glycopeptides of the present invention can be readily designed and manufactured utilizing various suitable fusion proteins (see, for example, PCT Patent Application PCT/CA98/01180, which was published as WO 99/31224 on Jun. 24, 1999.)

Preparation of Modified Sugars

Methods of the invention generally utilize modified sugars. In one aspect, the sugar moiety or sugar moiety-linker cassette and the PEG or PEG-linker cassette groups are linked together through the use of reactive groups, which are typically transformed by the linking process into a new organic functional group or unreactive species. The sugar reactive functional group(s), is located at any position on the sugar moiety. Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from a sugar nucleus or modifying group include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In the discussion that follows, a number of specific examples of modified sugars that are useful in practicing the present invention are set forth. In the exemplary embodiments, a sialic acid derivative is utilized as the sugar nucleus to which the modifying group is attached. The focus of the discussion on sialic acid derivatives is for clarity of illustration only and should not be construed to limit the scope of the invention. Those of skill in the art will appreciate that a variety of other sugar moieties can be activated and derivatized in a manner analogous to that set forth using sialic acid as an example. For example, numerous methods are available for modifying galactose, glucose, N-acetylgalactosamine and fucose to name a few sugar substrates, which are readily modified by art recognized methods. See, for example, Elhalabi et al., *Curr. Med. Chem.* 6: 93 (1999); and Schafer et al., *J. Org. Chem.* 65: 24 (2000)).

In an exemplary embodiment, the G-CSF peptide that is modified by a method of the invention is a glycopeptide that is produced in mammalian cells (e.g., CHO cells) or in a transgenic animal and thus, contains N- and/or O-linked oligosaccharide chains, which are incompletely sialylated. The oligosaccharide chains of the glycopeptide lacking a sialic acid and containing a terminal galactose residue can be PEGylated, PPGylated or otherwise modified with a modified sialic acid.

In Scheme 4, the amino glycoside 1, is treated with the active ester of a protected amino acid (e.g., glycine) derivative, converting the sugar amine residue into the corresponding protected amino acid amide adduct. The adduct is treated with an aldolase to form α-hydroxy carboxylate 2. Compound 2 is converted to the corresponding CMP derivative by the action of CMP-SA synthetase, followed by catalytic hydrogenation of the CMP derivative to produce compound 3. The amine introduced via formation of the glycine adduct is utilized as a locus of PEG attachment by reacting compound 3 with an activated PEG or PPG derivative (e.g., PEG-C(O)NHS, PEG-OC(O)O-p-nitrophenyl), producing species such as 4 or 5, respectively.

Table 3 sets forth representative examples of sugar monophosphates that are derivatized with a PEG moiety. Certain of the compounds of Table 3 are prepared by the method of Scheme 4. Other derivatives are prepared by art-recognized methods. See, for example, Keppler et al., *Glycobiology* 11: 11R (2001); and Charter et al., *Glycobiology* 10: 1049 (2000)). Other amine reactive PEG and PPG analogues are commercially available, or they can be prepared by methods readily accessible to those of skill in the art.

TABLE 3

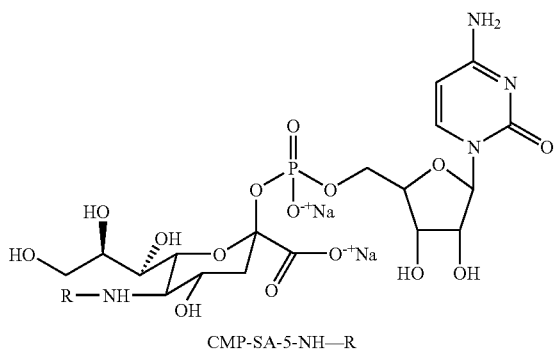

CMP-SA-5-NH—R

Scheme 4

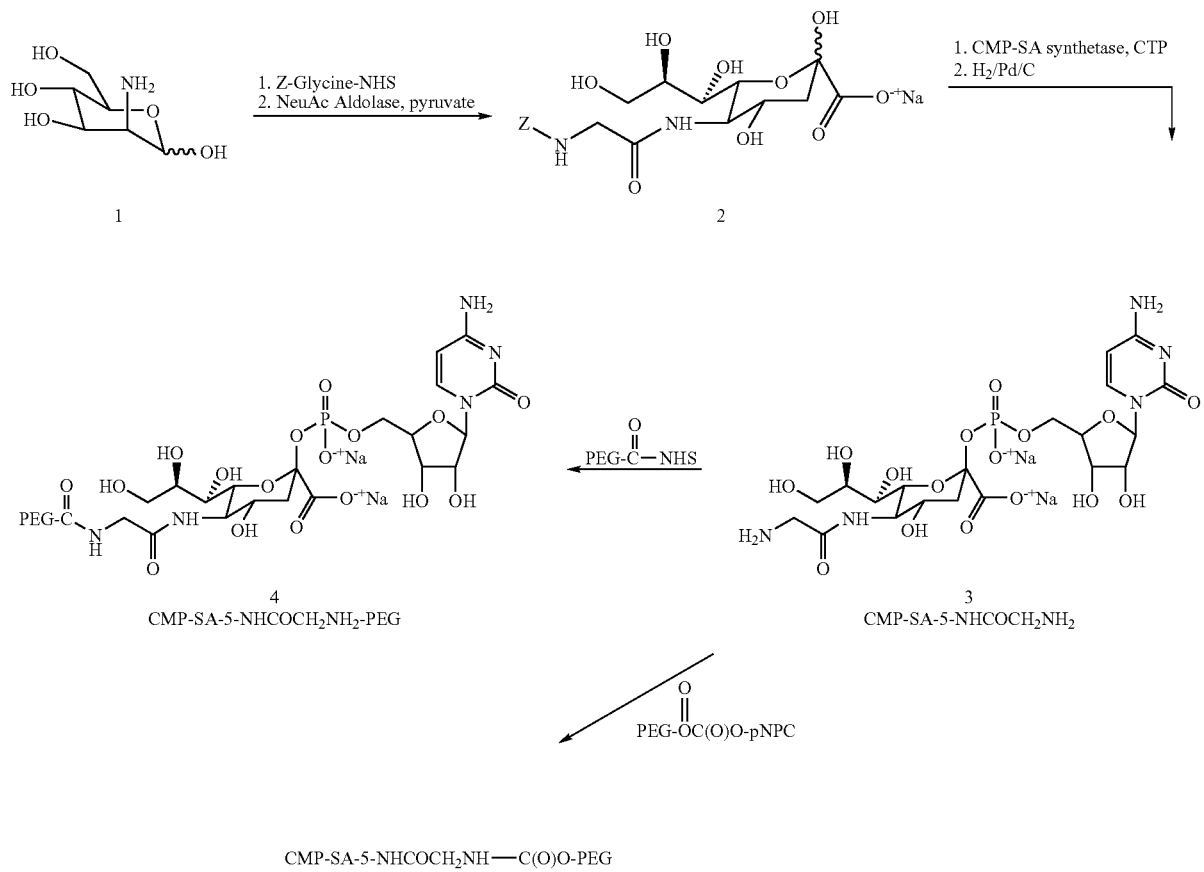

TABLE 3-continued
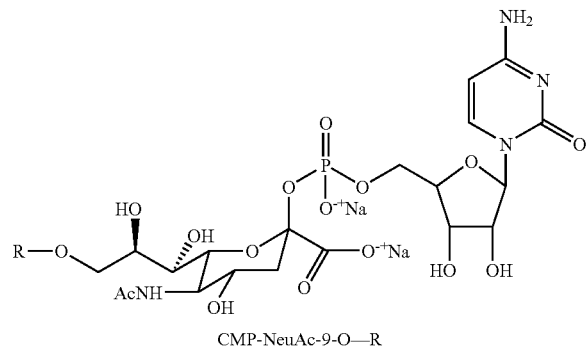
CMP-NeuAc-9-O—R
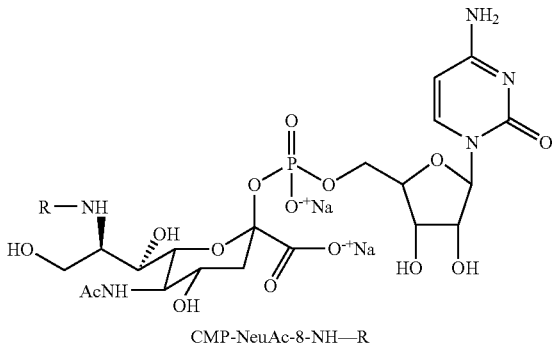
CMP-NeuAc-8-NH—R
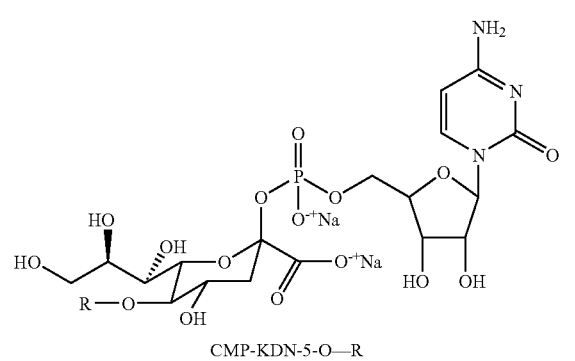
CMP-KDN-5-O—R
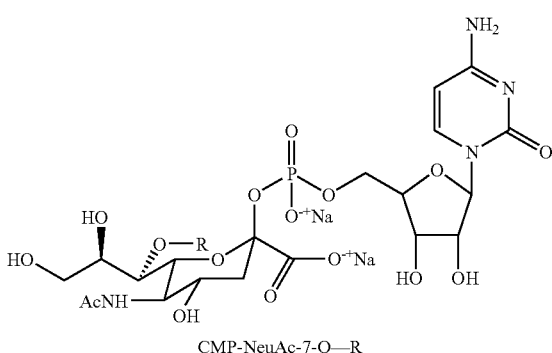
CMP-NeuAc-7-O—R
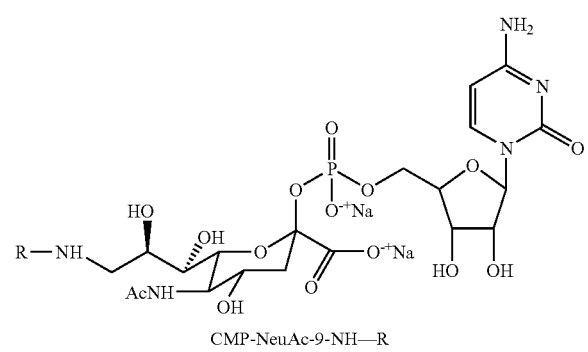
CMP-NeuAc-9-NH—R
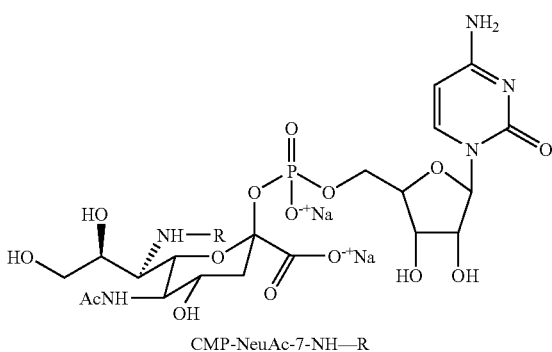
CMP-NeuAc-7-NH—R
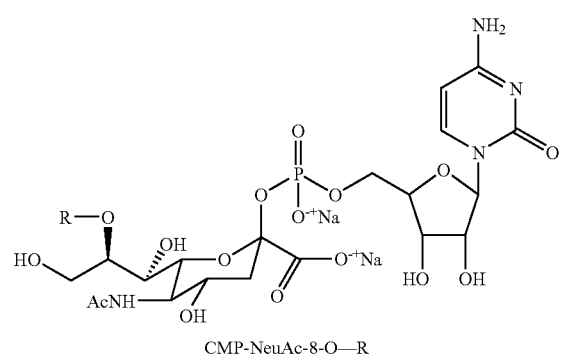
CMP-NeuAc-8-O—R
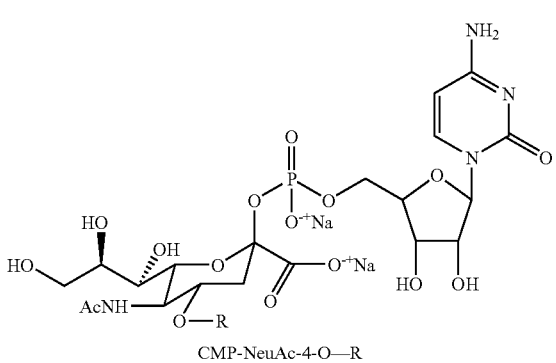
CMP-NeuAc-4-O—R TABLE 3-continued

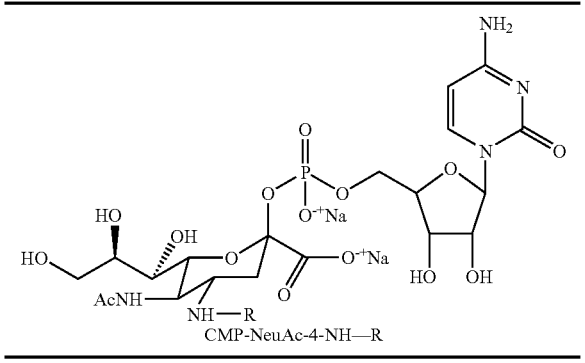

CMP-NeuAc-4-NH—R

The modified sugar phosphates of use in practicing the present invention can be substituted in other positions as well as those set forth above. Presently preferred substitutions of sialic acid are set forth in the formula below:

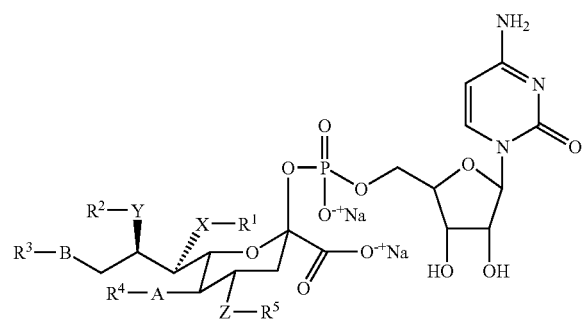

in which X is a linking group, which is preferably selected from —O—, —N(H)—, —S, $CH_2$—, and —$N(R)_2$, in which each R is a member independently selected from $R^1$-$R^5$. The symbols Y, Z, A and B each represent a group that is selected from the group set forth above for the identity of X, X, Y, Z, A and B are each independently selected and, therefore, they can be the same or different. The symbols $R^1$, $R^2$, $R^3$, $R^4$ and $R^5$ represent H, a PEG moiety, therapeutic moiety, biomolecule or other moiety. Alternatively, these symbols represent a linker that is bound to a PEG moiety, therapeutic moiety, biomolecule or other moiety.

Exemplary moieties attached to the conjugates disclosed herein include, but are not limited to, PEG derivatives (e.g., acyl-PEG, acyl-alkyl-PEG, alkyl-acyl-PEG carbamoyl-PEG, aryl-PEG), PPG derivatives (e.g., acyl-PPG, acyl-alkyl-PPG, alkyl-acyl-PPG carbamoyl-PPG, aryl-PPG), therapeutic moieties, diagnostic moieties, mannose-6-phosphate, heparin, heparan, $SLe_x$, mannose, mannose-6-phosphate, Sialyl Lewis X, FGF, VFGF, proteins, chondroitin, keratan, dermatan, albumin, integrins, antennary oligosaccharides, peptides and the like. Methods of conjugating the various modifying groups to a saccharide moiety are readily accessible to those of skill in the art (POLY (ETHYLENE GLYCOL CHEMISTRY: BIOTECHNICAL AND BIOMEDICAL APPLICATIONS, J. Milton Harris, Ed., Plenum Pub. Corp., 1992; POLY (ETHYLENE GLYCOL) CHEMICAL AND BIOLOGICAL APPLICATIONS, J. Milton Harris, Ed., ACS Symposium Series No. 680, American Chemical Society, 1997; Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991).

Linker Groups (Cross-Linking Groups)

Preparation of the Modified Sugar for Use in the Methods of the Present Invention includes attachment of a PEG moiety to a sugar residue and preferably, forming a stable adduct, which is a substrate for a glycosyltransferase. Thus, it is often preferred to use a linker, e.g., one formed by reaction of the PEG and sugar moiety with a cross-linking agent to conjugate the PEG and the sugar. Exemplary bifunctional compounds which can be used for attaching modifying groups to carbohydrate moieties include, but are not limited to, bifunctional poly(ethyleneglycols), polyamides, polyethers, polyesters and the like. General approaches for linking carbohydrates to other molecules are known in the literature. See, for example, Lee et al., *Biochemistry* 28: 1856 (1989); Bhatia et al., *Anal. Biochem.* 178: 408 (1989); Janda et al., *J. Am. Chem. Soc.* 112: 8886 (1990) and Bednarski et al., WO 92/18135. In the discussion that follows, the reactive groups are treated as benign on the sugar moiety of the nascent modified sugar. The focus of the discussion is for clarity of illustration. Those of skill in the art will appreciate that the discussion is relevant to reactive groups on the modifying group as well.

A variety of reagents are used to modify the components of the modified sugar with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

Refolding Insoluble G-CSF

Many recombinant proteins expressed in bacteria are expressed as insoluble aggregates in bacterial inclusion bodies. Inclusion bodies are protein deposits found in both the cytoplasmic and periplasmic space of bacteria. (See, e.g., Clark, *Cur. Op. Biotech.* 12:202-207 (2001)). Recombinant G-CSF proteins are expressed in bacterial inclusion bodies, and methods for refolding these proteins to produce active G-CSF proteins are provided herein.

Conditions for Refolding Active G-CSF

To produce active G-CSF proteins from bacterial cells, G-CSF proteins are expressed in bacterial inclusion bodies, the bacteria are harvested, disrupted and the inclusion bodies are isolated and washed. In one embodiment, three washes are performed: a first wash in a buffer at a pH between 6.0 and 9.0; a monovalent salt, e.g., sodium chloride; a nonionic detergent, e.g., Triton X-100; an ionic detergent, e.g., sodium deoxycholate; and EDTA; a second wash in a detergent free buffer, and a third wash in H₂0. The proteins within the inclusion bodies are then solubilized. Solubilization can be performed using denaturants, guanidiniunl chloride or urea; extremes of pH; or detergents or any combination of these. In one embodiment of 5-6M guanidine HCl or urea are used to solubilize GCSF. In ..mother embodiment, DTT is added.

After solubilization, denaturants are removed from the GCSF protein mixture. Denaturant removal can be done by a variety of methods, including dilution into a refolding buffet- or buffer exchange methods. Buffer exchange methods include dialysis, diafiltration, g.el filtration, and immobilization of the protein onto a solid support. (See, e.g., Clark, *Cur. Op. Biotech.* 12:202-207 (2001)). Any of the above methods can be combined to remove denaturants.

Disulfide bond formation in the GCSF proteins is promoted by addition of a refolding buffer comprising a redox couple. Redox couples include reduced and oxidized glutathionc ((-JSF-I/GSSG), cysteine/cystine, cysteamine/cystamine, DTT/GSSG, and DTE/GSSG. (See, e.g., Clark, *Cur. Op. Biotech.* 12:202-207 (2001)). In one embodiment the redox couple is GSH/GSSG at a ratio of 10:1.

Refolding can be performed in buffers at pH's ranging from, for example, 6.0 to 10.0. Refolding buffers can include other additives to enhance refolding, e.g., L-arginine (0.4-1 M); PEG; low concentrations of denaturants, such as urea (1-2M) and guanidinium chloride (0.5-1.5 M); and detergents (e.g., Chaps, SDS, CTAB, lauryl maltoside, Tween 80, and Triton X-100).

Alter refolding, the GCSF protein can be dialyzed to remove the redox couple or other unwanted buffer components. In one embodiment, dialysis is performed using a buffer including sodium acetae, glycerol, and a non-ionic detergent, e.g., Tween-80. After dialysis the GCSF protein can be further purified, and/or concentrated by ion exchange chromatography. In one embodiment, an SP-sepharose cation exchange resin is used.

Those of skill will recognize that a protein has been refolded correctly when the refolded protein has detectable biological activity. For a GCSF protein, biological activity can be measured using a variety of methods. For example, biologically active GCSF proteins are substrates for the O-linked glycosylation described in U.S. Patent Applications 60/535,284, filed Jan. 8, 2004; 60/544,411, filed Feb. 12, 2004; and U.S. Provisional Application No. 60/546,631, filed Feb. 20, 2004; each of which is herein incorporated by reference for all purposes. GCSF protein activity can also be measured using cell proliferation assays or white blood cell (WBC) assays in rats. (Also described in U.S. Patent Applications 60/535,284, filed Jan. 8, 2004; 60/544,411, filed Feb. 12, 2004; and U.S. Provisional Application No. 60/546,631, filed Feb. 20, 2004; each of which is herein incorporated by reference for all purposes.) The proliferation assays and the WBC assays can be done before or after O-linked glycosylation of the refolded GCSF proteins.

Methods for Isolating Conjugates of the Invention

Alternatively, the products produced by the above processes can be used without purification. However, it is usually preferred to recover the product. Standard, well-known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins such as glycosyl transferases. Nanofiltration or reverse osmosis can then be used to remove salts and/or purify the product saccharides (see, e.g., WO 98/15581). Nanofilter membranes are a class of reverse osmosis membranes that pass monovalent salts but retain polyvalent salts and uncharged solutes larger than about 100 to about 2,000 Daltons, depending upon the membrane used. Thus, in a typical application, saccharides prepared by the methods of the present invention will be retained in the membrane and contaminating salts will pass through.

If the modified glycoprotein is produced intracellularly, as a first step, the particulate debris, either host cells or lysed fragments, is removed, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Modified glycopeptides produced in culture are usually isolated by initial extraction from cells, enzymes, etc., followed by one or more concentration, salting-out, aqueous ion-exchange, or size-exclusion chromatography steps. Additionally, the modified glycoprotein may be purified by affinity chromatography. Finally, HPLC may be employed for final purification steps.

A protease inhibitor, e.g., methylsulfonylfluoride (PMSF) may be included in any of the foregoing steps to inhibit proteolysis and antibiotics may be included to prevent the growth of adventitious contaminants.

Within another embodiment, supernatants from systems which produce the modified glycopeptide of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Finally, one or more RP-HPLC steps employing hydrophobic RP-HPLC media, e.g., silica gel having pendant methyl or other aliphatic groups, may be employed to further purify a polypeptide variant composition. Some or all of the foregoing purification steps, in various combinations, can also be employed to provide a homogeneous modified glycoprotein.

The modified glycopeptide of the invention resulting from a large-scale fermentation may be purified by methods analogous to those disclosed by Urdal et al., *J. Chromatog.* 296: 171 (1984). This reference describes two sequential, RP- HPLC steps for purification of recombinant human IL-2 on a preparative HPLC column. Alternatively, techniques such as affinity chromatography may be utilized to purify the modified glycoprotein.

Pharmaceutical Compositions

In another aspect, the invention provides a pharmaceutical composition. The pharmaceutical composition includes a pharmaceutically acceptable diluent and a covalent conjugate between a non-naturally-occurring, PEG moiety, therapeutic moiety or biomolecule and a glycosylated or non-glycosylated peptide. The polymer, therapeutic moiety or biomolecule is conjugated to the G-CSF peptide via an intact glycosyl linking group interposed between and covalently linked to both the G-CSF peptide and the polymer, therapeutic moiety or biomolecule.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered parenterally, e.g., intravenously. Thus, the invention provides compositions for parenteral administration which comprise the compound dissolved or suspended in an acceptable carrier, preferably an aqueous carrier, e.g., water, buffered water, saline, PBS and the like. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the glycopeptides of the invention can be incorporated into liposomes formed from standard vesicle-forming lipids. A variety of methods are available for preparing liposomes, as described in, e.g., Szoka et al., *Ann. Rev. Biophys. Bioeng.* 9: 467 (1980), U.S. Pat. Nos. 4,235,871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively). Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The compounds prepared by the methods of the invention may also find use as diagnostic reagents. For example, labeled compounds can be used to locate areas of inflammation or tumor metastasis in a patient suspected of having an inflammation. For this use, the compounds can be labeled with $^{125}$I, $^{14}$C, or tritium.

The active ingredient used in the pharmaceutical compositions of the present invention is glycopegylated G-CSF and its derivatives having the biological properties of Follicle Stimulating Hormone to increase e.g., ovulation. Preferably, the G-CSF composition of the present invention is administered parenterally (e.g. IV, IM, SC or IP). Effective dosages are expected to vary considerably depending on the condition being treated and the route of administration but are expected to be in the range of about 0.1 (~7 U) to 100 (~7000 U) µg/kg body weight of the active material. Preferable doses for treatment of anemic conditions are about 50 to about 300 Units/kg three times a week. Because the present invention provides an G-CSF with an enhanced in vivo residence time, the stated dosages are optionally lowered when a composition of the invention is administered.

Dosage Forms

In preferred aspects, according to any of the methods set forth above, the peptide conjugates used for treating conditions related to hematopoiesis or myelosuppression are provided in an oral dosage form. In preferred embodiments, these oral dosage forms include the following components: (a) a peptide which is a covalent conjugate between a G-CSF peptide and a water-soluble polymer, wherein the water-soluble polymer is covalently attached to the G-CSF peptide at a glycosyl or amino acid residue of the G-CSF peptide via an intact glycosyl linking group; (b) one or more surfactants; (c) one or more fatty acids; and (d) enteric material. In particularly preferred embodiments, the peptide, surfactants and fatty acids are mixed in liquid phase and lyophilized prior to combination with enteric material.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The following examples are provided to illustrate the compositions and methods and of the present invention, but not to limit the claimed invention.

EXAMPLES

Example 1

Pharmacodynamic Data on Neutrophil Count in Response to G-CSF Conjugate Peptide of the Invention Pharmacodynamic studies of neutrophil count in response to G-CSF conjugates of the invention and the commercially available G-CSF Neulasta showed that the compositions of the invention showed a similar time course of action to Neulasta (FIG. 1) at the same concentration. There was a dose dependence in the neutrophil count, with increasing concentrations of the G-CSF conjugates of the invention (Glyco-PEG G-CSF) resulting in an increased number of neutrophils at the peak of the time course of activity. Glyco-PEG G-CSF produced an approximately 30% greater response than Neulasta, indicating a 60% higher bioavailability for Glyco-PEG G-CSF than Neulasta at comparable doses.

This study included 53 subjects. There were 20 subjects in each dose group, with 15 subjects randomized to Glyco-PEG G-CSF and five to Neulasta. Glyco-PEG G-CSF was generally well tolerated with an adverse event profile similar to Neulasta. There were no discontinuations for adverse events. Nor were there any serious adverse events. In addition, no antibodies to Glyco-PEG G-CSF were detected.

Table 4 lists some representative data points for three different concentrations of Glyco-PEG G-CSF over a period of time from 24 to 168 hours after administration of Glyco-PEG G-CSF.

TABLE 4

| Hours | Glyco-PEG G-CSF (100 µg) | Glyco-PEG G-CSF (50 µg) | Glyco-PEG G-CSF (25 µg) |
|---|---|---|---|
| 24 | 26,0778 | 27,8917 | 25,825 |
| 72 | 35,222 | 31,5167 | 16,550 |
| 96 | 36,9222 | 23,7667 | 12,4625 |
| 144 | 24,2667 | 19,625 | 11,7625 |
| 168 | 22,9556 | 16,8167 | 12,3625 |

Example 2

Figure 2:
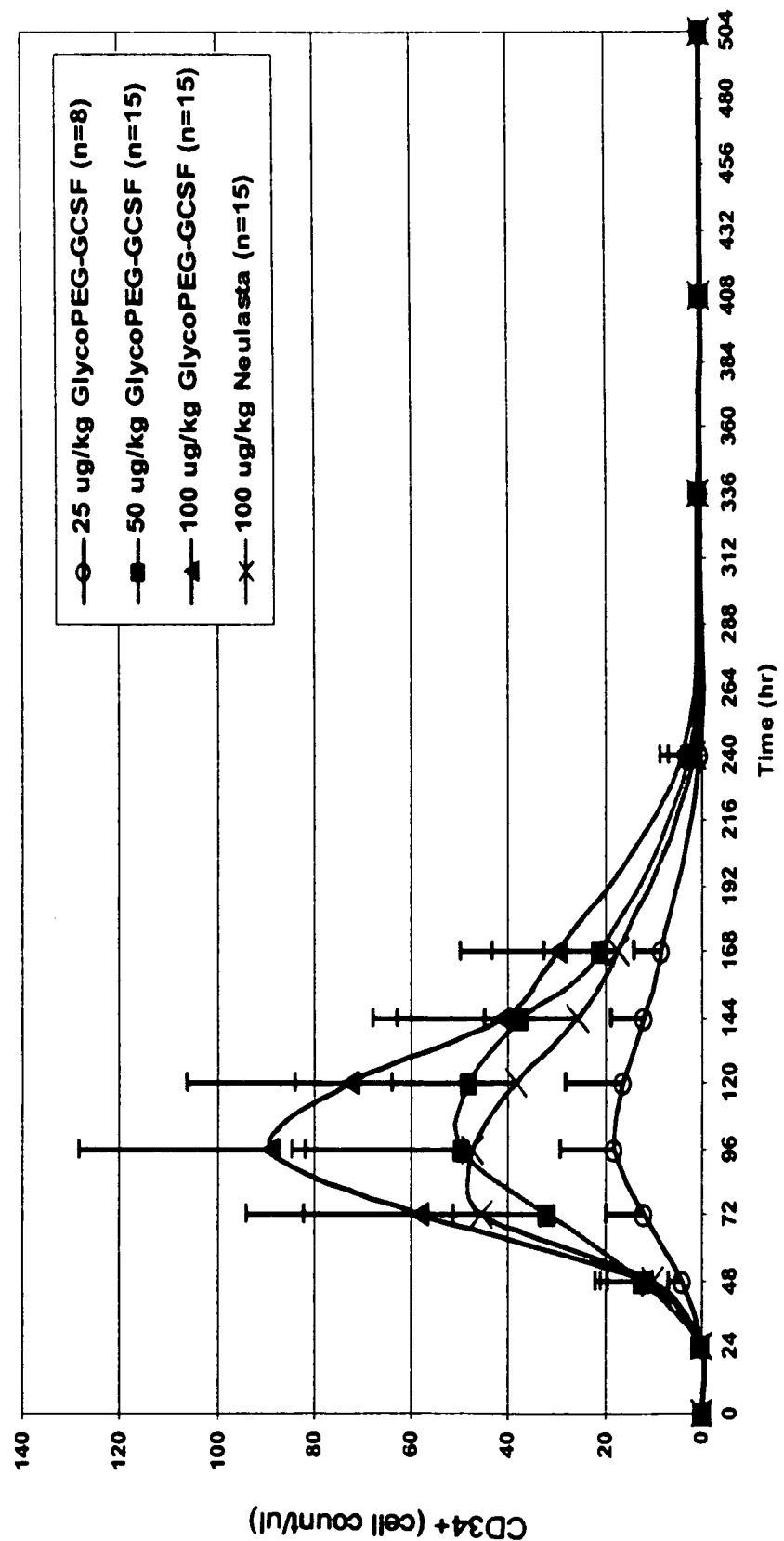
FIG. 2 illustrates data related to CD34+ cell count in response to XM22 (25 µg/kg; 50 µg/kg; 100 µg/kg) and Neulasta (100 µg/kg).

Pharmacodynamic Data on CD34+ Count in Response to G-CSF Conjugate Peptide of the Invention Pharmacodynamic studies of CD34+ count in response to G-CSF conjugates of the invention (Glyco-PEG G-CSF) and the commercially available G-CSF Neulasta showed that the compositions of the invention had a similar time course of action to Neulasta (FIG. 2) at the same concentration. Glyco-PEG G-CSF showed a significantly higher CD34+ count at its peak of activity than Neulasta at the same concentration.

There was a dose dependence in the cell count, with increasing concentrations of Glyco-PEG G-CSF resulting in an increased number of neutrophils at the peak of the time course of activity.

Table 5 lists some representative data points for three different concentrations of Glyco-PEG G-CSF over a period of time from 72 to 168 hours after administration of Glyco-PEG G-CSF.

TABLE 5

| Hours | Glyco-PEG G-CSF (100 µg) | Glyco-PEG G-CSF (50 µg) | Glyco-PEG G-CSF (25 µg) |
|---|---|---|---|
| 72 | 68,444 | 33 | 14 |
| 96 | 101 | 44,4167 | 20,125 |
| 120 | 76,222 | 43.5 | 18.5 |
| 144 | 43,667 | 33,9167 | 13,875 |
| 168 | 33 | 17,8333 | 10,375 |

Example 3

Figure 4:
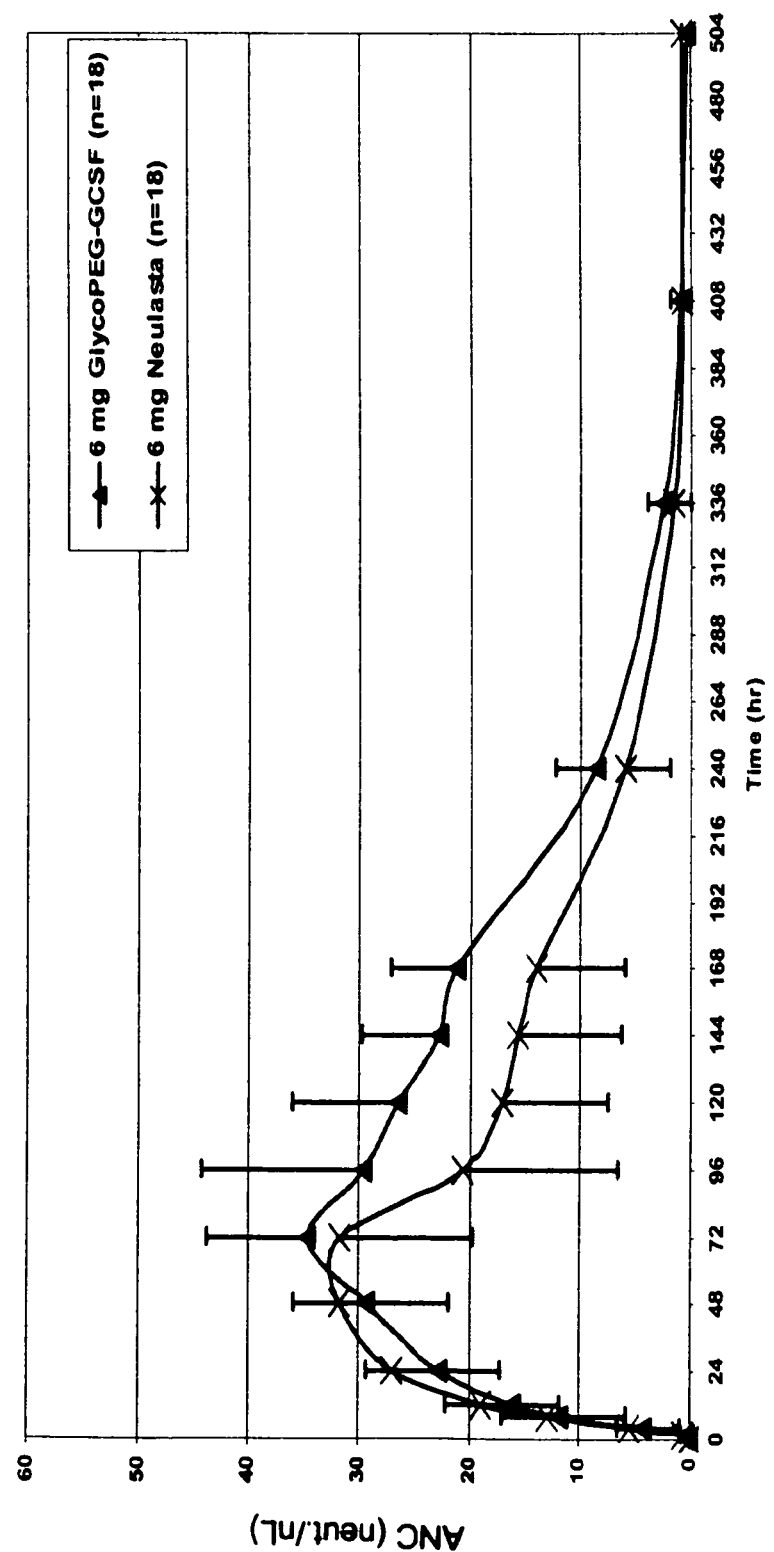
FIG. 4 illustrates data related to absolute neutrophil count (ANC) in response to XM22 (6 mg) and Neulasta (6 mg).

Pharmacodynamic Data on Neutrophil Count in Response to G-Csf Conjugate Peptide of the Invention: Fixed Dose Study A fixed-dose, pharmacodynamic study of neutrophil count in response to G-CSF conjugates of the invention (Glyco-PEG G-CSF) and the commercially available G-CSF Neulasta showed that the compositions of the invention showed a similar time course of action to Neulasta (FIG. 4). Glyco-PEG G-CSF produced an approximately 30% greater response than Neulasta, indicating a 60% higher bioavailability for Glyco-PEG G-CSF than Neulasta at this dose.

The study enrolled 36 healthy subjects. Glyco-PEG G-CSF was generally well tolerated, with adverse events similar to Neulasta. There were no discontinuations for adverse events, nor were there any serious adverse events. No antibodies to Glyco-PEG G-CSF were detected.

Example 4

Figure 5:
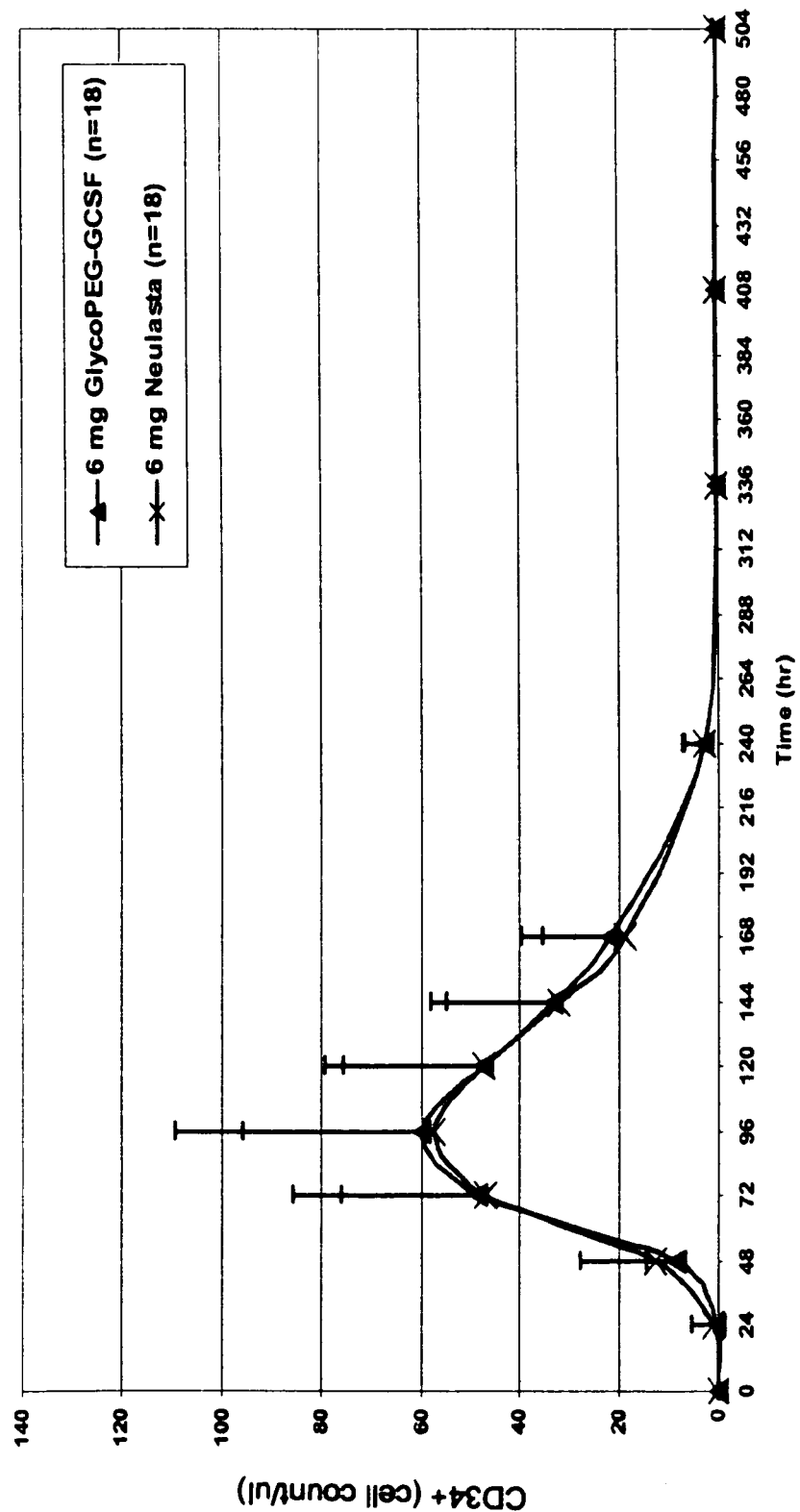
FIG. 5 illustrates data related to CD34+ cell count in response to XM22 (6 mg) and Neulasta (6 mg).
Figure 6:
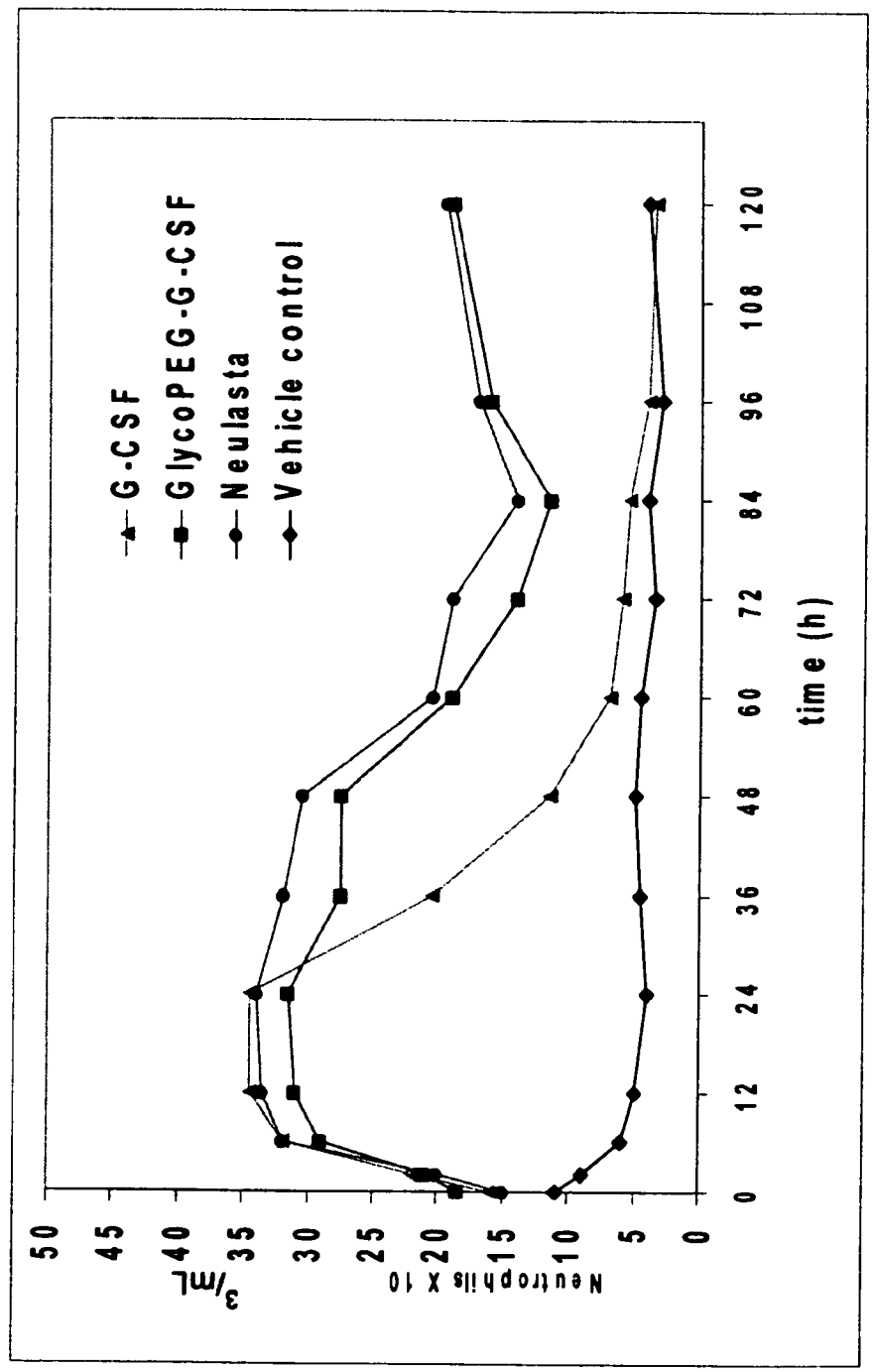
FIG. 6 illustrates pharmacodynamic data related to neutrophil count in response to G-CSF, GlycoPEG-G-CSF, Neulasta, and a control composition in cynomolgus monkeys.
Figure 7:
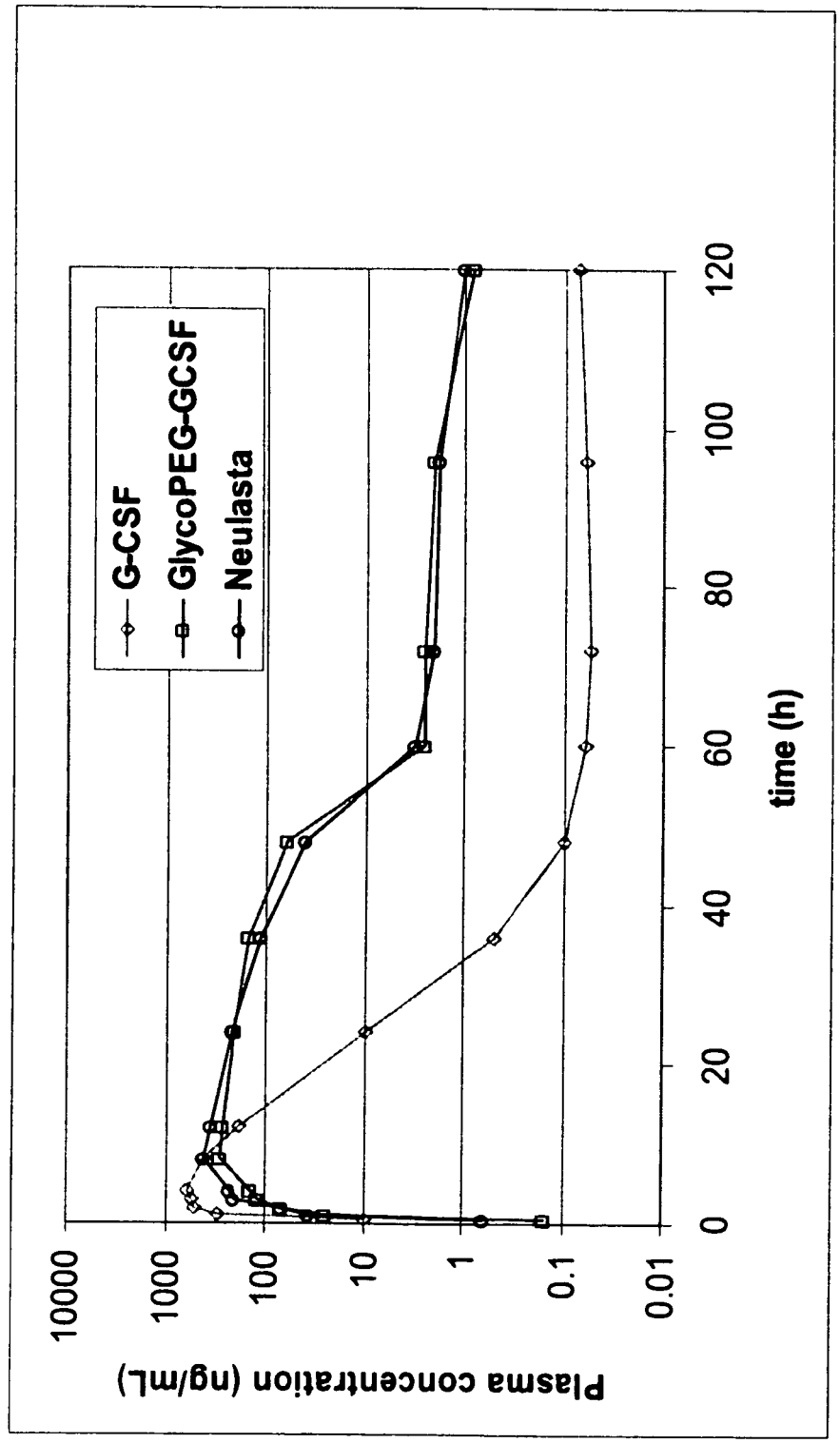
FIG. 7 illustrates pharmacokinetic data related to plasma concentrations of the indicated compounds in cynomolgus monkeys.
Figure 8:
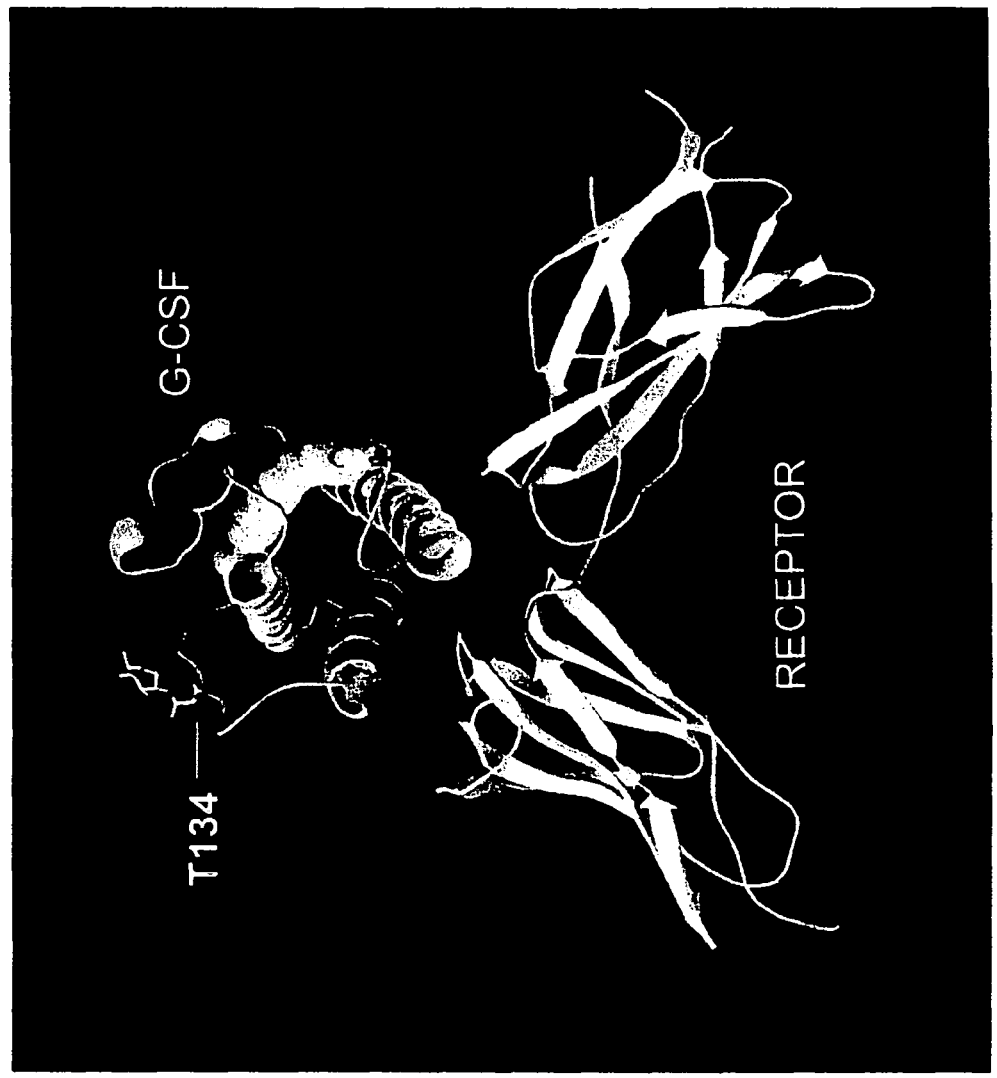
FIG. 8 is a schematic model of the structure of Glyco-PEG-GCSF and its receptor.
Figure 8:
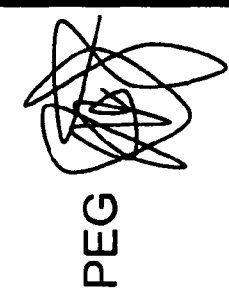
Figure 9:
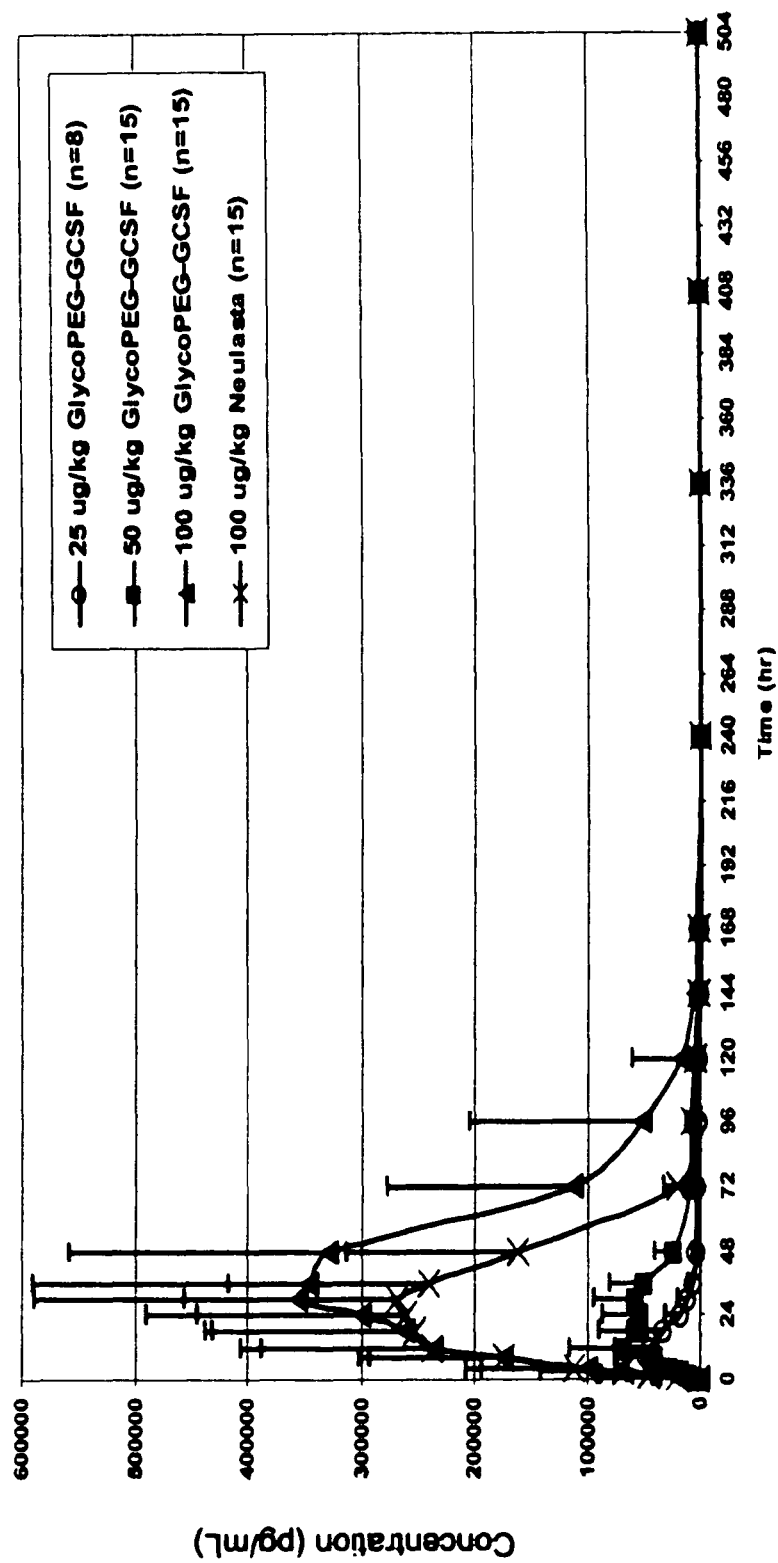
FIG. 9 illustrates data related to serum concentration of XM22 and Neulasta after administration of three different doses of XM22 and of 100 µg/kg Neulasta.
Figure 10:
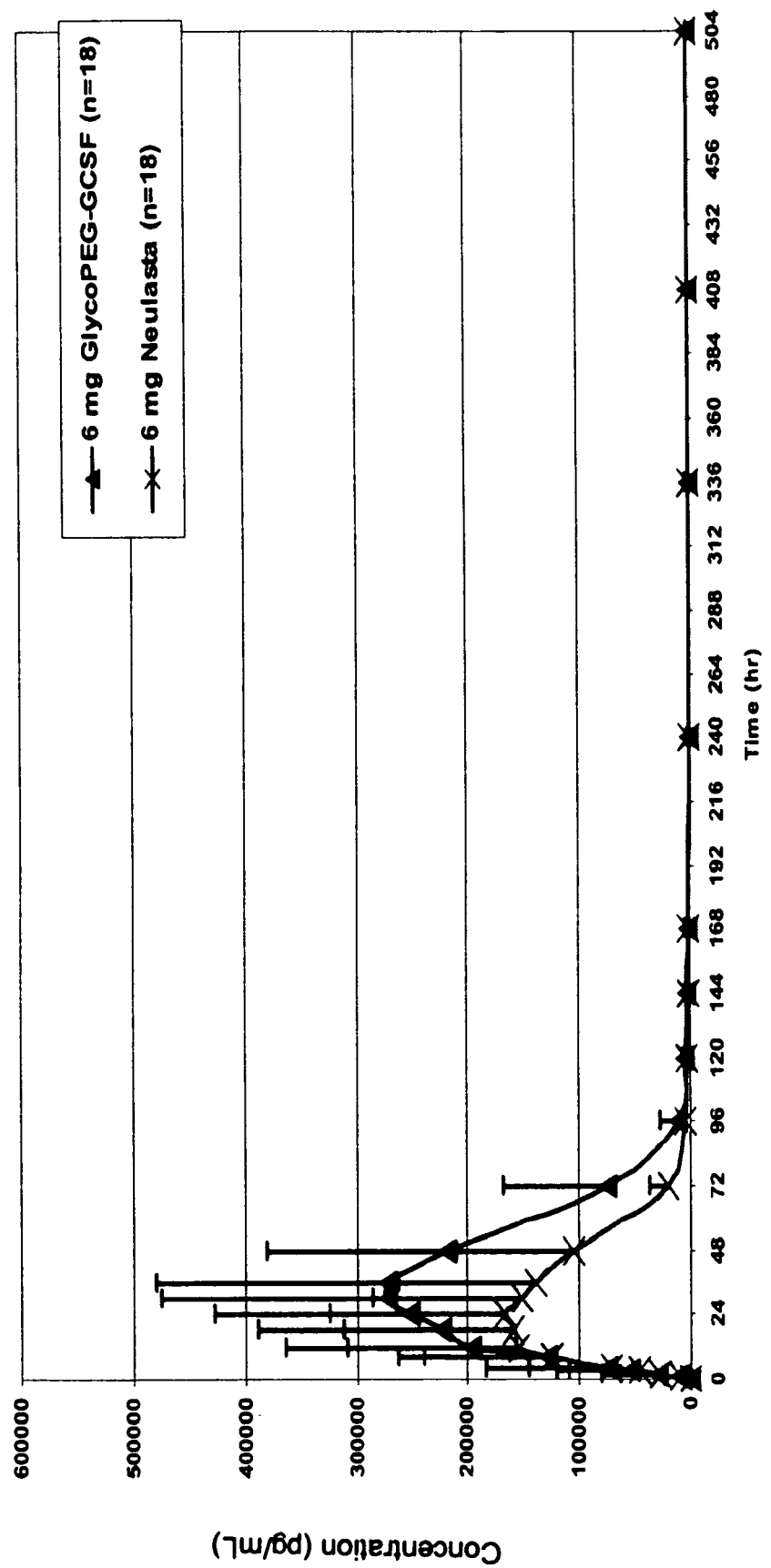
FIG. 10 illustrates data related to serum concentration of XM22 and Neulasta after administration of 6 mg XM22 and 6 mg Neulasta.

Pharmacodynamic Data on CD34+ Count in Response to G-CSF Conjugate Peptide of the Invention: Fixed Dose Study A fixed-dose, pharmacodynamic study of CD34+ count in response to G-CSF conjugates of the invention (Glyco-PEG G-CSF) and the commercially available G-CSF Neulasta showed that the compositions showed that the compositions of the invention showed a similar time course of action to that of Neulasta (FIG. 5).

Example 5

Mobilization of Allogenic/Autologous CD34+ Peripheral Blood Progenitor Cells Bone marrow transplant donors are treated with 10-20 µg/kg of glycopegylated GCSF (Glyco-PEG G-CSF) for five days to increase CD34+ cells from resting levels (~2 µL) to approximately 10/µL, which is an amount sufficient to provide 2-4×10$^6$ CD34+ cells/kg in a single apheresis. Bone marrow transplant donors may be allogenic (same as recipient) or autologous (different from recipient) donors.

What is claimed is:

1. A method for increasing stem cell production in a donor, said method comprising administering to said donor an amount of a covalent conjugate between a G-CSF peptide having the amino acid sequence according to SEQ ID NO: 1 and a poly(ethylene glycol) (PEG) group, wherein said covalent conjugate comprises a structure according to the formula

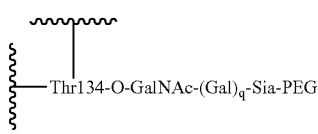

wherein
q is 0 or 1; and
Sia-PEG has a structure according to the formula:

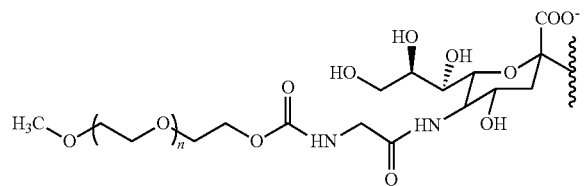

in which n is an integer from 400 to 500,
and wherein said amount is in a range from about 1 mg to about 20 mg or is a unit dosage form selected from 50 μg/kg, 100 μg/kg, and 200 μg/kg.

2. The method according to claim 1, wherein said PEG group has a molecular weight distribution that is essentially homodisperse.

3. The method according to claim 1, wherein q is 0.

4. A method for increasing the number of granulocytes in a subject, wherein said subject is eligible for a bone marrow transplant, said method comprising administering to said subject an amount of a covalent conjugate between a G-CSF peptide having the amino acid sequence according to SEQ ID NO: 1 and a poly(ethylene glycol) (PEG) group, wherein said covalent conjugate comprises a structure according to the formula

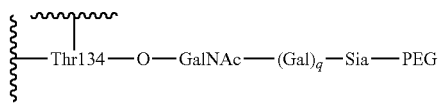

wherein
q is 0 or 1; and
Sia-PEG has a structure according to the formula:

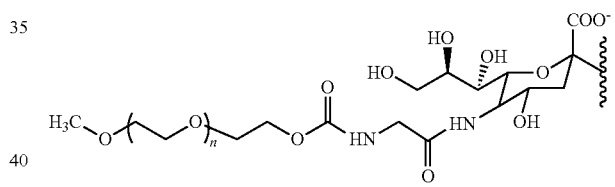

in which n is an integer from 400 to 500,
and wherein said amount is in a range from about 1 mg to about 20 mg or is a unit dosage form selected from 50 μg/kg, 100 μg/kg, and 200 μg/kg.

5. The method according to claim 4, wherein q is 0.

6. A method for preventing, treating, and alleviating myelosuppression resulting from a cancer therapy, said method comprising administering to a recipient of said cancer therapy an amount of amount of a covalent conjugate between a G-CSF peptide having the amino acid sequence according to SEQ ID NO: 1 and a poly(ethylene glycol) (PEG) group, wherein said covalent conjugate comprises a structure according to the formula

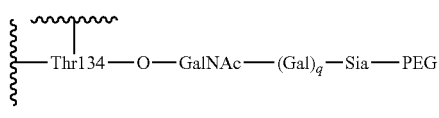

wherein
q is 0 or 1; and
Sia-PEG has a structure according to the formula:

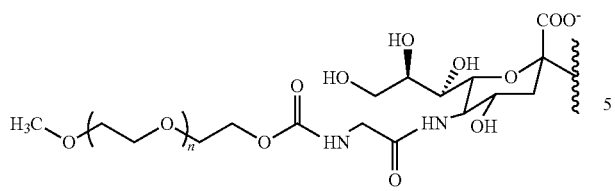

in which n is an integer from 400 to 500, and wherein said amount is in a range from about 1 mg to about 20 mg or is a unit dosage form selected from 50 μg/kg, 100 μg/kg, and 200 μg/kg.

7. The method according to claim 6, wherein said cancer therapy comprises a member selected from radiation therapy and chemotherapy.

8. The method according to claim 6, wherein q is 0.

9. A method of treating a condition in a subject in need thereof, said condition characterized by compromised white blood cell production in said subject, said method comprising the step of administering to said subject an amount of a covalent conjugate between a G-CSF peptide having the amino acid sequence according to SEQ ID NO: 1 and a poly(ethylene glycol) (PEG) group, wherein said covalent conjugate comprises a structure according to the formula

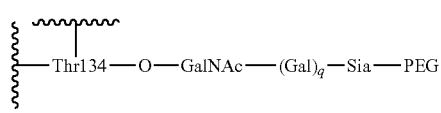

wherein q is 0 or 1; and

Sia-PEG has a structure according to the formula:

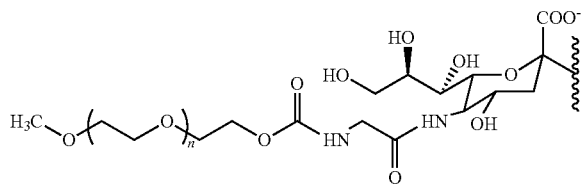

in which n is an integer from 400 to 500, wherein said amount is effective to ameliorate said condition in said subject, and wherein said amount is in a range from about 1 mg to about 20 mg or is a unit dosage form selected from 50 μg/kg, 100 μg/kg, and 200 μg/kg.

10. The method according to claim 9, wherein said compromised white blood cell production is a result of chemotherapy, radiation therapy, or idiopathic thrombocytopenia purpura.

11. The method according to claim 9, wherein q is 0.

12. A method for the treatment of neutropenia in a mammal comprising administering a pharmaceutically effective amount of a covalent conjugate between a G-CSF peptide having the amino acid sequence according to SEQ ID NO: 1 and a poly(ethylene glycol) (PEG) group, wherein said covalent conjugate comprises a structure according to the formula

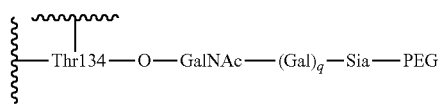

wherein q is 0 or 1; and

Sia-PEG has a structure according to the formula:

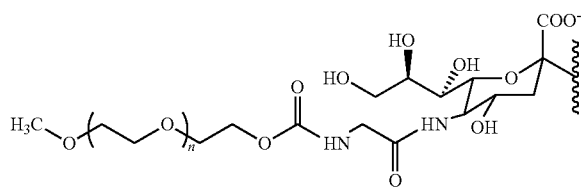

in which n is an integer from 400 to 500, and wherein said amount is in a range from about 1 mg to about 20 mg or is a unit dosage form selected from 50 μg/kg, 100 μg/kg, and 200 μg/kg.

13. The method according to claim 12, wherein q is 0.

14. A method for the treatment of thrombocytopenia in a mammal comprising administering a pharmaceutically effective amount of a covalent conjugate between a G-CSF peptide having the amino acid sequence according to SEQ ID NO: 1 and a poly(ethylene glycol) (PEG) group, wherein said covalent conjugate comprises a structure according to the formula

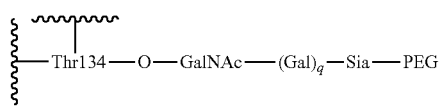

wherein q is 0 or 1; and

Sia-PEG has a structure according to the formula:

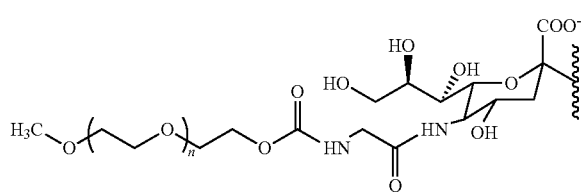

in which n is an integer from 400 to 500.

15. The method according to claim 14, wherein q is 0.

16. A method for expanding hematopoietic stem cells in culture, said method comprising the step of administering to said stem cells an effective amount of amount of a covalent conjugate between a G-CSF peptide having the amino acid sequence according to SEQ ID NO: 1 and a poly(ethylene glycol) (PEG) group, wherein said covalent conjugate comprises a structure according to the formula

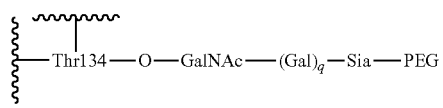

wherein
q is 0 or 1; and
Sia-PEG has a structure according to the formula:

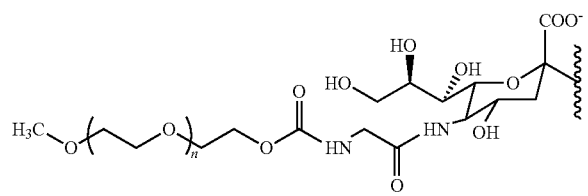

in which n is an integer from 400 to 500.

17. The method according to claim 16, wherein q is 0.

18. A method for increasing hematopoiesis in a subject, said method comprising the step of administering to said subject an effective amount of a covalent conjugate between a G-CSF peptide having the amino acid sequence according to SEQ ID NO: 1 and a poly(ethylene glycol) (PEG) group,
wherein said covalent conjugate comprises a structure according to the formula

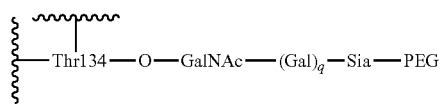

wherein
q is 0 or 1; and
Sia-PEG has a structure according to the formula:

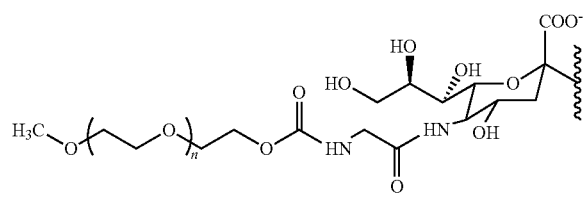

in which n is an integer from 400 to 500,
and wherein said amount is in a range from about 1 mg to about 20 mg or is a unit dosage form selected from 50 μg/kg, 100 μg/kg, and 200 μg/kg.

19. The method according to claim 18, wherein q is 0.

20. A method for increasing the number of hematopoietic progenitor cells in a subject, said method comprising administering to said subject an effective amount of a covalent conjugate between a G-CSF peptide having the amino acid sequence according to SEQ ID NO: 1 and a poly(ethylene glycol) (PEG) group,
wherein said covalent conjugate comprises a structure according to the formula

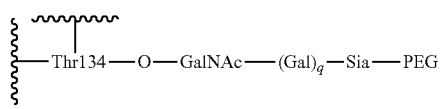

wherein
q is 0 or 1; and
Sia-PEG has a structure according to the formula:

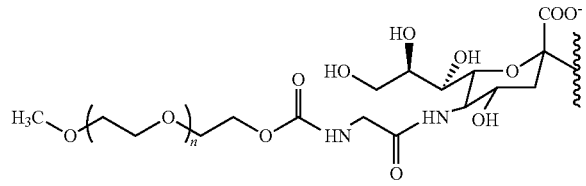

in which n is an integer from 400 to 500,
and wherein said amount is in a range from about 1 mg to about 20 mg or is a unit dosage form selected from 50 μg/kg, 100 μg/kg, and 200 μg/kg.

21. The method according to claim 20, wherein said hematopoietic progenitor cells are CD34+ cells.

22. The method according to claim 20, wherein q is 0.

23. A method for increasing stem cell production in a donor, said method comprising administering to said donor an effective amount of a covalent conjugate between a G-CSF peptide having the amino acid sequence according to SEQ ID NO: 1 and a poly(ethylene glycol) (PEG) group,
wherein said covalent conjugate comprises a structure according to the formula

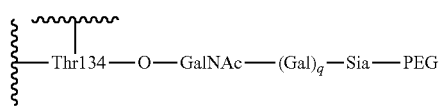

wherein
q is 0 or 1; and
Sia-PEG has a structure according to the formula:

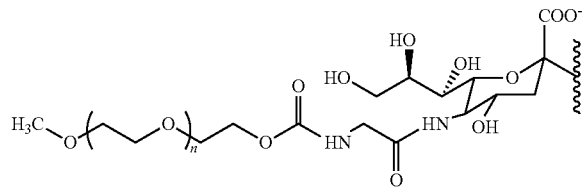

in which n is an integer from 400 to 500,
and wherein said amount is in a range from about 1 mg to about 20 mg or is a unit dosage form selected from 50 μg/kg, 100 μg/kg, and 200 μg/kg.

24. The method according to claim 23, wherein q is 0.

25. A method for providing stable engraftment of bone marrow, said method comprising:
(a) administering to a donor of said bone marrow an amount of a covalent conjugate between a G-CSF peptide having the amino acid sequence according to SEQ ID NO: 1 and a poly(ethylene glycol) (PEG) group,
wherein said covalent conjugate comprises a structure according to the formula

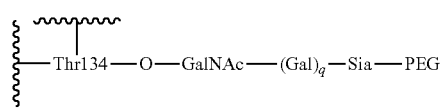

wherein
q is 0 or 1; and
Sia-PEG has a structure according to the formula:

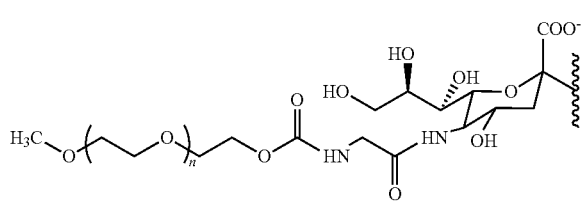

in which n is an integer from 400 to 500,
and wherein said amount is in a range from about 1 mg to about 20 mg or is a unit dosage form selected from 50 µg/kg, 100 µg/kg, and 200 µg/kg;

(b) isolating said bone marrow from said donor; and
(c) infusing said bone marrow into a recipient.

26. The method according to claim 25, wherein said donor is the same individual as said recipient.

27. The method according to claim 26, wherein said donor is a different individual from said recipient.

28. The method according to claim 25, wherein q is 0.

29. A method for increasing the number of hematopoietic progenitor cells in a subject, said method comprising administering to said subject:

(a) a first composition comprising a compound of formula (I) is 1,1'-[1,4-phenylene-bis-(methylene)-bis-1,4,8,11-tetraazacyclotetradecane (AMD3100); and (b) a second composition comprising an amount of a covalent conjugate between a G-CSF peptide having the amino acid sequence according to SEQ ID NO: 1 and a poly(ethylene glycol) (PEG) group, wherein said covalent conjugate comprises a structure according to the formula

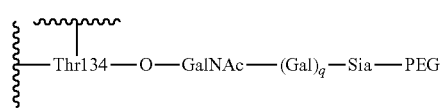

wherein
q is 0 or 1; and
Sia-PEG has a structure according to the formula:

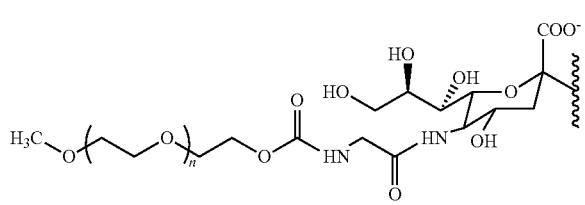

in which n is an integer from 400 to 500,
and wherein said amount is in a range from about 1 mg to about 20 mg or is a unit dosage form selected from 50 µg/kg, 100 µg/kg, and 200 µg/kg.

30. The method according to claim 29, wherein said first composition and said second composition are administered sequentially and in any order.

31. The method according to claim 29, wherein said first composition and said second composition are administered simultaneously.

32. The method according to claim 29, wherein said hematopoietic progenitor cells are CD34+ cells.

33. The method according to claim 29, wherein q is 0.

34. A method for increasing stem cell production in a donor, said method comprising administering to said donor an amount of a covalent conjugate between a G-CSF peptide having the amino acid sequence according to SEQ ID NO: 1 and a poly(ethylene glycol) (PEG) group, wherein said covalent conjugate comprises a structure according to the formula

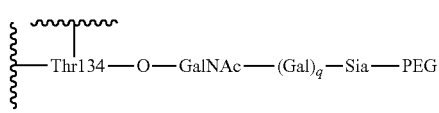

wherein
q is 0 or 1; and
Sia-PEG has a structure according to the formula:

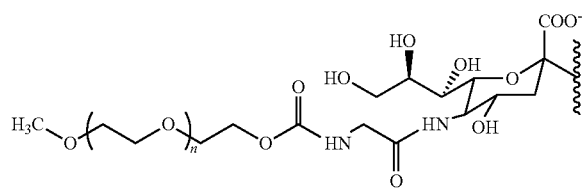

in which n is an integer from 400 to 500,
and wherein said amount is in a range from about 1 mg to about 20 mg.

35. The method according to claim 34, wherein q is 0.

36. A method for increasing stem cell production in a donor, said method comprising administering to said donor an amount of a covalent conjugate between a G-CSF peptide having the amino acid sequence according to SEQ ID NO: 1 and a poly(ethylene glycol) (PEG) group, wherein said covalent conjugate comprises a structure according to the formula

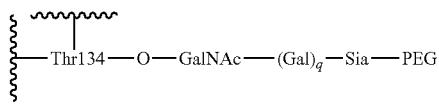

wherein
q is 0 or 1; and
Sia-PEG has a structure according to the formula:

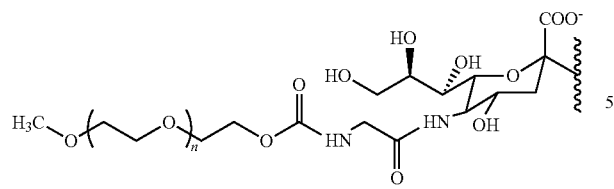
in which n is an integer from 400 to 500,
and wherein said amount is a unit dosage form selected from: 25 μg/kg, 50 μg/kg, 100 μg/kg, and 200 μg/kg.
37. The method according to claim 36, wherein q is 0.
* * * * *

SEQUENCE LISTING

<160> NUMBER OF SEQ ID NOS: 11

<210> SEQ ID NO 1
<211> LENGTH: 175
<212> TYPE: PRT
<213> ORGANISM: Homo sapiens
<220> FEATURE:
<221> NAME/KEY: MISC_FEATURE
<222> LOCATION: (1)..(175)
<223> OTHER INFORMATION: wild-type human G-CSF with an N-terminal
      methionine

<400> SEQUENCE: 1

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 2
<211> LENGTH: 174
<212> TYPE: PRT
<213> ORGANISM: Homo sapiens
<220> FEATURE:
<221> NAME/KEY: MISC_FEATURE
<222> LOCATION: (1)..(174)
<223> OTHER INFORMATION: wild-type human G-CSF

<400> SEQUENCE: 2

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp

```
                  100                 105                 110
Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 3
<211> LENGTH: 178
<212> TYPE: PRT
<213> ORGANISM: Artificial
<220> FEATURE:
<223> OTHER INFORMATION: G-CSF variant

<400> SEQUENCE: 3

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Val Ser Glu Cys Ala Thr Tyr Lys Leu Cys His Pro
            35                  40                  45

Glu Glu Leu Val Leu Leu Gly His Ser Leu Gly Ile Pro Trp Ala Pro
        50                  55                  60

Leu Ser Ser Cys Pro Ser Gln Ala Leu Gln Leu Ala Gly Cys Leu Ser
65                  70                  75                  80

Gln Leu His Ser Gly Leu Phe Leu Tyr Gln Gly Leu Leu Gln Ala Leu
                85                  90                  95

Glu Gly Ile Ser Pro Glu Leu Gly Pro Thr Leu Asp Thr Leu Gln Leu
            100                 105                 110

Asp Val Ala Asp Phe Ala Thr Thr Ile Trp Gln Gln Met Glu Glu Leu
        115                 120                 125

Gly Met Ala Pro Ala Leu Gln Pro Thr Gln Gly Ala Met Pro Ala Phe
    130                 135                 140

Ala Ser Ala Phe Gln Arg Arg Ala Gly Gly Val Leu Val Ala Ser His
145                 150                 155                 160

Leu Gln Ser Phe Leu Glu Val Ser Tyr Arg Val Leu Arg His Leu Ala
                165                 170                 175

Gln Pro

<210> SEQ ID NO 4
<211> LENGTH: 204
<212> TYPE: PRT
<213> ORGANISM: Artificial
<220> FEATURE:
<223> OTHER INFORMATION: G-CSF variant

<400> SEQUENCE: 4

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
                20                  25                  30

Leu Gly Pro Ala Ser Ser Leu Pro Gln Ser Phe Leu Leu Lys Cys Leu
            35                  40                  45

Glu Gln Val Arg Lys Ile Gln Gly Asp Gly Ala Ala Leu Gln Glu Lys
```

```
                    50                  55                  60

Leu Cys Ala Thr Tyr Lys Leu Cys His Pro Glu Glu Leu Val Leu Leu
 65                  70                  75                  80

Gly His Ser Leu Gly Ile Pro Trp Ala Pro Leu Ser Ser Cys Pro Ser
                 85                  90                  95

Gln Ala Leu Gln Leu Ala Gly Cys Leu Ser Gln Leu His Ser Gly Leu
                100                 105                 110

Phe Leu Tyr Gln Gly Leu Leu Gln Ala Leu Glu Gly Ile Ser Pro Glu
            115                 120                 125

Leu Gly Pro Thr Leu Asp Thr Leu Gln Leu Asp Val Ala Asp Phe Ala
            130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
                180                 185                 190

Val Ser Tyr Arg Val Leu Arg His Leu Ala Gln Pro
            195                 200

<210> SEQ ID NO 5
<211> LENGTH: 207
<212> TYPE: PRT
<213> ORGANISM: Artificial
<220> FEATURE:
<223> OTHER INFORMATION: G-CSF variant

<400> SEQUENCE: 5

Met Ala Gly Pro Ala Thr Gln Ser Pro Met Lys Leu Met Ala Leu Gln
  1               5                  10                  15

Leu Leu Leu Trp His Ser Ala Leu Trp Thr Val Gln Glu Ala Thr Pro
                 20                  25                  30

Leu Gly Pro Ala Ser Ser Leu Pro Gln Ser Phe Leu Leu Lys Cys Leu
             35                  40                  45

Glu Gln Val Arg Lys Ile Gln Gly Asp Gly Ala Ala Leu Gln Glu Lys
 50                  55                  60

Leu Val Ser Glu Cys Ala Thr Tyr Lys Leu Cys His Pro Glu Glu Leu
 65                  70                  75                  80

Val Leu Leu Gly His Ser Leu Gly Ile Pro Trp Ala Pro Leu Ser Ser
                 85                  90                  95

Cys Pro Ser Gln Ala Leu Gln Leu Ala Gly Cys Leu Ser Gln Leu His
                100                 105                 110

Ser Gly Leu Phe Leu Tyr Gln Gly Leu Leu Gln Ala Leu Glu Gly Ile
            115                 120                 125

Ser Pro Glu Leu Gly Pro Thr Leu Asp Thr Leu Gln Leu Asp Val Ala
            130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
                180                 185                 190

Phe Leu Glu Val Ser Tyr Arg Val Leu Arg His Leu Ala Gln Pro
            195                 200                 205
```

```
<210> SEQ ID NO 6
<211> LENGTH: 176
<212> TYPE: PRT
<213> ORGANISM: Artificial
<220> FEATURE:
<223> OTHER INFORMATION: G-CSF variant

<400> SEQUENCE: 6

Met Val Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Thr Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

<210> SEQ ID NO 7
<211> LENGTH: 175
<212> TYPE: PRT
<213> ORGANISM: Artificial
<220> FEATURE:
<223> OTHER INFORMATION: G-CSF variant

<400> SEQUENCE: 7

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Thr Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140
```

```
Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
            165                 170                 175

<210> SEQ ID NO 8
<211> LENGTH: 176
<212> TYPE: PRT
<213> ORGANISM: Artificial
<220> FEATURE:
<223> OTHER INFORMATION: G-CSF variant

<400> SEQUENCE: 8

Met Val Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly Ser Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

<210> SEQ ID NO 9
<211> LENGTH: 176
<212> TYPE: PRT
<213> ORGANISM: Artificial
<220> FEATURE:
<223> OTHER INFORMATION: G-CSF variant

<400> SEQUENCE: 9

Met Gln Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110
```

```
Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175
```

<210> SEQ ID NO 10
<211> LENGTH: 181
<212> TYPE: PRT
<213> ORGANISM: Artificial
<220> FEATURE:
<223> OTHER INFORMATION: G-CSF variant

<400> SEQUENCE: 10

```
Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro Thr
                165                 170                 175

Gln Gly Ala Met Pro
            180
```

<210> SEQ ID NO 11
<211> LENGTH: 175
<212> TYPE: PRT
<213> ORGANISM: Artificial
<220> FEATURE:
<223> OTHER INFORMATION: G-CSF variant

<400> SEQUENCE: 11

```
Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly Ser Ser Leu Gly Ile Pro Trp Ala Pro Leu Ser Ser
```

```
                50                  55                  60
Cys Pro Ser Gln Ala Leu Gln Leu Ala Gly Cys Leu Ser Gln Leu His
65                   70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Thr Thr Thr Pro Thr Gln Thr Ala Met Pro Ala Phe Ala Ser Ala
                130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```